(12) United States Patent
Ignon et al.

(10) Patent No.: US 12,186,513 B2
(45) Date of Patent: Jan. 7, 2025

(54) DEVICES, SYSTEMS AND METHODS FOR SKIN TREATMENT

(71) Applicant: HydraFacial LLC, Long Beach, CA (US)

(72) Inventors: Roger Ignon, Redondo Beach, CA (US); Ed F. Nicolas, Signal Hill, CA (US)

(73) Assignee: HydraFacial LLC, Long Beach, CA (US)

( * ) Notice: Subject to any disclaimer, the term of this patent is extended or adjusted under 35 U.S.C. 154(b) by 0 days.

(21) Appl. No.: 17/952,665

(22) Filed: Sep. 26, 2022

(65) Prior Publication Data

US 2023/0018295 A1 Jan. 19, 2023

Related U.S. Application Data

(63) Continuation of application No. 17/332,897, filed on May 27, 2021, which is a continuation of application
(Continued)

(51) Int. Cl.
| | | |
|---|---|---|
| *A61M 35/00* | (2006.01) | |
| *A61B 17/32* | (2006.01) | |
| *A61B 17/54* | (2006.01) | |

(52) U.S. Cl.
CPC .......... *A61M 35/003* (2013.01); *A61B 17/32* (2013.01); *A61B 17/54* (2013.01); *A61B 2017/320004* (2013.01)

(58) Field of Classification Search
CPC ........... A61B 2017/00761; A61B 2017/00747; A61B 2017/320004; A61B 2017/32; A61B 2017/54; A61M 35/00; A61M 35/003
(Continued)

(56) References Cited

U.S. PATENT DOCUMENTS

| | | |
|---|---|---|
| 1,651,585 A | 12/1927 | Clair |
| D117,295 S | 10/1939 | Smith |

(Continued)

FOREIGN PATENT DOCUMENTS

| | | |
|---|---|---|
| AT | 400305 | 12/1995 |
| AU | 1014299 | 5/1999 |

(Continued)

OTHER PUBLICATIONS

U.S. Appl. No. 09/648,025 (U.S. Pat. No. 6,641,591), filed Aug. 25, 2000, Instruments and Techniques for Controlled Removal of Epidermal Layers.

(Continued)

*Primary Examiner* — Jacqueline F Stephens

(74) *Attorney, Agent, or Firm* — Knobbe, Martens, Olson & Bear, LLP

(57) ABSTRACT

A device for treating the skin comprises a handpiece assembly having a distal end and a proximal end, a cartridge comprising an interior cavity and a tip on the distal end of the handpiece assembly. The handpiece assembly includes a fluid delivery conduit and a waste conduit. In addition, the cartridge is coupled to the handpiece assembly with the interior cavity of the cartridge being in fluid communication with the fluid delivery conduit. Further, the tip is configured to contact the skin. The tip comprises a peripheral lip, a first opening in fluid communication with the fluid delivery conduit, a second opening in fluid communication with the waste conduit and an abrasive element. The first opening, the second opening and the abrasive element of the tip are generally positioned within the peripheral lip.

18 Claims, 37 Drawing Sheets

Related U.S. Application Data

No. 14/734,995, filed on Jun. 9, 2015, now Pat. No. 11,020,577, which is a continuation of application No. 12/362,353, filed on Jan. 29, 2009, now Pat. No. 9,056,193.

(60) Provisional application No. 61/024,504, filed on Jan. 29, 2008.

(58) Field of Classification Search
USPC .................................. 604/289, 290, 291
See application file for complete search history.

(56) References Cited

U.S. PATENT DOCUMENTS

| | | |
|---|---|---|
| D151,807 S | 11/1948 | Berkowitz |
| 2,608,032 A | 8/1952 | Garver |
| 2,631,583 A | 3/1953 | Lavergne |
| 2,701,559 A | 2/1955 | Cooper |
| 2,712,823 A | 7/1955 | Kurtin |
| 2,867,214 A | 1/1959 | Wilson |
| 2,881,763 A | 4/1959 | Robbins |
| 2,921,585 A | 1/1960 | Schumann |
| 3,037,509 A | 6/1962 | Schutz |
| 3,085,573 A | 4/1963 | Meyer et al. |
| 3,214,869 A | 11/1965 | Stryker |
| 3,468,079 A | 9/1969 | Kaufman |
| 3,476,112 A | 11/1969 | Elstein |
| 3,481,677 A | 12/1969 | Abrahamson |
| 3,505,993 A | 4/1970 | Lewes et al. |
| 3,560,100 A | 2/1971 | Spatz |
| 3,574,239 A | 4/1971 | Sollerud |
| 3,608,553 A | 9/1971 | Balamuth |
| 3,715,838 A | 2/1973 | Young et al. |
| 3,865,352 A | 2/1975 | Nelson et al. |
| 3,866,264 A | 2/1975 | Engquist |
| D237,776 S | 11/1975 | Arassa et al. |
| D237,863 S | 12/1975 | Peters et al. |
| 3,930,598 A | 1/1976 | Slagle |
| 3,948,265 A | 4/1976 | Al Ani |
| 3,964,212 A | 6/1976 | Karder |
| 3,968,789 A | 7/1976 | Simoncini |
| 3,977,084 A | 8/1976 | Sloan |
| 4,121,388 A | 10/1978 | Wilson |
| 4,155,721 A | 5/1979 | Fletcher |
| 4,170,821 A | 10/1979 | Booth |
| 4,182,329 A | 1/1980 | Smit et al. |
| 4,203,431 A | 5/1980 | Abura et al. |
| D255,325 S | 6/1980 | Hoyt |
| 4,216,233 A | 8/1980 | Stein |
| 4,225,254 A | 9/1980 | Holberg et al. |
| D258,348 S | 2/1981 | Hoyt |
| D259,921 S | 7/1981 | Hartmann |
| D260,176 S | 8/1981 | Boschetti et al. |
| 4,289,158 A | 9/1981 | Nehring |
| 4,299,219 A | 11/1981 | Norris, Jr. |
| 4,342,522 A | 8/1982 | Mackles |
| 4,378,804 A | 4/1983 | Cortese |
| 4,500,222 A | 2/1985 | Clading-Boel |
| 4,560,373 A | 12/1985 | Sugino et al. |
| D288,293 S | 2/1987 | Arvans |
| 4,646,480 A | 3/1987 | Williams |
| 4,646,482 A | 3/1987 | Chitjian |
| 4,655,743 A | 4/1987 | Hyde |
| 4,671,412 A | 6/1987 | Gatten |
| 4,676,749 A | 6/1987 | Mabille |
| D290,999 S | 7/1987 | Novak |
| 4,706,676 A | 11/1987 | Peck |
| 4,718,467 A | 1/1988 | Di Gianfilippo et al. |
| 4,754,756 A | 7/1988 | Shelanski |
| 4,757,814 A | 7/1988 | Wang et al. |
| 4,764,362 A | 8/1988 | Barchas |
| 4,795,421 A | 1/1989 | Blasius, Jr. et al. |
| 4,811,734 A | 3/1989 | McGurk-Burleson et al. |
| 4,836,192 A | 6/1989 | Abbate |
| 4,866,202 A | 9/1989 | Weil |
| 4,875,287 A | 10/1989 | Creasy et al. |
| 4,886,078 A | 12/1989 | Shiffman |
| 4,887,994 A | 12/1989 | Bedford |
| 4,900,316 A | 2/1990 | Yamamoto |
| 4,917,086 A | 4/1990 | Feltovich et al. |
| 4,925,450 A | 5/1990 | Imonti et al. |
| D308,480 S | 6/1990 | Hoyt |
| 4,940,350 A | 7/1990 | Kim |
| 4,957,747 A | 9/1990 | Stiefel |
| 4,990,841 A | 2/1991 | Elder |
| 5,006,004 A | 4/1991 | Dirksing et al. |
| 5,006,339 A | 4/1991 | Bargery et al. |
| 5,012,797 A | 5/1991 | Clarke |
| D317,719 S | 6/1991 | Hestehave et al. |
| 5,035,089 A | 7/1991 | Tillman et al. |
| 5,037,431 A | 8/1991 | Summers et al. |
| 5,037,432 A | 8/1991 | Molinari |
| 5,054,339 A | 10/1991 | Yacowitz |
| 5,100,412 A | 3/1992 | Rosso |
| 5,100,424 A | 3/1992 | Jang |
| 5,119,839 A | 6/1992 | Rudolph |
| 5,122,153 A | 6/1992 | Harrel |
| 5,171,215 A | 12/1992 | Flanagan |
| 5,192,269 A | 3/1993 | Poli et al. |
| 5,207,234 A | 5/1993 | Rosso |
| 5,217,455 A | 6/1993 | Tan |
| 5,222,956 A | 6/1993 | Waldron |
| 5,242,433 A | 9/1993 | Smith et al. |
| 5,254,109 A | 10/1993 | Smith et al. |
| 5,290,273 A | 3/1994 | Tan |
| 5,368,581 A | 11/1994 | Smith et al. |
| 5,387,215 A | 2/1995 | Fisher |
| 5,391,151 A | 2/1995 | Wilmot |
| 5,417,674 A | 5/1995 | Smith et al. |
| 5,419,772 A | 5/1995 | Teitz et al. |
| 5,423,803 A | 6/1995 | Tankovich et al. |
| 5,437,372 A | 8/1995 | Per-Lee |
| 5,441,490 A | 8/1995 | Svedman |
| 5,460,620 A | 10/1995 | Smith et al. |
| 5,470,323 A | 11/1995 | Smith et al. |
| 5,484,427 A | 1/1996 | Gibbons |
| 5,490,736 A | 2/1996 | Haber et al. |
| 5,512,044 A | 4/1996 | Duer |
| 5,562,642 A | 10/1996 | Smith et al. |
| 5,562,643 A | 10/1996 | Johnson |
| 5,611,687 A | 3/1997 | Wagner |
| 5,612,797 A | 3/1997 | Clarke |
| 5,618,275 A | 4/1997 | Bock |
| 5,626,631 A | 5/1997 | Eckhouse |
| 5,658,323 A | 8/1997 | Miller |
| 5,658,583 A | 8/1997 | Zhang et al. |
| 5,674,235 A | 10/1997 | Parisi |
| 5,676,643 A | 10/1997 | Cann et al. |
| 5,676,648 A | 10/1997 | Henley |
| 5,683,971 A | 11/1997 | Rose et al. |
| 5,697,920 A | 12/1997 | Gibbons |
| 5,707,383 A | 1/1998 | Bays |
| 5,713,785 A | 2/1998 | Nishio |
| 5,735,833 A | 4/1998 | Olson |
| 5,755,751 A | 5/1998 | Eckhouse |
| 5,759,185 A | 6/1998 | Grinberg |
| 5,762,640 A | 6/1998 | Kajiwara et al. |
| 5,779,519 A | 7/1998 | Oliver |
| 5,800,446 A | 9/1998 | Banuchi |
| 5,807,353 A | 9/1998 | Schmitz |
| 5,810,842 A | 9/1998 | Di Fiore et al. |
| 5,813,416 A | 9/1998 | Rudolph |
| 5,817,050 A | 10/1998 | Klein |
| 5,817,089 A | 10/1998 | Tankovich et al. |
| 5,834,510 A | 11/1998 | Yu et al. |
| 5,846,215 A | 12/1998 | Zygmont |
| 5,848,998 A | 12/1998 | Marasco, Jr. |
| 5,857,995 A | 1/1999 | Thomas et al. |
| 5,861,142 A | 1/1999 | Schick |
| 5,873,881 A | 2/1999 | McEwen et al. |
| 5,879,323 A | 3/1999 | Henley |
| 5,879,376 A | 3/1999 | Miller |
| 5,882,201 A | 3/1999 | Salem |

(56) References Cited

U.S. PATENT DOCUMENTS

| | | |
|---|---|---|
| 5,885,260 A | 3/1999 | Mehl, Sr. et al. |
| 5,908,401 A | 6/1999 | Henley |
| 5,911,223 A | 6/1999 | Weaver et al. |
| 5,919,152 A | 7/1999 | Zygmont |
| 5,919,479 A | 7/1999 | Zhang et al. |
| 5,954,730 A | 9/1999 | Bernabei |
| 5,971,999 A | 10/1999 | Naldoni |
| 5,980,555 A | 11/1999 | Barbut et al. |
| 6,019,749 A | 2/2000 | Fields et al. |
| 6,023,639 A | 2/2000 | Hakky et al. |
| 6,024,733 A | 2/2000 | Eggers et al. |
| 6,027,402 A | 2/2000 | Oliver |
| 6,027,495 A | 2/2000 | Miller |
| 6,032,071 A | 2/2000 | Binder |
| 6,036,684 A | 3/2000 | Tankovich et al. |
| 6,039,745 A | 3/2000 | Di Fiore et al. |
| 6,042,552 A | 3/2000 | Cornier |
| D425,241 S | 5/2000 | Nishizawa et al. |
| 6,074,382 A | 6/2000 | Asah et al. |
| 6,080,165 A | 6/2000 | DeJacma |
| 6,080,166 A | 6/2000 | McEwen et al. |
| D428,142 S | 7/2000 | Stromblad |
| 6,090,085 A | 7/2000 | Mehl, Sr. et al. |
| 6,093,021 A | 7/2000 | Rainey |
| 6,113,559 A | 9/2000 | Klopotek |
| 6,120,512 A | 9/2000 | Bernabei |
| 6,129,701 A | 10/2000 | Cimino |
| 6,136,008 A | 10/2000 | Becker et al. |
| 6,139,553 A | 10/2000 | Dotan |
| 6,139,554 A | 10/2000 | Karkar et al. |
| 6,142,155 A | 11/2000 | Rudolph |
| 6,149,634 A | 11/2000 | Bernabei |
| 6,149,644 A | 11/2000 | Xie |
| 6,159,226 A | 12/2000 | Kim |
| 6,162,218 A | 12/2000 | Elbrecht et al. |
| 6,162,232 A | 12/2000 | Shadduck |
| 6,165,059 A | 12/2000 | Parkin et al. |
| 6,174,325 B1 | 1/2001 | Eckhouse |
| 6,176,198 B1 | 1/2001 | Kao et al. |
| 6,183,451 B1 | 2/2001 | Mehl, Sr. et al. |
| 6,183,483 B1 | 2/2001 | Chang |
| 6,190,376 B1 | 2/2001 | Asah et al. |
| 6,193,589 B1 | 2/2001 | Khalaj |
| 6,196,982 B1 | 3/2001 | Ball |
| 6,231,593 B1 | 5/2001 | Meserol |
| 6,235,039 B1 | 5/2001 | Parkin et al. |
| 6,238,275 B1 | 5/2001 | Metcalf et al. |
| 6,241,739 B1 | 6/2001 | Waldron |
| 6,245,347 B1 | 6/2001 | Zhang et al. |
| 6,264,666 B1 | 7/2001 | Coleman et al. |
| 6,269,271 B1 | 7/2001 | Bernabei |
| 6,277,116 B1 | 8/2001 | Utely et al. |
| 6,277,128 B1 | 8/2001 | Muldner |
| 6,280,438 B1 | 8/2001 | Eckhouse et al. |
| 6,283,978 B1 | 9/2001 | Cheski et al. |
| 6,284,266 B1 | 9/2001 | Zhang et al. |
| 6,299,620 B1 | 10/2001 | Shadduck |
| 6,306,119 B1 | 10/2001 | Weber et al. |
| 6,306,147 B1 | 10/2001 | Bernabei et al. |
| 6,322,548 B1 | 11/2001 | Payne et al. |
| 6,322,568 B1 | 11/2001 | Bemnabel et al. |
| 6,325,381 B1 | 12/2001 | von Engelbrechten |
| 6,325,769 B1 | 12/2001 | Klopotek |
| 6,332,886 B1 | 12/2001 | Green et al. |
| 6,334,074 B1 | 12/2001 | Spertell |
| 6,355,054 B1 | 3/2002 | Neuberger |
| 6,368,333 B2 | 4/2002 | Bernabei et al. |
| 6,383,177 B1 | 5/2002 | Balle-Petersen et al. |
| 6,387,089 B1 | 5/2002 | Kreindel et al. |
| 6,387,103 B2 | 5/2002 | Shadduck |
| 6,401,289 B1 | 6/2002 | Herbert |
| 6,409,736 B1 | 6/2002 | Bernabei |
| 6,410,599 B1 | 6/2002 | Johnson |
| RE37,796 E | 7/2002 | Henley |
| 6,414,032 B1 | 7/2002 | Johnson |
| 6,420,431 B1 | 7/2002 | Johnson |
| 6,423,078 B1 | 7/2002 | Bays et al. |
| 6,423,750 B1 | 7/2002 | Johnson |
| 6,432,113 B1 | 8/2002 | Parkin et al. |
| 6,432,114 B1 | 8/2002 | Rosso |
| 6,458,109 B1 | 10/2002 | Henley et al. |
| 6,471,712 B2 | 10/2002 | Burres |
| 6,477,410 B1 | 11/2002 | Henley et al. |
| 6,482,212 B1 | 11/2002 | Bernabei et al. |
| 6,485,452 B1 | 11/2002 | French et al. |
| 6,488,646 B1 | 12/2002 | Zygmont |
| 6,494,856 B1 | 12/2002 | Zygmont |
| 6,500,183 B1 | 12/2002 | Waldron |
| 6,503,256 B2 | 1/2003 | Parkin et al. |
| 6,508,813 B1 | 1/2003 | Altshuler |
| 6,511,486 B2 | 1/2003 | Mercier et al. |
| 6,514,243 B1 | 2/2003 | Eckhouse et al. |
| 6,514,262 B1 | 2/2003 | Di Fiore et al. |
| 6,514,278 B1 | 2/2003 | Hibst et al. |
| 6,518,538 B2 | 2/2003 | Bernabei |
| 6,520,931 B2 | 2/2003 | Suh |
| D472,136 S | 3/2003 | Hermann |
| 6,527,716 B1 | 3/2003 | Eppstein |
| 6,527,783 B1 | 3/2003 | Ignon |
| 6,533,776 B2 | 3/2003 | Asah et al. |
| 6,535,761 B2 | 3/2003 | Bernabei |
| 6,537,242 B1 | 3/2003 | Palmer |
| 6,540,757 B1 | 4/2003 | Hruska et al. |
| 6,546,281 B1 | 4/2003 | Zhang et al. |
| 6,562,013 B1 | 5/2003 | Marasco, Jr. |
| 6,562,050 B1 | 5/2003 | Owen |
| 6,564,093 B1 | 5/2003 | Ostrow et al. |
| 6,565,535 B2 | 5/2003 | Zaias et al. |
| 6,569,157 B1 | 5/2003 | Shain et al. |
| 6,582,442 B2 | 6/2003 | Simon et al. |
| 6,587,730 B2 | 7/2003 | Bernabei |
| 6,589,218 B2 | 7/2003 | Garcia |
| 6,592,595 B1 | 7/2003 | Mallett et al. |
| 6,595,934 B1 | 7/2003 | Hissong et al. |
| 6,611,706 B2 | 8/2003 | Avrahami et al. |
| 6,626,445 B2 | 9/2003 | Murphy et al. |
| 6,629,927 B1 | 10/2003 | Mesaros et al. |
| 6,629,971 B2 | 10/2003 | McDaniel |
| 6,629,974 B2 | 10/2003 | Penny et al. |
| 6,629,983 B1 | 10/2003 | Ignon |
| 6,635,035 B1 | 10/2003 | Marasco et al. |
| 6,641,591 B1 | 11/2003 | Shadduck |
| 6,645,184 B1 | 11/2003 | Zelickson et al. |
| 6,652,888 B2 | 11/2003 | Rhoades |
| 6,666,874 B2 | 12/2003 | Heitzmann et al. |
| 6,673,081 B1 | 1/2004 | Tavger et al. |
| 6,673,082 B2 | 1/2004 | Mallett et al. |
| D486,915 S | 2/2004 | Warschewske et al. |
| 6,685,853 B1 | 2/2004 | Angelopoulos et al. |
| 6,687,537 B2 | 2/2004 | Bernabei |
| 6,689,380 B1 | 2/2004 | Marchitto et al. |
| 6,695,853 B2 | 2/2004 | Karasiuk |
| 6,699,237 B2 | 3/2004 | Weber et al. |
| 6,712,805 B2 | 3/2004 | Weimann |
| 6,726,673 B1 | 4/2004 | Zhang et al. |
| D490,561 S | 5/2004 | Angeletta |
| 6,735,470 B2 | 5/2004 | Henley et al. |
| 6,743,211 B1 | 6/2004 | Prausnitz et al. |
| 6,743,215 B2 | 6/2004 | Bernabei |
| 6,764,493 B1 | 7/2004 | Weber et al. |
| 6,780,426 B2 | 8/2004 | Zhang et al. |
| D496,101 S | 9/2004 | Davison |
| 6,800,083 B2 | 10/2004 | Hiblar et al. |
| 6,800,849 B2 | 10/2004 | Staats |
| D499,207 S | 11/2004 | Angeletta |
| D499,841 S | 12/2004 | Angeletta |
| D502,288 S | 2/2005 | Longoria |
| D502,289 S | 2/2005 | Longoria |
| D502,569 S | 3/2005 | Longoria |
| 6,869,611 B1 | 3/2005 | Kligman et al. |
| 6,878,144 B2 | 4/2005 | Altshuler et al. |
| 6,887,260 B1 | 5/2005 | McDaniel |
| 6,905,487 B2 | 6/2005 | Zimmerman |
| 6,911,031 B2 | 6/2005 | Muldner |

(56) References Cited

U.S. PATENT DOCUMENTS

| | | |
|---|---|---|
| 6,926,681 B1 | 8/2005 | Ramey et al. |
| 6,938,805 B2 | 9/2005 | Brincat |
| 6,942,649 B2 | 9/2005 | Ignon et al. |
| 6,960,206 B2 | 11/2005 | Keane |
| 6,980,448 B2 | 12/2005 | Foss et al. |
| 7,001,355 B2 | 2/2006 | Nunomura et al. |
| 7,004,933 B2 | 2/2006 | McDaniel |
| D517,699 S | 3/2006 | Lansohn |
| 7,031,805 B2 | 4/2006 | Lee et al. |
| 7,044,938 B2 | 5/2006 | La Bianco et al. |
| 7,051,907 B2 | 5/2006 | Brincat |
| 7,052,503 B2 | 5/2006 | Bernabei |
| D522,360 S | 6/2006 | Caserta et al. |
| 7,062,317 B2 | 6/2006 | Avrahami et al. |
| 7,069,073 B2 | 6/2006 | Henley et al. |
| 7,070,488 B2 | 7/2006 | Suissa et al. |
| 7,083,580 B2 | 8/2006 | Bernabei |
| 7,087,036 B2 | 8/2006 | Busby et al. |
| 7,087,063 B2 | 8/2006 | Carson et al. |
| 7,094,252 B2 | 8/2006 | Koop |
| 7,108,689 B2 | 9/2006 | Eckhouse et al. |
| 7,115,275 B2 | 10/2006 | Clarot et al. |
| 7,118,563 B2 | 10/2006 | Weckwerth et al. |
| 7,122,029 B2 | 10/2006 | Koop et al. |
| 7,135,011 B2 | 11/2006 | Powers et al. |
| D533,962 S | 12/2006 | Angeletta |
| 7,153,311 B2 | 12/2006 | Chung |
| 7,166,086 B2 | 1/2007 | Haider et al. |
| D536,481 S | 2/2007 | Angeletta |
| 7,172,572 B2 | 2/2007 | Diamond et al. |
| 7,189,230 B2 | 3/2007 | Knowlton |
| 7,197,359 B1 | 3/2007 | Tokudome et al. |
| 7,198,623 B2 | 4/2007 | Fischer et al. |
| 7,201,765 B2 | 4/2007 | McDaniel |
| D545,207 S | 6/2007 | De Baschmakoff |
| 7,232,431 B1 | 6/2007 | Weimann |
| 7,232,444 B2 | 6/2007 | Chang |
| 7,241,208 B2 | 7/2007 | Suissa et al. |
| 7,250,045 B2 | 7/2007 | Island et al. |
| D548,341 S | 8/2007 | Ohta et al. |
| D548,843 S | 8/2007 | Kertz |
| D553,005 S | 10/2007 | Py et al. |
| 7,276,051 B1 | 10/2007 | Henley et al. |
| 7,293,930 B2 | 11/2007 | Chuang |
| D557,611 S | 12/2007 | Ingemarsson |
| 7,314,326 B2 | 1/2008 | Rosenberg |
| 7,316,657 B2 | 1/2008 | Kleinhenz et al. |
| 7,316,671 B2 | 1/2008 | Lastovich et al. |
| 7,318,828 B1 | 1/2008 | Revivo |
| 7,320,691 B2 | 1/2008 | Pilcher et al. |
| 7,320,801 B2 | 1/2008 | Kelly |
| 7,326,199 B2 | 2/2008 | MacFarland et al. |
| 7,329,252 B1 | 2/2008 | Yamazaki et al. |
| 7,354,423 B2 | 4/2008 | Zelickson et al. |
| 7,364,565 B2 | 4/2008 | Freeman |
| D568,473 S | 5/2008 | Ashiwa et al. |
| 7,367,981 B2 | 5/2008 | Bernaz |
| 7,384,405 B2 | 6/2008 | Rhoades |
| 7,422,567 B2 | 9/2008 | Lastovich et al. |
| 7,427,273 B2 | 9/2008 | Mitsui |
| 7,440,798 B2 | 10/2008 | Redding, Jr. |
| 7,458,944 B2 | 12/2008 | Liste et al. |
| D584,151 S | 1/2009 | Murphy |
| 7,476,205 B2 | 1/2009 | Erdmann |
| 7,477,938 B2 | 1/2009 | Sun et al. |
| 7,482,314 B2 | 1/2009 | Grimes et al. |
| 7,485,125 B2 | 2/2009 | Sjostrom |
| 7,489,989 B2 | 2/2009 | Sukhanov et al. |
| 7,494,503 B2 | 2/2009 | McDaniel |
| 7,507,228 B2 | 3/2009 | Sun et al. |
| 7,572,238 B2 | 8/2009 | Rhoades |
| 7,582,067 B2 | 9/2009 | Van Acker |
| 7,597,900 B2 | 10/2009 | Zimmer et al. |
| 7,597,901 B2 | 10/2009 | Clarot et al. |
| 7,607,972 B2 | 10/2009 | Groman |
| 7,658,742 B2 | 2/2010 | Karasluk |
| 7,678,120 B2 | 3/2010 | Shadduck |
| 7,730,979 B2 | 6/2010 | Kahrig |
| 7,731,570 B2 | 6/2010 | Groman |
| 7,740,651 B2 | 6/2010 | Barak et al. |
| 7,744,582 B2 | 6/2010 | Sadowski et al. |
| 7,749,260 B2 | 7/2010 | Da Silva et al. |
| 7,758,537 B1 | 7/2010 | Brunell et al. |
| 7,771,374 B2 | 8/2010 | Slatkine |
| 7,780,652 B2 | 8/2010 | MacFarland et al. |
| 7,789,886 B2 | 9/2010 | Shadduck |
| D625,198 S | 10/2010 | Hall |
| 7,814,915 B2 | 10/2010 | Davenport et al. |
| 7,837,695 B2 | 11/2010 | Hart et al. |
| 7,857,806 B2 | 12/2010 | Karpowicz et al. |
| 7,862,564 B2 | 1/2011 | Goble |
| 7,901,373 B2 | 3/2011 | Tavger |
| 7,927,188 B2 | 4/2011 | Groman |
| 7,951,156 B2 | 5/2011 | Karasluk |
| D639,164 S | 6/2011 | Walsh |
| 7,981,111 B2 | 7/2011 | Grove et al. |
| 7,981,112 B1 | 7/2011 | Neev |
| 7,993,333 B2 | 8/2011 | Oral et al. |
| 8,025,669 B1 | 9/2011 | David et al. |
| RE42,960 E | 11/2011 | Waldron |
| 8,048,064 B2 | 11/2011 | Hwang et al. |
| 8,048,089 B2 | 11/2011 | Ignon et al. |
| 8,066,716 B2 | 11/2011 | Shadduck |
| 8,088,085 B2 | 1/2012 | Thiebaut et al. |
| 8,105,295 B2 | 1/2012 | Blott et al. |
| 8,128,638 B2 | 3/2012 | Karasiuk et al. |
| 8,135,475 B2 | 3/2012 | Kreindel et al. |
| 8,182,473 B2 | 5/2012 | Altshuler et al. |
| D664,254 S | 7/2012 | Yokoyama et al. |
| 8,221,437 B2 | 7/2012 | Waldron et al. |
| 8,226,663 B2 | 7/2012 | Remsburg et al. |
| 8,231,292 B2 | 7/2012 | Rabe et al. |
| 8,236,008 B2 | 8/2012 | Boone, III et al. |
| 8,236,036 B1 | 8/2012 | Frost |
| 8,241,094 B2 | 8/2012 | Groman |
| 8,273,080 B2 | 9/2012 | Mehta |
| 8,276,592 B2 | 10/2012 | Davenport et al. |
| 8,277,287 B2 | 10/2012 | Hart |
| 8,282,630 B2 | 10/2012 | Neev |
| 8,313,480 B2 | 11/2012 | Neev |
| 8,317,781 B2 | 11/2012 | Owens et al. |
| 8,323,253 B2 | 12/2012 | Hantash et al. |
| 8,337,513 B2 | 12/2012 | Shadduck |
| 8,343,116 B2 | 1/2013 | Ignon et al. |
| 8,360,826 B2 | 1/2013 | Groman |
| D676,764 S | 2/2013 | Moore et al. |
| D678,783 S | 3/2013 | Wilcox et al. |
| 8,398,621 B2 | 3/2013 | Beerwerth et al. |
| D680,437 S | 4/2013 | Bartolo et al. |
| 8,430,104 B2 | 4/2013 | Hennings et al. |
| 8,435,234 B2 | 5/2013 | Chan et al. |
| 8,475,507 B2 | 7/2013 | Dewey et al. |
| 8,478,396 B2 | 7/2013 | Tsao et al. |
| 8,480,721 B2 | 7/2013 | Owens et al. |
| 8,496,654 B2 | 7/2013 | Adanny et al. |
| 8,496,695 B2 | 7/2013 | Kang et al. |
| 8,535,299 B2 | 9/2013 | Giovannoli |
| 8,545,419 B2 | 10/2013 | Kim |
| 8,545,489 B2 | 10/2013 | Giovannoli |
| 8,551,104 B2 | 10/2013 | Weckwerth et al. |
| 8,562,626 B2 | 10/2013 | Sabir et al. |
| 8,573,874 B2 | 11/2013 | Neuner |
| 8,579,916 B2 | 11/2013 | Cheney |
| 8,597,284 B2 | 12/2013 | Castro |
| D697,404 S | 1/2014 | Johnson et al. |
| 8,632,378 B2 | 1/2014 | Groman |
| D699,367 S | 2/2014 | Lee et al. |
| 8,656,931 B2 | 2/2014 | Davenport et al. |
| 8,668,552 B2 | 3/2014 | Groman |
| 8,679,039 B2 | 3/2014 | Tieu et al. |
| 8,700,176 B2 | 4/2014 | Azar et al. |
| 8,702,691 B2 | 4/2014 | Weber et al. |
| 8,702,771 B1 | 4/2014 | Frost |
| 8,721,662 B2 | 5/2014 | Karasluk |

(56) References Cited

U.S. PATENT DOCUMENTS

| | | |
|---|---|---|
| 8,728,064 B2 | 5/2014 | Schomacker et al. |
| 8,740,917 B2 | 6/2014 | Pilcher et al. |
| D709,617 S | 7/2014 | Iliesco de Grimaldi et al. |
| 8,814,836 B2 | 8/2014 | Ignon et al. |
| 8,818,500 B2 | 8/2014 | Duquet et al. |
| 8,821,940 B2 | 9/2014 | Harris et al. |
| 8,834,933 B2 | 9/2014 | Harris et al. |
| 8,858,570 B2 | 10/2014 | Chang |
| 8,939,669 B2 | 1/2015 | Le et al. |
| D722,172 S | 2/2015 | Amemiya et al. |
| 8,945,104 B2 | 2/2015 | Boone, III et al. |
| 8,945,109 B2 | 2/2015 | Mehta |
| 8,974,442 B1 | 3/2015 | Boss, Jr. |
| 9,017,391 B2 | 4/2015 | McDaniel |
| 9,017,392 B2 | 4/2015 | Owens et al. |
| 9,044,582 B2 | 6/2015 | Chang et al. |
| 9,050,133 B1 | 6/2015 | Boone, III et al. |
| 9,050,156 B2 | 6/2015 | Groman |
| 9,056,193 B2 | 6/2015 | Ignon et al. |
| D734,154 S | 7/2015 | Johnson et al. |
| 9,072,521 B2 | 7/2015 | Levi et al. |
| 9,072,533 B2 | 7/2015 | Liu et al. |
| 9,072,892 B2 | 7/2015 | Owens et al. |
| 9,084,587 B2 | 7/2015 | Eckhouse et al. |
| 9,149,322 B2 | 10/2015 | Knowlton |
| D743,269 S | 11/2015 | Pape |
| D743,558 S | 11/2015 | Kim et al. |
| 9,186,490 B2 | 11/2015 | Chang et al. |
| 9,227,044 B2 | 1/2016 | Bansal et al. |
| 9,227,082 B2 | 1/2016 | McDaniel |
| 9,233,207 B2 | 1/2016 | Polyakov et al. |
| 9,271,755 B2 | 3/2016 | Luzon et al. |
| 9,278,230 B2 | 3/2016 | Levin et al. |
| 9,283,037 B2 | 3/2016 | Bragagna et al. |
| 9,314,302 B2 | 4/2016 | Dougal |
| 9,351,792 B2 | 5/2016 | Manstein et al. |
| 9,351,794 B2 | 5/2016 | Suckewer et al. |
| 9,375,281 B2 | 6/2016 | Moench et al. |
| 9,421,260 B2 | 8/2016 | Harris et al. |
| 9,421,261 B2 | 8/2016 | Harris et al. |
| D765,512 S | 9/2016 | Joulia |
| 9,439,964 B2 | 9/2016 | Harris et al. |
| 9,440,093 B2 | 9/2016 | Homer |
| 9,452,013 B2 | 9/2016 | Manstein |
| 9,468,464 B2 | 10/2016 | Shadduck |
| 9,474,886 B2 | 10/2016 | Ignon et al. |
| D772,481 S | 11/2016 | Paquet |
| 9,480,836 B2 | 11/2016 | Na |
| 9,486,615 B2 | 11/2016 | Ignon et al. |
| 9,498,610 B2 | 11/2016 | Ignon et al. |
| 9,517,085 B2 | 12/2016 | Karasiuk |
| 9,522,287 B2 | 12/2016 | Owens et al. |
| 9,550,052 B2 | 1/2017 | Ignon et al. |
| 9,566,088 B2 | 2/2017 | Ignon et al. |
| 9,566,454 B2 | 2/2017 | Barthe et al. |
| 9,572,880 B2 | 2/2017 | Harris et al. |
| 9,597,527 B2 | 3/2017 | Buchholz et al. |
| 2,782,881 A1 | 4/2017 | Seiders et al. |
| D787,054 S | 5/2017 | Rini et al. |
| 9,636,521 B2 | 5/2017 | Isserow et al. |
| 9,636,522 B2 | 5/2017 | Oversluizen et al. |
| 9,642,997 B2 | 5/2017 | Ignon et al. |
| 9,662,482 B2 | 5/2017 | Ignon et al. |
| 9,669,233 B2 | 6/2017 | Quisenberry et al. |
| 9,675,817 B2 | 6/2017 | Isserow et al. |
| 9,694,199 B2 | 7/2017 | Duquet et al. |
| 9,700,684 B2 | 7/2017 | Vlodaver et al. |
| 9,731,053 B2 | 8/2017 | Alai |
| 9,744,315 B1 | 8/2017 | Levi |
| 9,775,645 B2 | 10/2017 | Boone, III |
| 9,775,646 B2 | 10/2017 | Shadduck |
| 9,775,976 B2 | 10/2017 | Grez |
| 9,814,485 B2 | 11/2017 | Pratt et al. |
| 9,814,647 B2 | 11/2017 | Ajiki |
| 9,814,868 B2 | 11/2017 | Ignon et al. |
| 9,814,906 B2 | 11/2017 | McDaniel |
| 9,833,261 B2 | 12/2017 | Boone, III et al. |
| 9,861,442 B2 | 1/2018 | Tankovich et al. |
| D811,225 S | 2/2018 | Newson |
| D811,381 S | 2/2018 | Morohoshi et al. |
| 9,918,727 B1 | 3/2018 | Boone, III et al. |
| 9,949,552 B2 | 4/2018 | Rabe et al. |
| 9,950,147 B2 | 4/2018 | Mehta |
| 9,955,769 B2 | 5/2018 | Rabe et al. |
| 9,962,220 B2 | 5/2018 | Domankevitz |
| 9,968,800 B2 | 5/2018 | Anderson et al. |
| 10,004,919 B2 | 6/2018 | Lemmens et al. |
| D822,845 S | 7/2018 | Shimobayashi et al. |
| 10,010,445 B2 | 7/2018 | Isserow et al. |
| 10,022,289 B2 | 7/2018 | Ajiki et al. |
| 10,035,007 B2 | 7/2018 | Ignon et al. |
| D825,763 S | 8/2018 | Lim et al. |
| 10,052,467 B2 | 8/2018 | Bansal et al. |
| D829,333 S | 9/2018 | Shin et al. |
| 10,076,354 B2 | 9/2018 | Knowlton |
| 10,076,646 B2 | 9/2018 | Casasanta, III et al. |
| 10,080,581 B2 | 9/2018 | Knowlton |
| D829,921 S | 10/2018 | Xiong |
| 10,092,478 B1 | 10/2018 | Amit |
| 10,105,191 B2 | 10/2018 | Blanco et al. |
| D833,283 S | 11/2018 | Rock |
| 10,130,390 B1 | 11/2018 | Hart et al. |
| 10,130,827 B2 | 11/2018 | Buchholz et al. |
| D836,781 S | 12/2018 | Meurer et al. |
| 10,149,969 B2 | 12/2018 | Grez et al. |
| 10,149,984 B2 | 12/2018 | Modi et al. |
| 10,172,644 B2 | 1/2019 | Ignon et al. |
| 10,179,229 B2 | 1/2019 | Gnon et al. |
| 10,183,183 B2 | 1/2019 | Burdette |
| 10,188,193 B2 | 1/2019 | Rabe et al. |
| 10,206,743 B2 | 2/2019 | Tankovich et al. |
| 10,207,034 B2 | 2/2019 | Collins |
| 10,220,122 B2 | 3/2019 | Clark, III et al. |
| 10,238,812 B2 | 3/2019 | Ignon |
| 10,238,849 B2 | 3/2019 | Britva et al. |
| 10,251,675 B2 | 4/2019 | Ignon et al. |
| 10,252,044 B2 | 4/2019 | Bock |
| 10,271,900 B2 | 4/2019 | Marchitto et al. |
| 10,272,258 B2 | 4/2019 | Quisenberry et al. |
| D851,759 S | 6/2019 | Jones et al. |
| 10,307,330 B1 | 6/2019 | Sedic |
| 10,308,378 B2 | 6/2019 | Goodwin et al. |
| 10,314,378 B2 | 6/2019 | Rabe et al. |
| 10,321,948 B2 | 6/2019 | Knowlton |
| 10,322,233 B2 | 6/2019 | Hanson et al. |
| 10,328,277 B2 | 6/2019 | Modi et al. |
| D852,962 S | 7/2019 | Chang |
| 10,335,191 B2 | 7/2019 | Knowlton |
| 10,357,641 B2 | 7/2019 | Ignon et al. |
| 10,357,642 B2 | 7/2019 | Ignon et al. |
| 10,334,933 B2 | 8/2019 | Rosario et al. |
| 10,369,073 B2 | 8/2019 | Rosario et al. |
| 10,413,359 B2 | 9/2019 | Felsenstein et al. |
| D861,913 S | 10/2019 | Stamm et al. |
| 10,456,197 B2 | 10/2019 | Felsenstein et al. |
| 10,456,321 B2 | 10/2019 | Shadduck |
| 10,456,567 B2 | 10/2019 | Streeter |
| D867,587 S | 11/2019 | Holtz |
| 10,463,429 B2 | 11/2019 | Deem et al. |
| 10,471,274 B2 | 11/2019 | Liu et al. |
| 10,485,983 B1 | 11/2019 | Boone, III et al. |
| D868,981 S | 12/2019 | Salamon et al. |
| D873,430 S | 1/2020 | Accolla |
| D873,481 S | 1/2020 | Larkin |
| 10,524,835 B2 | 1/2020 | Shadduck et al. |
| 10,537,304 B2 | 1/2020 | Barthe et al. |
| 10,537,640 B2 | 1/2020 | Harris et al. |
| 10,556,096 B2 | 2/2020 | Ignon et al. |
| 10,556,097 B2 | 2/2020 | Ignon et al. |
| 10,583,037 B2 | 3/2020 | Isserow et al. |
| D886,370 S | 6/2020 | Soutelo Gomes |
| D886,372 S | 6/2020 | Weinrich |
| D887,571 S | 6/2020 | Liu |
| 10,667,985 B2 | 6/2020 | Decaux et al. |

(56) References Cited

U.S. PATENT DOCUMENTS

| | | |
|---|---|---|
| 10,675,481 B1 | 6/2020 | Tankovich |
| 10,688,290 B1 | 6/2020 | Yuval |
| 10,702,328 B2 | 7/2020 | Slatkine et al. |
| 10,716,924 B2 | 7/2020 | Knowlton |
| D893,024 S | 8/2020 | Whiteside |
| 10,736,653 B2 | 8/2020 | Knowlton |
| 10,737,080 B2 | 8/2020 | Patterson |
| 10,758,261 B2 | 9/2020 | Richardson |
| 10,772,658 B2 | 9/2020 | Knowlton |
| 10,792,382 B2 | 10/2020 | Rafko |
| 10,799,285 B2 | 10/2020 | Mulholland |
| 10,799,430 B2 | 10/2020 | Danto |
| 10,813,694 B2 | 10/2020 | Johnson et al. |
| 10,835,287 B2 | 11/2020 | Shadduck et al. |
| 10,835,726 B2 | 11/2020 | Redding, Jr. |
| D903,889 S | 12/2020 | Luo et al. |
| 10,850,095 B2 | 12/2020 | Ebbers et al. |
| 10,856,900 B2 | 12/2020 | Knowlton |
| 10,860,026 B2 | 12/2020 | Nguyen et al. |
| 10,874,579 B1 | 12/2020 | Rembert |
| D908,282 S | 1/2021 | Kim |
| 10,893,907 B2 | 1/2021 | Kim |
| 10,912,428 B2 | 2/2021 | Daffer |
| 10,918,190 B2 | 2/2021 | Laudati |
| 10,946,191 B2 | 3/2021 | Cazares Delgadillo |
| 10,952,811 B2 | 3/2021 | Blanco et al. |
| 10,952,907 B1 | 3/2021 | Carver |
| D917,290 S | 4/2021 | Bravman et al. |
| 10,980,592 B2 | 4/2021 | Horton et al. |
| 10,993,743 B2 | 5/2021 | Ignon et al. |
| 11,020,577 B2 | 6/2021 | Ignon et al. |
| 11,045,661 B2 | 6/2021 | Oversluizen et al. |
| D927,008 S | 8/2021 | Rappaport |
| D928,977 S | 8/2021 | Dijkstra |
| 11,083,515 B2 | 8/2021 | Slatkine et al. |
| 11,123,039 B2 | 9/2021 | Barthe et al. |
| 11,141,761 B2 | 10/2021 | Connelly et al. |
| 11,154,723 B2 | 10/2021 | Lee |
| 11,172,978 B2 | 11/2021 | Wootten et al. |
| 11,202,657 B2 | 12/2021 | Ignon et al. |
| 11,213,321 B2 | 1/2022 | Ignon et al. |
| 11,224,728 B2 | 1/2022 | Ignon et al. |
| 11,241,357 B2 | 2/2022 | Ignon et al. |
| 11,247,039 B2 | 2/2022 | Schwarz |
| 11,278,101 B2 | 3/2022 | Jeannin et al. |
| 11,291,474 B2 | 4/2022 | Nicolas et al. |
| 11,291,498 B2 | 4/2022 | Slatkine et al. |
| 11,311,721 B2 | 4/2022 | Ebbers et al. |
| 11,337,745 B2 | 5/2022 | Kim |
| 11,337,755 B2 | 5/2022 | Hancock et al. |
| 11,351,063 B2 | 6/2022 | Locke et al. |
| 11,419,678 B2 | 8/2022 | Deem et al. |
| D964,581 S | 9/2022 | Guo |
| 11,446,477 B2 | 9/2022 | Ignon et al. |
| 11,452,852 B2 | 9/2022 | Quan et al. |
| 11,452,883 B1 | 9/2022 | Marchese et al. |
| 11,497,553 B2 | 11/2022 | Reinhard et al. |
| 11,504,148 B2 | 11/2022 | Friend |
| 11,517,350 B2 | 12/2022 | Ignon et al. |
| 11,540,882 B2 | 1/2023 | Masotti et al. |
| 11,547,840 B2 | 1/2023 | Ignon et al. |
| D979,782 S | 2/2023 | Sung et al. |
| 11,590,345 B2 | 2/2023 | Danitz et al. |
| 11,602,629 B2 | 3/2023 | Schwarz et al. |
| 11,612,726 B2 | 3/2023 | Ignon et al. |
| D994,134 S | 8/2023 | Lim |
| 11,717,326 B2 | 8/2023 | Ignon et al. |
| D998,143 S | 9/2023 | Nagao et al. |
| 11,744,999 B2 | 9/2023 | Ignon et al. |
| 11,806,495 B2 | 11/2023 | Ignon et al. |
| D1,011,541 S | 1/2024 | Yu |
| 11,865,287 B2 | 1/2024 | Ignon et al. |
| 11,883,621 B2 | 1/2024 | Ignon et al. |
| 11,903,615 B2 | 2/2024 | Ignon et al. |
| D1,016,615 S | 3/2024 | Rozporka et al. |
| 11,925,780 B2 | 3/2024 | Ignon et al. |
| 12,005,217 B2 | 6/2024 | Ignon et al. |
| 2001/0023351 A1 | 9/2001 | Ellers |
| 2001/0037118 A1 | 11/2001 | Shadduck |
| 2001/0049511 A1 | 12/2001 | Coleman et al. |
| 2002/0016601 A1 | 2/2002 | Shadduck |
| 2002/0040199 A1 | 4/2002 | Klopotek |
| 2002/0041891 A1 | 4/2002 | Cheski |
| 2002/0058952 A1 | 5/2002 | Weber et al. |
| 2002/0099356 A1 | 7/2002 | Unger et al. |
| 2002/0107527 A1 | 8/2002 | Burres |
| 2002/0128663 A1 | 9/2002 | Mercier et al. |
| 2002/0133110 A1 | 9/2002 | Citow |
| 2002/0133176 A1 | 9/2002 | Parkin et al. |
| 2002/0151826 A1 | 10/2002 | Ramey et al. |
| 2002/0151908 A1 | 10/2002 | Mallett, Sr. et al. |
| 2002/0162863 A1 | 11/2002 | Brincat |
| 2002/0188261 A1 | 12/2002 | Hruska |
| 2002/0198488 A1 | 12/2002 | Yao |
| 2003/0012415 A1 | 1/2003 | Cossel |
| 2003/0018252 A1 | 1/2003 | Duchon et al. |
| 2003/0060834 A1 | 3/2003 | Muldner |
| 2003/0093040 A1 | 5/2003 | Mikszta et al. |
| 2003/0093089 A1 | 5/2003 | Greenberg |
| 2003/0097139 A1 | 5/2003 | Karasiuk |
| 2003/0135388 A1 | 7/2003 | Martucci et al. |
| 2003/0167032 A1 | 9/2003 | Ignon et al. |
| 2003/0187462 A1 | 10/2003 | Chang |
| 2003/0208159 A1 | 11/2003 | Ignon et al. |
| 2003/0212127 A1 | 11/2003 | Glassman et al. |
| 2003/0212415 A1 | 11/2003 | Karasiuk |
| 2004/0005349 A1 | 1/2004 | Neev |
| 2004/0010222 A1 | 1/2004 | Nunomura et al. |
| 2004/0010269 A1 | 1/2004 | Grimes et al. |
| 2004/0015139 A1 | 1/2004 | La Bianco |
| 2004/0051368 A1 | 3/2004 | Caputo et al. |
| 2004/0087972 A1 | 5/2004 | Mulholland et al. |
| 2004/0092895 A1 | 5/2004 | Harmon |
| 2004/0092959 A1 | 5/2004 | Bernaz |
| 2004/0097967 A1 | 5/2004 | Ignon |
| 2004/0122447 A1 | 6/2004 | Harmon et al. |
| 2004/0127914 A1 | 7/2004 | Chung |
| 2004/0138680 A1 | 7/2004 | Twitchell et al. |
| 2004/0138726 A1 | 7/2004 | Savage, Jr. et al. |
| 2004/0143274 A1 | 7/2004 | Shadduck |
| 2004/0162565 A1 | 8/2004 | Carson et al. |
| 2004/0166172 A1 | 8/2004 | Rosati et al. |
| 2004/0176823 A1 | 9/2004 | Island et al. |
| 2004/0210167 A1 | 10/2004 | Webster |
| 2004/0210280 A1 | 10/2004 | Liedtke |
| 2004/0219179 A1 | 11/2004 | McDaniel |
| 2004/0229295 A1 | 11/2004 | Marchitto et al. |
| 2004/0236291 A1 | 11/2004 | Zelickson et al. |
| 2004/0236375 A1 | 11/2004 | Redding, Jr. |
| 2004/0243149 A1 | 12/2004 | Lee, Jr. |
| 2004/0254587 A1 | 12/2004 | Park |
| 2004/0267285 A1 | 12/2004 | Chang |
| 2005/0015077 A1 | 1/2005 | Kuklin et al. |
| 2005/0037034 A1 | 2/2005 | Rhoades |
| 2005/0038377 A1 | 2/2005 | Redding, Jr. |
| 2005/0038448 A1 | 2/2005 | Chung |
| 2005/0059940 A1 | 3/2005 | Weber et al. |
| 2005/0065461 A1 | 3/2005 | Redding, Jr. |
| 2005/0070977 A1 | 3/2005 | Molina |
| 2005/0075599 A1 | 4/2005 | Redding, Jr. |
| 2005/0080465 A1 | 4/2005 | Zelickson et al. |
| 2005/0084509 A1 | 4/2005 | Bernstein |
| 2005/0148958 A1 | 7/2005 | Rucinski |
| 2005/0154333 A1 | 7/2005 | Mulholland et al. |
| 2005/0203111 A1 | 9/2005 | David |
| 2005/0203593 A1 | 9/2005 | Shanks et al. |
| 2005/0209611 A1 | 9/2005 | Greenberg |
| 2005/0245180 A1 | 11/2005 | Suissa et al. |
| 2005/0283176 A1 | 12/2005 | Law |
| 2006/0002960 A1 | 1/2006 | Zoeteweij et al. |
| 2006/0015059 A1 | 1/2006 | Redding, Jr. |
| 2006/0058714 A1 | 3/2006 | Rhoades |
| 2006/0100567 A1 | 5/2006 | Marchitto et al. |
| 2006/0116674 A1 | 6/2006 | Goble et al. |

(56) References Cited

U.S. PATENT DOCUMENTS

| | | |
|---|---|---|
| 2006/0161178 A1 | 7/2006 | Lee |
| 2006/0184071 A1 | 8/2006 | Klopotek |
| 2006/0189964 A1 | 8/2006 | Anderson |
| 2006/0191562 A1 | 8/2006 | Numomura |
| 2006/0200099 A1 | 9/2006 | La Bianco et al. |
| 2006/0200172 A1 | 9/2006 | Shadduck |
| 2006/0200173 A1 | 9/2006 | Shadduck |
| 2006/0200213 A1 | 9/2006 | McDaniel |
| 2006/0212025 A1 | 9/2006 | McDaniel |
| 2006/0212029 A1 | 9/2006 | Villacampa et al. |
| 2006/0222445 A1 | 10/2006 | Chuang |
| 2006/0235371 A1 | 10/2006 | Wakamatsu et al. |
| 2006/0253078 A1 | 11/2006 | Wu et al. |
| 2006/0253079 A1 | 11/2006 | McDonough et al. |
| 2006/0253125 A1 | 11/2006 | Ignon |
| 2006/0264893 A1 | 11/2006 | Sage, Jr. et al. |
| 2006/0264926 A1 | 11/2006 | Kochamba |
| 2006/0269580 A1 | 11/2006 | Cole et al. |
| 2006/0278661 A1 | 12/2006 | Cooper et al. |
| 2007/0005078 A1 | 1/2007 | Hart et al. |
| 2007/0020321 A1 | 1/2007 | Redding et al. |
| 2007/0027411 A1 | 2/2007 | Ella et al. |
| 2007/0043382 A1 | 2/2007 | Cheney |
| 2007/0049901 A1 | 3/2007 | Wu et al. |
| 2007/0065515 A1 | 3/2007 | Key |
| 2007/0073327 A1 | 3/2007 | Giovannoli |
| 2007/0078290 A1 | 4/2007 | Esenaliev |
| 2007/0088245 A1 | 4/2007 | Babaev et al. |
| 2007/0088371 A1 | 4/2007 | Karasluk |
| 2007/0093694 A1 | 4/2007 | Fassullotis et al. |
| 2007/0123808 A1 | 5/2007 | Rhoades |
| 2007/0139630 A1 | 6/2007 | Kleman et al. |
| 2007/0149991 A1 | 6/2007 | Mulholland |
| 2007/0154502 A1 | 7/2007 | Hattendorf et al. |
| 2007/0156124 A1 | 7/2007 | Ignon et al. |
| 2007/0178121 A1 | 8/2007 | First et al. |
| 2007/0198031 A1 | 8/2007 | Kellogg |
| 2007/0208353 A1 | 9/2007 | Shadduck |
| 2007/0232987 A1 | 10/2007 | Diaz et al. |
| 2007/0239079 A1 | 10/2007 | Manstein et al. |
| 2007/0239173 A1 | 10/2007 | Khalaj |
| 2007/0255355 A1 | 11/2007 | Altshuler et al. |
| 2007/0264625 A1 | 11/2007 | DeBenedictis et al. |
| 2007/0270738 A1 | 11/2007 | Wu et al. |
| 2008/0009802 A1 | 1/2008 | Lambino et al. |
| 2008/0015555 A1 | 1/2008 | Manstein et al. |
| 2008/0027328 A1 | 1/2008 | Klopotek et al. |
| 2008/0027518 A1 | 1/2008 | Island et al. |
| 2008/0091126 A1 | 4/2008 | Greenburg |
| 2008/0091179 A1 | 4/2008 | Durkin et al. |
| 2008/0103563 A1 | 5/2008 | Powell |
| 2008/0119781 A1 | 5/2008 | King |
| 2008/0132914 A1 | 6/2008 | Bossard et al. |
| 2008/0139974 A1 | 6/2008 | Da Silva |
| 2008/0146970 A1 | 6/2008 | Litman et al. |
| 2008/0154161 A1 | 6/2008 | Abbott |
| 2008/0154183 A1 | 6/2008 | Baker et al. |
| 2008/0161799 A1 | 7/2008 | Stangenes et al. |
| 2008/0188840 A1 | 8/2008 | Johnson et al. |
| 2008/0193493 A1 | 8/2008 | Rhoades |
| 2008/0200861 A1 | 8/2008 | Shalev et al. |
| 2008/0200863 A1 | 8/2008 | Chomas et al. |
| 2008/0208146 A1 | 8/2008 | Brandwein et al. |
| 2008/0208179 A1 | 8/2008 | Chan et al. |
| 2008/0214987 A1 | 9/2008 | Xu |
| 2008/0215068 A1 | 9/2008 | Hart et al. |
| 2008/0221548 A1 | 9/2008 | Danenberg et al. |
| 2008/0234626 A1 | 9/2008 | Chelak |
| 2008/0243039 A1 | 10/2008 | Rhoades |
| 2008/0287864 A1 | 11/2008 | Rosenberg |
| 2008/0300529 A1 | 12/2008 | Reinstein |
| 2008/0300552 A1 | 12/2008 | Cichocki et al. |
| 2009/0048557 A1 | 2/2009 | Yeshurun et al. |
| 2009/0053390 A1 | 2/2009 | Sakou et al. |
| 2009/0062815 A1 | 3/2009 | Karasluk et al. |
| 2009/0099091 A1 | 4/2009 | Hantash |
| 2009/0099093 A1 | 4/2009 | Hantash |
| 2009/0118684 A1 | 5/2009 | Da Silva et al. |
| 2009/0124985 A1 | 5/2009 | Hasenoehrl et al. |
| 2009/0132012 A1 | 5/2009 | Shanks |
| 2009/0138026 A1 | 5/2009 | Wu |
| 2009/0171191 A1 | 7/2009 | Patrick et al. |
| 2009/0171194 A1 | 7/2009 | Patrick et al. |
| 2009/0177171 A1 | 7/2009 | Gnon et al. |
| 2009/0192442 A1 | 7/2009 | Ignon et al. |
| 2009/0222023 A1 | 9/2009 | Boone, III et al. |
| 2009/0254014 A1 | 10/2009 | Son |
| 2009/0299237 A1 | 12/2009 | Rhoades |
| 2010/0023003 A1 | 1/2010 | Mulholland |
| 2010/0036298 A1 | 2/2010 | Fuster |
| 2010/0045427 A1 | 2/2010 | Boone, III et al. |
| 2010/0048980 A1 | 2/2010 | De Jong et al. |
| 2010/0049177 A1 | 2/2010 | Boone, III et al. |
| 2010/0049210 A1 | 2/2010 | Boone, III et al. |
| 2010/0056847 A1 | 3/2010 | De Jong et al. |
| 2010/0063565 A1 | 3/2010 | Beerwerth et al. |
| 2010/0217357 A1 | 8/2010 | Da Silva |
| 2010/0305495 A1 | 12/2010 | Anderson et al. |
| 2011/0054490 A1 | 3/2011 | Hart |
| 2011/0060270 A1 | 3/2011 | Eppstein |
| 2011/0066162 A1 | 3/2011 | Cohen |
| 2011/0082415 A1 | 4/2011 | Ignon et al. |
| 2011/0067761 A1 | 6/2011 | King |
| 2011/0144410 A1 | 6/2011 | Kennedy |
| 2011/0190726 A1 | 8/2011 | Hantash et al. |
| 2011/0251523 A1 | 10/2011 | Kim |
| 2011/0264028 A1 | 10/2011 | Ramdas et al. |
| 2011/0270137 A1 | 11/2011 | Goren et al. |
| 2011/0270364 A1 | 11/2011 | Kreindel et al. |
| 2011/0295273 A1 | 12/2011 | Waldron et al. |
| 2012/0022435 A1 | 1/2012 | Ignon et al. |
| 2012/0041338 A1 | 2/2012 | Chickering, III et al. |
| 2012/0041523 A1 | 2/2012 | Solomon et al. |
| 2012/0109041 A1 | 5/2012 | Munz |
| 2012/0109043 A1 | 5/2012 | Zhou et al. |
| 2012/0136374 A1 | 5/2012 | Karasiuk |
| 2012/0171636 A1 | 7/2012 | Gromar |
| 2012/0259252 A1 | 10/2012 | Thorn-Leeson et al. |
| 2012/0289885 A1 | 11/2012 | Cottrell |
| 2012/0302929 A1 | 11/2012 | Tkachenko |
| 2013/0004230 A1 | 1/2013 | Kirk, III et al. |
| 2013/0018317 A1 | 1/2013 | Bobroff et al. |
| 2013/0066336 A1 | 3/2013 | Boone, III et al. |
| 2013/0085421 A1 | 4/2013 | Gillespie et al. |
| 2013/0096546 A1 | 4/2013 | Mirkov et al. |
| 2013/0096577 A1 | 4/2013 | Shadduck |
| 2013/0102978 A1 | 4/2013 | Ignon et al. |
| 2013/0144207 A1 | 6/2013 | Gonon |
| 2013/0144280 A1 | 6/2013 | Eckhouse et al. |
| 2013/0158547 A1 | 6/2013 | David |
| 2013/0204238 A1 | 8/2013 | Lederman et al. |
| 2013/0226075 A1 | 8/2013 | Hennings et al. |
| 2013/0226269 A1 | 8/2013 | Eckhouse et al. |
| 2013/0261534 A1 | 10/2013 | Niezgoda et al. |
| 2013/0268032 A1 | 10/2013 | Neev |
| 2013/0296807 A1 | 11/2013 | Lintern et al. |
| 2013/0310906 A1 | 11/2013 | Neev |
| 2013/0317314 A1 | 11/2013 | Lampson |
| 2013/0345616 A1 | 12/2013 | Chang |
| 2014/0031801 A1 | 1/2014 | Giovannoli |
| 2014/0079686 A1 | 3/2014 | Barman et al. |
| 2014/0081251 A1 | 3/2014 | Giovannoli |
| 2014/0094718 A1 | 4/2014 | Feldman |
| 2014/0114234 A1 | 4/2014 | Redding, Jr. |
| 2014/0135798 A1 | 5/2014 | David |
| 2014/0234004 A1 | 8/2014 | Thorpe et al. |
| 2014/0243589 A1 | 8/2014 | Rowan |
| 2014/0316492 A1 | 10/2014 | Min et al. |
| 2014/0343481 A1 | 11/2014 | Ignon |
| 2014/0343574 A1 | 11/2014 | Ignon et al. |
| 2014/0378887 A1 | 12/2014 | Chang et al. |
| 2015/0032047 A1 | 1/2015 | Ignon et al. |
| 2015/0039060 A1 | 2/2015 | Paulussen et al. |
| 2015/0141877 A1 | 5/2015 | Feldman |

(56) References Cited

U.S. PATENT DOCUMENTS

| | | |
|---|---|---|
| 2015/0157496 A1 | 6/2015 | Horton et al. |
| 2015/0202007 A1 | 7/2015 | Mainstein et al. |
| 2015/0230824 A1 | 8/2015 | Shadduck |
| 2015/0230825 A1 | 8/2015 | Shadduck |
| 2015/0231379 A1 | 8/2015 | Ignon et al. |
| 2015/0265822 A1 | 9/2015 | Ignon et al. |
| 2015/0272623 A1 | 10/2015 | Ignon et al. |
| 2015/0290442 A1 | 10/2015 | Ignon et al. |
| 2015/0313993 A1 | 11/2015 | Bock |
| 2015/0351868 A1 | 12/2015 | Groman |
| 2016/0015962 A1 | 1/2016 | Maragheh et al. |
| 2016/0018100 A1 | 1/2016 | Batt et al. |
| 2016/0038183 A1 | 2/2016 | Ignon et al. |
| 2016/0089525 A1 | 3/2016 | Grez et al. |
| 2016/0175609 A1 | 6/2016 | Dye et al. |
| 2016/0220849 A1 | 8/2016 | Knowlton |
| 2016/0235257 A1 | 8/2016 | Daffer |
| 2016/0250415 A1 | 9/2016 | Yagi et al. |
| 2016/0256671 A1 | 9/2016 | Ignon et al. |
| 2016/0270850 A1 | 9/2016 | Manstein et al. |
| 2016/0270851 A1 | 9/2016 | Moench et al. |
| 2016/0287333 A1 | 10/2016 | Morrison |
| 2016/0324578 A1 | 11/2016 | Manstein et al. |
| 2017/0036002 A1 | 2/2017 | Ignon et al. |
| 2017/0043150 A1 | 2/2017 | Kim |
| 2017/0065801 A1 | 3/2017 | Ignon et al. |
| 2017/0065829 A1 | 3/2017 | Ku |
| 2017/0106206 A1 | 4/2017 | Seckel |
| 2017/0128319 A1 | 5/2017 | Decaux et al. |
| 2017/0157419 A1 | 6/2017 | Jeong |
| 2017/0196759 A1 | 7/2017 | Palomaki et al. |
| 2017/0209894 A1 | 7/2017 | Sporrer |
| 2017/0252105 A1 | 9/2017 | Deem et al. |
| 2017/0291007 A1 | 10/2017 | Dubey et al. |
| 2017/0340356 A1 | 11/2017 | Presser et al. |
| 2017/0343308 A1 | 11/2017 | Wojciechowski, III et al. |
| 2018/0008500 A1 | 1/2018 | Anderson et al. |
| 2018/0140329 A1 | 5/2018 | Beljens et al. |
| 2018/0185675 A1 | 7/2018 | Kern et al. |
| 2018/0310979 A1 | 11/2018 | Peled et al. |
| 2018/0318568 A1 | 11/2018 | Ignon et al. |
| 2018/0326191 A1 | 11/2018 | Bansal et al. |
| 2019/0009110 A1 | 1/2019 | Gross et al. |
| 2019/0009111 A1 | 1/2019 | Myhr et al. |
| 2019/0070069 A1 | 3/2019 | Gertner et al. |
| 2019/0076193 A1 | 3/2019 | Clementi et al. |
| 2019/0083161 A1 | 3/2019 | Harle et al. |
| 2019/0133642 A1 | 5/2019 | Ignon et al. |
| 2019/0143089 A1 | 5/2019 | Ignon et al. |
| 2019/0151637 A1 | 5/2019 | Groop et al. |
| 2019/0168016 A1 | 6/2019 | Anderson et al. |
| 2019/0183562 A1 | 6/2019 | Widgerow |
| 2019/0209859 A1 | 7/2019 | Quisenberry et al. |
| 2019/0223914 A1 | 7/2019 | Ignon et al. |
| 2019/0224501 A1 | 7/2019 | Burdette |
| 2019/0239939 A1 | 8/2019 | Boll et al. |
| 2019/0240110 A1 | 8/2019 | Sedic |
| 2019/0240502 A1 | 8/2019 | Anderson et al. |
| 2019/0257320 A1 | 8/2019 | Petit et al. |
| 2019/0274759 A1 | 9/2019 | Royon et al. |
| 2019/0275320 A1 | 9/2019 | Kim et al. |
| 2019/0336740 A1 | 11/2019 | Ignon et al. |
| 2019/0366067 A1 | 12/2019 | Ginggen et al. |
| 2020/0009007 A1 | 1/2020 | Shadduck |
| 2020/0016342 A1 | 1/2020 | Ignon |
| 2020/0030627 A1 | 1/2020 | Eltorai et al. |
| 2020/0093945 A1 | 3/2020 | Jeong |
| 2020/0101312 A1 | 4/2020 | Pai et al. |
| 2020/0114116 A1 | 4/2020 | Dubey et al. |
| 2020/0121354 A1 | 4/2020 | Ginggen et al. |
| 2020/0171288 A1 | 6/2020 | Ignon et al. |
| 2020/0171289 A1 | 6/2020 | Ignon et al. |
| 2020/0179220 A1 | 6/2020 | Jablow |
| 2020/0206072 A1 | 7/2020 | Capelli et al. |
| 2020/0254273 A1 | 8/2020 | Jafari et al. |
| 2020/0275945 A1 | 9/2020 | Knowlton |
| 2020/0288843 A1 | 9/2020 | Verheem |
| 2020/0289161 A1 | 9/2020 | Scooros |
| 2020/0306555 A1 | 10/2020 | Ebbesson |
| 2020/0316270 A1 | 10/2020 | Dijkstra et al. |
| 2020/0330754 A1 | 10/2020 | Kim et al. |
| 2020/0338586 A1 | 10/2020 | Park |
| 2020/0367961 A1 | 11/2020 | Podmore et al. |
| 2020/0390468 A1 | 12/2020 | Alexander |
| 2021/0001148 A1 | 1/2021 | Verheem |
| 2021/0052292 A1 | 2/2021 | Karni |
| 2021/0085367 A1 | 3/2021 | Shadduck et al. |
| 2021/0128416 A1 | 5/2021 | Danto |
| 2021/0145479 A1 | 5/2021 | Ignon et al. |
| 2021/0145480 A1 | 5/2021 | Ignon et al. |
| 2021/0145481 A1 | 5/2021 | Ignon et al. |
| 2021/0154093 A1 | 5/2021 | Boone, III et al. |
| 2021/0154453 A1 | 5/2021 | Ignon et al. |
| 2021/0154454 A1 | 5/2021 | Ignon et al. |
| 2021/0154455 A1 | 5/2021 | Ignon et al. |
| 2021/0170150 A1 | 6/2021 | Hong et al. |
| 2021/0177463 A1 | 6/2021 | Ignon et al. |
| 2021/0204982 A1 | 7/2021 | Nicolas et al. |
| 2021/0220631 A1 | 7/2021 | Ok et al. |
| 2021/0236342 A1 | 8/2021 | Long et al. |
| 2021/0236347 A1 | 8/2021 | Carver |
| 2021/0236836 A1 | 8/2021 | Schwarz et al. |
| 2021/0242657 A1 | 8/2021 | Yi et al. |
| 2021/0259914 A1 | 8/2021 | Holbert |
| 2021/0267625 A1 | 9/2021 | Carver |
| 2021/0268304 A1 | 9/2021 | Lee |
| 2021/0275406 A1 | 9/2021 | Danto |
| 2021/0282855 A1 | 9/2021 | Boinagrov et al. |
| 2021/0283421 A1 | 9/2021 | Kang et al. |
| 2021/0290430 A1 | 9/2021 | Kim |
| 2021/0330356 A1 | 10/2021 | Del Rosario et al. |
| 2021/0353922 A1 | 11/2021 | Ignon et al. |
| 2021/0361525 A1 | 11/2021 | Park et al. |
| 2021/0370049 A1 | 12/2021 | Moss et al. |
| 2021/0370089 A1 | 12/2021 | Anash |
| 2021/0393478 A1 | 12/2021 | Bhatt |
| 2021/0393974 A1 | 12/2021 | Kim et al. |
| 2021/0393975 A1 | 12/2021 | Eltorai et al. |
| 2021/0395071 A1 | 12/2021 | Zubrum et al. |
| 2021/0402208 A1 | 12/2021 | Edgar |
| 2022/0001198 A1 | 1/2022 | Lee |
| 2022/0001199 A1 | 1/2022 | Beerwerth et al. |
| 2022/0008122 A1 | 1/2022 | Johnston et al. |
| 2022/0032082 A1 | 2/2022 | Shenfarber et al. |
| 2022/0054189 A1 | 2/2022 | Wootten |
| 2022/0071491 A1 | 3/2022 | Bae et al. |
| 2022/0072332 A1 | 3/2022 | Park et al. |
| 2022/0087891 A1 | 3/2022 | Goodman et al. |
| 2022/0111198 A1 | 4/2022 | Jung |
| 2022/0117632 A1 | 4/2022 | Walker et al. |
| 2022/0125706 A1 | 4/2022 | Horinek et al. |
| 2022/0126014 A1 | 4/2022 | Cederna et al. |
| 2022/0133407 A1 | 5/2022 | Anderson et al. |
| 2022/0175443 A1 | 6/2022 | Slatkine et al. |
| 2022/0176092 A1 | 6/2022 | Quan et al. |
| 2022/0203112 A1 | 6/2022 | Iger et al. |
| 2022/0211424 A1 | 7/2022 | Wootten et al. |
| 2022/0211988 A1 | 7/2022 | Ignon et al. |
| 2022/0218562 A1 | 7/2022 | Capelli et al. |
| 2022/0226668 A1 | 7/2022 | Lee et al. |
| 2022/0233400 A1 | 7/2022 | Oh et al. |
| 2022/0241107 A1 | 8/2022 | Kim et al. |
| 2022/0241146 A1 | 8/2022 | Jeong |
| 2022/0268536 A1 | 8/2022 | Stephenson et al. |
| 2022/0287910 A9 | 9/2022 | Boone, III et al. |
| 2022/0312940 A1 | 10/2022 | Hong et al. |
| 2022/0362529 A1 | 11/2022 | Castro |
| 2022/0401714 A1 | 12/2022 | Quan et al. |
| 2022/0409276 A1 | 12/2022 | Choi |
| 2023/0000523 A1 | 1/2023 | Nicolas et al. |
| 2023/0012684 A1 | 1/2023 | Ignon et al. |
| 2023/0014299 A1 | 1/2023 | Lee, Jr. et al. |
| 2023/0018295 A1 | 1/2023 | Ignon et al. |
| 2023/0019979 A1 | 1/2023 | Deem et al. |

(56) References Cited

U.S. PATENT DOCUMENTS

| | | |
|---|---|---|
| 2023/0033217 A1 | 2/2023 | Ignon et al. |
| 2023/0033761 A1 | 2/2023 | Ignon et al. |
| 2023/0042047 A1 | 2/2023 | Kim et al. |
| 2023/0055346 A1 | 2/2023 | Fortkort et al. |
| 2023/0062185 A1 | 3/2023 | Nazarian et al. |
| 2023/0104221 A1 | 4/2023 | Aharon |
| 2023/0123145 A1 | 4/2023 | Ko |
| 2023/0158282 A1 | 5/2023 | Ignon et al. |
| 2024/0017046 A1 | 1/2024 | Nebrigic et al. |
| 2024/0033491 A1 | 2/2024 | Ignon et al. |
| 2024/0075263 A1 | 3/2024 | Ignon et al. |
| 2024/0139482 A1 | 5/2024 | Ignon et al. |
| 2024/0198068 A1 | 6/2024 | Ignon et al. |
| 2024/0225697 A1 | 7/2024 | Ignon et al. |

FOREIGN PATENT DOCUMENTS

| | | | |
|---|---|---|---|
| CA | 2340154 | 9/2002 | |
| CA | 2784209 | 8/2011 | |
| CN | 3292006 | 4/2003 | |
| CN | 1708261 | 12/2005 | |
| CN | 107920948 | 4/2018 | |
| CN | 305941358 | 7/2020 | |
| CN | 306109314 | 10/2020 | |
| CN | 306995346 | 12/2021 | |
| CN | 308188687 | 8/2023 | |
| DE | 599521 | 7/1934 | |
| DE | 2415633 | 10/1975 | |
| DE | 3338057 | 8/1984 | |
| DE | 3421390 | 12/1985 | |
| DE | 234608 | 4/1986 | |
| DE | 3503343 | 8/1986 | |
| DE | 8330191 | 6/1987 | |
| DE | 3740902 | 12/1988 | |
| DE | 4237940 | 5/1993 | |
| DE | 29808395 | 8/1998 | |
| DE | 10-2004-015815 | 11/2005 | |
| EM | Des. 8794184-0001 | 12/2021 | |
| EM | Des. 8880371-0001 | 5/2022 | |
| EM | Des. 015024621-0002 | 6/2023 | |
| EP | 0258901 | 9/1987 | |
| EP | 0479121 | 4/1992 | |
| EP | 0564392 | 3/1993 | |
| EP | 0784997 | 7/1997 | |
| EP | 1238643 | 4/2000 | |
| EP | 1453558 | 9/2004 | |
| EP | 2206483 | 7/2010 | |
| EP | 2544563 | 9/2015 | |
| EP | 2106780 | 3/2016 | |
| EP | 2865867 | 5/2016 | |
| EP | 3217899 | 5/2016 | |
| EP | 2240099 | 2/2018 | |
| EP | 2967633 | 4/2018 | |
| EP | 3302319 | 4/2018 | |
| EP | 3319573 | 5/2018 | |
| EP | 3340908 | 7/2018 | |
| EP | 2451367 | 1/2020 | |
| EP | 3388006 | 3/2020 | |
| EP | 2618797 | 4/2020 | |
| EP | 3237055 | 8/2020 | |
| EP | 3795204 | 3/2021 | |
| EP | 3437575 | 4/2021 | |
| ES | 1037776 | 4/1998 | |
| FR | 2712172 | 5/1995 | |
| FR | 2773461 | 7/1999 | |
| GB | 1372609 | 10/1974 | |
| GB | 2306351 | 5/1997 | |
| GB | 2585500 | 1/2021 | |
| GB | 6228949 | 3/2022 | |
| GB | 6228947 | 9/2022 | |
| IT | 553076 | 12/1956 | |
| IT | 1184922 | 3/1985 | |
| JP | S55-034863 | 8/1963 | |
| JP | S54-63580 A | 5/1979 | |
| JP | H05-042060 | 2/1993 | |
| JP | 1993-088552 | 12/1993 | |
| JP | 1997-294747 | 11/1997 | |
| JP | 2003-534881 | 11/2003 | |
| JP | 2003-339713 | 12/2003 | |
| JP | 2004-275721 | 10/2004 | |
| JP | 2006-503627 | 2/2006 | |
| JP | 2006-204767 | 10/2006 | |
| JP | 2010-042243 | 2/2010 | |
| JP | 2012-527967 | 11/2012 | |
| JP | 2013-215621 | 10/2013 | |
| JP | 5508285 | 3/2014 | |
| JP | D1581877 | 7/2017 | |
| JP | D1609357 | 6/2018 | |
| JP | 2018-527052 | 9/2018 | |
| JP | D1675782 | 1/2021 | |
| KR | 20-0280320 | 7/2002 | |
| KR | 10-20070070173 | 7/2007 | |
| KR | 10-2018-0030607 | 3/2018 | |
| KR | 10-1836310 | 3/2018 | |
| KR | 301238287.0000 | 11/2023 | |
| KR | 301238288.0000 | 11/2023 | |
| TW | D155201 | 8/2013 | |
| TW | D176752 | 6/2016 | |
| TW | D214226 | 9/2021 | |
| WO | WO 1994/024980 | 11/1994 | |
| WO | WO 1997/000707 | 1/1997 | |
| WO | WO 1997/011650 | 3/1997 | |
| WO | WO-9923951 A1 * | 5/1999 | ........... A61B 17/545 |
| WO | WO 1999/37229 | 7/1999 | |
| WO | WO 2000/015300 | 3/2000 | |
| WO | WO 2000/79540 | 12/2000 | |
| WO | WO 2001/93931 | 12/2001 | |
| WO | WO 2004/108091 | 12/2001 | |
| WO | WO 2003/073917 | 9/2003 | |
| WO | WO 2004/037098 | 5/2004 | |
| WO | WO 2004/037287 | 5/2004 | |
| WO | WO 2005/061042 | 7/2005 | |
| WO | WO 2005/070313 | 8/2005 | |
| WO | WO 2006/018731 | 2/2006 | |
| WO | WO 2006/031413 | 3/2006 | |
| WO | WO 2007/114904 | 10/2007 | |
| WO | WO 2008/012324 | 1/2008 | |
| WO | WO 2009/086182 | 7/2009 | |
| WO | WO 2009/088884 | 7/2009 | |
| WO | WO 2009/097451 | 8/2009 | |
| WO | WO 2010/022396 | 2/2010 | |
| WO | WO 2010/068960 | 6/2010 | |
| WO | WO 2010/151704 | 12/2010 | |
| WO | WO 2011/006009 | 1/2011 | |
| WO | WO 2011/110840 | 9/2011 | |
| WO | WO 2012/131623 | 10/2012 | |
| WO | WO 2012/145667 | 10/2012 | |
| WO | WO 2013/030117 | 3/2013 | |
| WO | WO 2014/091035 | 6/2014 | |
| WO | WO 2014/151104 | 9/2014 | |
| WO | WO 2016/052818 | 4/2016 | |
| WO | WO 2016/106396 | 6/2016 | |
| WO | WO 2017/007939 | 1/2017 | |
| WO | WO 2017/111481 | 6/2017 | |
| WO | WO 2021/018765 | 2/2021 | |
| WO | WO 2021/113343 | 6/2021 | |
| WO | WO 2022/099318 | 5/2022 | |
| WO | WO 2023/039524 | 3/2023 | |
| WO | WO 2023/064718 | 4/2023 | |
| WO | WO 2023/164572 | 8/2023 | |
| WO | WO 2024/129774 | 6/2024 | |

OTHER PUBLICATIONS

U.S. Appl. No. 10/699,747 (U.S. Pat. No. 7,789,886), filed Nov. 3, 2003, Instruments and Techniques for Controlled Removal of Epidermal Layers.

U.S. Appl. No. 11/739,615 (U.S. Pat. No. 8,337,513), filed Apr. 24, 2007, Instruments and Techniques for Controlled Removal of Epidermal Layers.

(56) References Cited

OTHER PUBLICATIONS

U.S. Appl. No. 11/417,709 (U.S. Pat. No. 8,066,716), filed May 3, 2006, Instruments and Techniques for Controlled Removal of Epidermal Layers.
U.S. Appl. No. 11/417,396 (U.S. Pat. No. 7,678,120), filed May 3, 2006, Instruments and Techniques for Controlled Removal of Epidermal Layers.
U.S. Appl. No. 14/702,509 (U.S. Pat. No. 9,775,646), filed May 1, 2015, Devices and Systems for Treating the Skin Using Vacuum.
U.S. Appl. No. 14/702,486 (U.S. Pat. No. 9,468,464), filed May 1, 2015, Methods for Treating the Skin Using Vacuum.
U.S. Appl. No. 11/392,348 (U.S. Pat. No. 8,048,089), filed Mar. 29, 2006, Apparatus and Methods for Treating the Skin.
U.S. Appl. No. 13/267,554 (U.S. Pat. No. 9,474,886), filed Oct. 6, 2011, Removable Tips for Skin Treatment Systems.
U.S. Appl. No. 14/698,673 (U.S. Pat. No. 9,550,052), filed Apr. 28, 2015, Console System for the Treatment of Skin.
U.S. Appl. No. 14/698,713 (U.S. Pat. No. 9,662,482), filed Apr. 28, 2015, Methods and Systems for Extraction of Materials from Skin.
U.S. Appl. No. 14/700,789 (U.S. Pat. No. 9,814,868), filed Apr. 30, 2015, Tip With Embedded Materials for Skin Treatment.
U.S. Appl. No. 15/660,750 (U.S. Pat. No. 10,357,641), filed Jul. 26, 2017, Tip for Skin Treatment Device.
U.S. Appl. No. 15/660,777 (U.S. Pat. No. 10,357,642), filed Jul. 26, 2017, Removable Tips for Use With Skin Treatment Systems.
U.S. Appl. No. 16/517,268 (U.S. Pat. No. 11,446,477), filed Jul. 19, 2019, Devices and Methods for Treating Skin.
U.S. Appl. No. 17/165,820 (U.S. Pat. No. 11,547,840), filed Feb. 2, 2021, Devices and Methods for Treating Skin.
U.S. Appl. No. 17/165,807 (U.S. Pat. No. 11,612,726), filed Feb. 2, 2021, Devices and Methods for Treating Skin.
U.S. Appl. No. 18/094,884, filed Jan. 9, 2023, Devices and Methods for Treating Skin.
U.S. Appl. No. 09/294,254 (U.S. Pat. No. 6,162,232), filed Apr. 19, 1999, Instruments and Techniques for High-Velocity Fluid Abrasion of Epidermal Layers With Skin Cooling.
U.S. Appl. No. 09/475,480 (U.S. Pat. No. 6,299,620), filed Dec. 30, 1999, Instruments and Techniques for Inducing Neocollagenesis in Skin Treatments.
U.S. Appl. No. 09/475,479 (U.S. Pat. No. 6,387,103), filed Dec. 30, 1999, Instruments and Techniques for Inducing Neocollagenesis in Skin Treatments.
U.S. Appl. No. 11/370,200, filed Mar. 7, 2006, Microdermabrasion Method and Apparatus.
U.S. Appl. No. 12/362,353 (U.S. Pat. No. 9,056,193), filed Jan. 29, 2009, Apparatus and Methods for Treating the Skin.
U.S. Appl. No. 14/734,995 (U.S. Pat. No. 11,020,577), filed Jun. 9, 2015, Devices and Systems for Treating Skin Surfaces.
U.S. Appl. No. 17/332,897, filed May 27, 2021, Devices, Systems, and Methods for Treating the Skin.
U.S. Appl. No. 17/952,569, filed Sep. 26, 2022, Devices, Systems, and Methods for Treating the Skin.
U.S. Appl. No. 12/832,663 (U.S. Pat. No. 8,814,836), filed Jul. 8, 2010, Devices, Systems, and Methods for Treating the Skin Using Time-Release Substances.
U.S. Appl. No. 14/455,762 (U.S. Pat. No. 9,642,997), filed Aug. 8, 2014, Devices for Treating Skin Using Treatment Materials Located Along a Tip.
U.S. Appl. No. 15/588,102 (U.S. Pat. No. 10,556,097), filed May 5, 2017, Devices for Treating Skin Using Treatment Materials Located Along a Tip.
U.S. Appl. No. 16/784,850, filed Feb. 7, 2020, Devices and Methods for Treating Skin.
U.S. Appl. No. 12/346,582 (U.S. Pat. No. 8,343,116), filed Dec. 30, 2008, Apparatus and Method for Treating the Skin.
U.S. Appl. No. 13/620,376 (U.S. Pat. No. 9,486,615), filed Sep. 14, 2012, Microdermabrasion Apparatus and Method.
U.S. Appl. No. 15/344,357, (U.S. Pat. No. 10,556,096), filed Nov. 4, 2016, Devices and Methods for Skin Treatment.
U.S. Appl. No. 16/784,044, filed Feb. 6, 2020, Devices and Methods for Skin Treatment.
U.S. Appl. No. 09/540,945 (U.S. Pat. No. 6,592,595), filed Mar. 31, 2000, Microdermabrasion and Suction Massage Apparatus and Method.
U.S. Appl. No. 09/698,409 (U.S. Pat. No. 6,527,783), filed Oct. 27, 2000, Microdermabrasion and Suction Massage Apparatus and Method.
U.S. Appl. No. 10/177,173 (U.S. Pat. No. 6,673,082), filed Jun. 20, 2002, Microdermabrasion Handpiece With Supply and Return Lumens.
U.S. Appl. No. 10/315,478 (U.S. Pat. No. 6,942,649), filed Dec. 10, 2002, Microdermabrasion Fluid Application System and Method.
U.S. Appl. No. 09/699,220 (U.S. Pat. No. 6,629,983), filed Oct. 27, 2000, Apparatus and Method for Skin/Surface Abrasion.
U.S. Appl. No. 14/211,089 (U.S. Pat. No. 10,238,812), filed Mar. 14, 2014, Skin Treatment Systems and Methods Using Needles.
U.S. Appl. No. 16/363,310, filed Mar. 25, 2019, Skin Treatment Systems and Methods Using Needles.
U.S. Appl. No. 14/211,290 (U.S. Pat. No. 9,566,088), filed Mar. 14, 2014, Devices, Systems and Methods for Treating the Skin.
U.S. Appl. No. 15/430,209, (U.S. Pat. No. 10,251,675), filed Feb. 10, 2017, Devices, Systems and Methods for Treating the Skin.
U.S. Appl. No. 16/376,956 (U.S. Pat. No. 11,717,326), filed Apr. 5, 2019, Devices, Systems and Methods for Treating the Skin.
U.S. Appl. No. 17/952,721, filed Sep. 26, 2022, Devices, Systems and Methods for Treating the Skin.
U.S. Appl. No. 17/952,676, filed Sep. 26, 2022, Devices, Systems and Methods for Treating the Skin.
U.S. Appl. No. 14/774,641 (U.S. Pat. No. 10,172,644), filed Sep. 10, 2015, Devices, Systems and Methods for Treating the Skin.
U.S. Appl. No. 16/241,572 (U.S. Pat. No. 10,993,743), filed Jan. 7, 2019, Devices, Systems and Methods for Treating the Skin.
U.S. Appl. No. 17/163,128, filed Jan. 29, 2021, Devices, Systems and Methods for Treating the Skin.
U.S. Appl. No. 17/163,199 (U.S. Pat. No. 11,517,350), filed Jan. 29, 2021, Devices, Systems and Methods for Treating the Skin.
U.S. Appl. No. 17/163,237 (U.S. Pat. No. 11,202,657), filed Jan. 29, 2021, Devices, Systems and Methods for Treating the Skin.
U.S. Appl. No. 17/163,240 (U.S. Pat. No. 11,213,321), filed Jan. 29, 2021, Devices, Systems and Methods for Treating the Skin.
U.S. Appl. No. 14/998,375 (U.S. Pat. No. 9,498,610), filed Dec. 23, 2015, Devices and Methods for Treating the Skin Using a Rollerball or a Wicking Member.
U.S. Appl. No. 15/354,754 (U.S. Pat. No. 10,035,007), filed Nov. 17, 2016, Devices and Methods for Treating the Skin.
U.S. Appl. No. 16/040,397, filed Jul. 19, 2018, Devices and Methods for Treating the Skin.
U.S. Appl. No. 17/164,580, filed Feb. 1, 2021, Devices and Methods for Treating the Skin.
U.S. Appl. No. 15/498,416 (U.S. Pat. No. 10,179,229), filed Apr. 26, 2017, Devices and Methods for Treating the Skin Using a Porous Member.
U.S. Appl. No. 16/246,306 (U.S. Pat. No. 11,224,728), filed Jan. 11, 2019, Devices and Methods for Treating the Skin Using a Porous Member.
U.S. Appl. No. 17/576,888, filed Jan. 14, 2022, Devices and Methods for Treating the Skin.
U.S. Appl. No. 15/204,939 (U.S. Pat. No. 11,241,357), filed Jul. 7, 2016, Devices, Systems and Methods for Promoting Hair Growth.
U.S. Appl. No. 17/592,432, filed Feb. 3, 2022, Devices, Systems and Methods for Improving Scalp Health.
U.S. Appl. No. 18/035,723, filed May 5, 2023, Devices, Systems and Methods for Treating the Skin.
U.S. Appl. No. 29/811,066, filed Oct. 11, 2021, Skin Treatment System.
U.S. Appl. No. 29/807,430, filed Sep. 10, 2021, Skin Treatment Device.
U.S. Appl. No. 29/807,428, filed Sep. 10, 2021, Container for a Skin Treatment Device.
U.S. Appl. No. 29/829,476, filed Mar. 4, 2022, Light Therapy Device for Skin Care.
U.S. Appl. No. 29/811,070, filed Oct. 11, 2021, Skin Treatment Tip.

(56) References Cited

OTHER PUBLICATIONS

U.S. Appl. No. 29/826,153, filed Feb. 9, 2022, Dual Treating Device for Treating Acne or Wrinkles.
U.S. Appl. No. 29/854,067, filed Sep. 21, 2022, Treatment Device for Skin.
U.S. Appl. No. 29/884,441, filed Feb. 10, 2023, Skin Treatment Tip.
"BeautyBio: GLOfacial Hydro-Infusion deep pore cleansing + Blue LED clarifying tool", found online at amazon.com Sep. 26, 2023, ref. dated Nov. 15, 2022, retrieved https://www.amazon.com/GLOfacial-Hyrdo-Infusion-Deep-Cleansing-Clarifying/dp/B0BGJLMSZP/.
"Healthline: What is a HydraFacial and how does it work", found online at healthline.com Sep. 26, 2023, Ref. dated Dec. 9, 2020, https://www.healthline.com/health/what-is-hydrafacial.
"InStyle: Why the HydraFacial is one of the most popular in-office treatments", found online at instyle.com on Sep. 26, 2023, ref. dated Jun. 12, 2023, https://www.instyle.com/beauty/skin/hydrafacial-treatment-facts.
"Microderm Glo: Glo Mini", found online at microdermglo.com Sep. 26, 2023, ref. dated Sep. 27, 2019, https://www.microdermglo.com/collections/microdermabrasion-machines.
Amazon, FAZJEUNE 7 Color LED Light, LED Face Mask Skin Rejevenation PDT Photon Facial Skin Care Mask Skin Tightening Lamp SPA Face Device Beauty Salon Equipment Anti-aging RemoveWrinkle, Customer reviewed on Sep. 2020, retrieved from internet at https://www.amazon.com/FAZJEUNE-Rejuvenation-Tightening-Equipment-Anti-aging/dp/B08B4M8RQQ/ref=psdc_11061121_13_B08ZSPZSF4.
Cox III et al., Decreased Splatter in Dermabrasion, Arch Facial Plastic Surgery, Jan.-Mar. 2000, vol. 2, pp. 23-26.
Ditre et al., Effect of a-hydroxy acids on photoaged skin: A pilot clinical, histologic, and ultrastructuralstudy, Journal of American Academy of Dermatology, Feb. 1996, vol. 34, No. 2, Part 1, pp. 187-195.
Harris et al., Combining Manual Dermasanding with Low Strength Trichloroacetic Acid to Improve Antinically Injured Skin, the Journal of Dermatologic Surgery and Oncology, Jul. 1994, vol. 20, No. 7, pp. 436-442.
HYDRAFACIAL® Tower—User guide. Edge Systems. Revised Jun. 23, 2016. p. No. 16.
Microdermabrader Pepita Instruction Manual, Mattioli Engineering S.R.L., PEP_USA2.doc Rev 1.1, Sep. 29, 1997.
International Search Report and Written Opinion for related PCT appl. PCT/US2010/041430 dated Jan. 19, 2012.
International Search Report and Written Opinion for related PCT appl. PCT/US2009/032465 dated Mar. 18, 2009.
Beautimate adjustable Hydra Needle Microneedling Serium Applicator, https://www.beautimate.com/products/adjustable-hydra-needle, first accessed Aug. 12, 2023.
Hydrafacial Hydropeel Vortex Fusion Tips, https://mergesouq.com/products/hydrafacial-hydropeel-vortex-fusion-tips, first accessed Aug. 12, 2023.
Amazon.com: leBilif Facial Skin Care Machine, posted Dec. 14, 2023 (retrieved online Mar. 29, 2024) from https://www.amazon.com/leBillif-Equipment-Esthetician-Essential-supplies/d (2023).
Amazon.com: Osaki LED Therapy Dome, posted date unavailable (retrieved online Mar. 29, 2024), from https://www.amazon.com/Osake-LED-Therapy-Dome/dp/BO8NN3BS7L (2024).
Celluma LITE Compact LED Light Therapy Device fr Travel, posted date unavailable, (retrieved online Mar. 29, 2024), from https://www.celluma.com/products/celluma-lite (2024).
Elipsa-LightSlim, posted date unavailable, (retrieved online Mar. 29, 2024), from https://www.lightslim.com/products/lightslim-elipsa (2024).
HydraFacial MD Karma Spa Lounge & Beauty Bar, posted date unavailable (retrieved online Mar. 29, 2024), from https://www.karmabeautybar.com/hydrafacial-md (2024).

\* cited by examiner

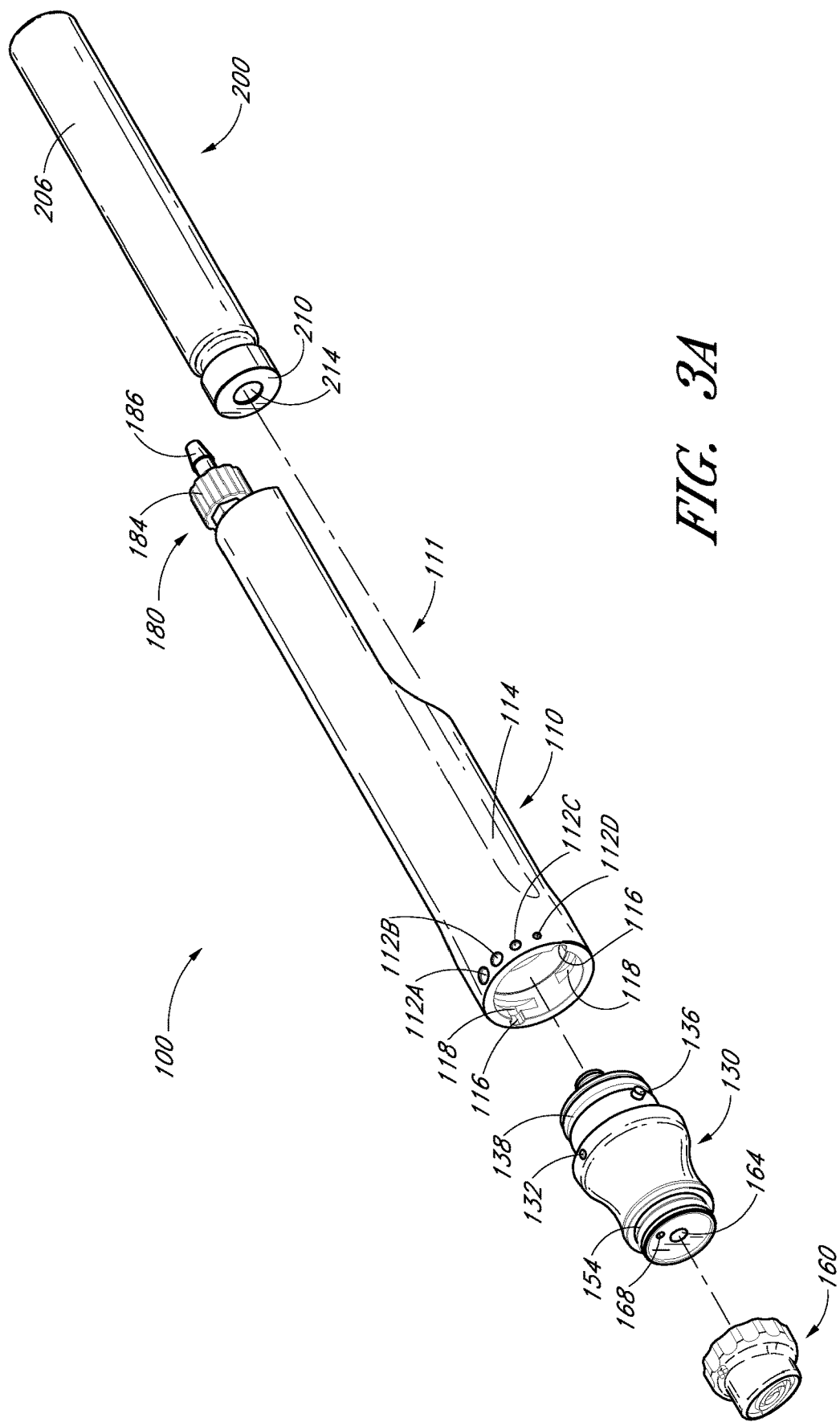

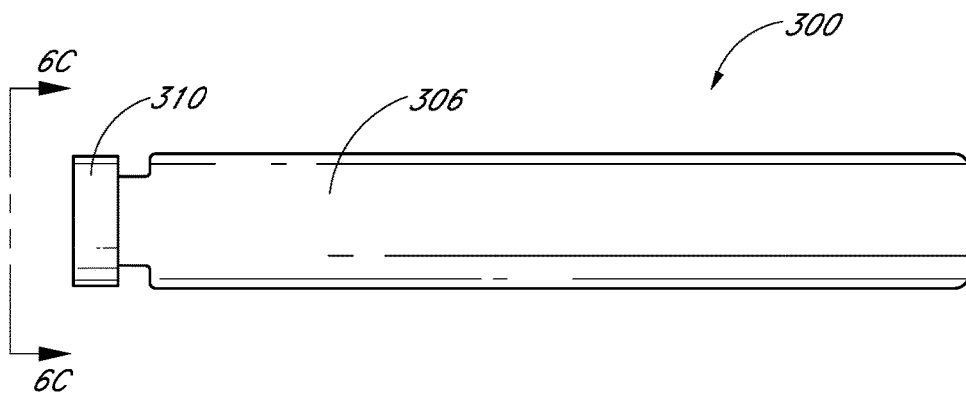
FIG. 6A
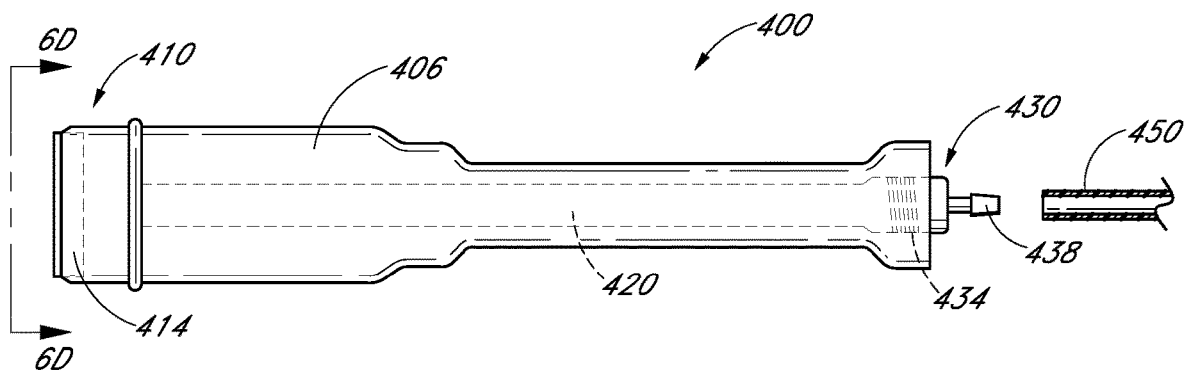
FIG. 6B
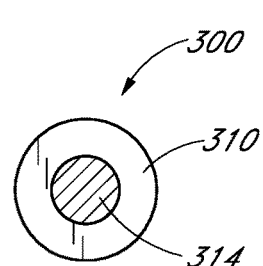 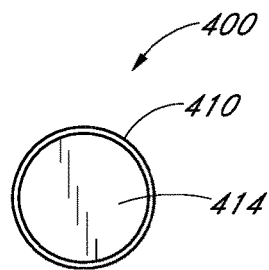
FIG. 6C          FIG. 6D

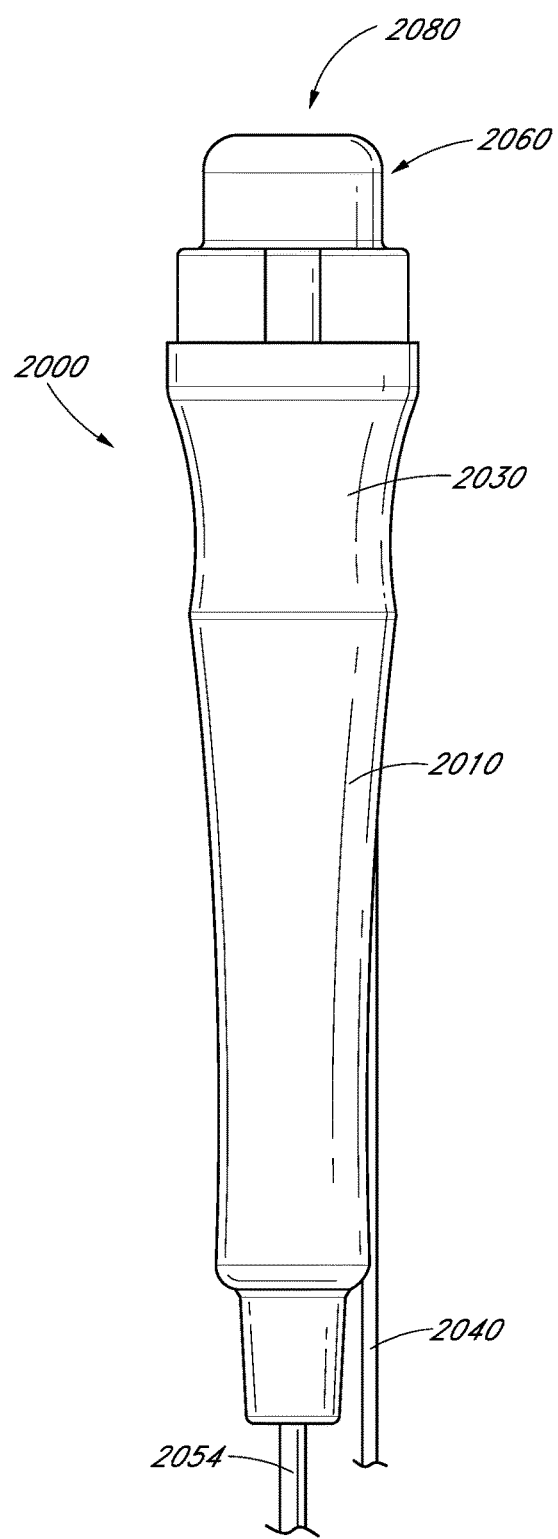
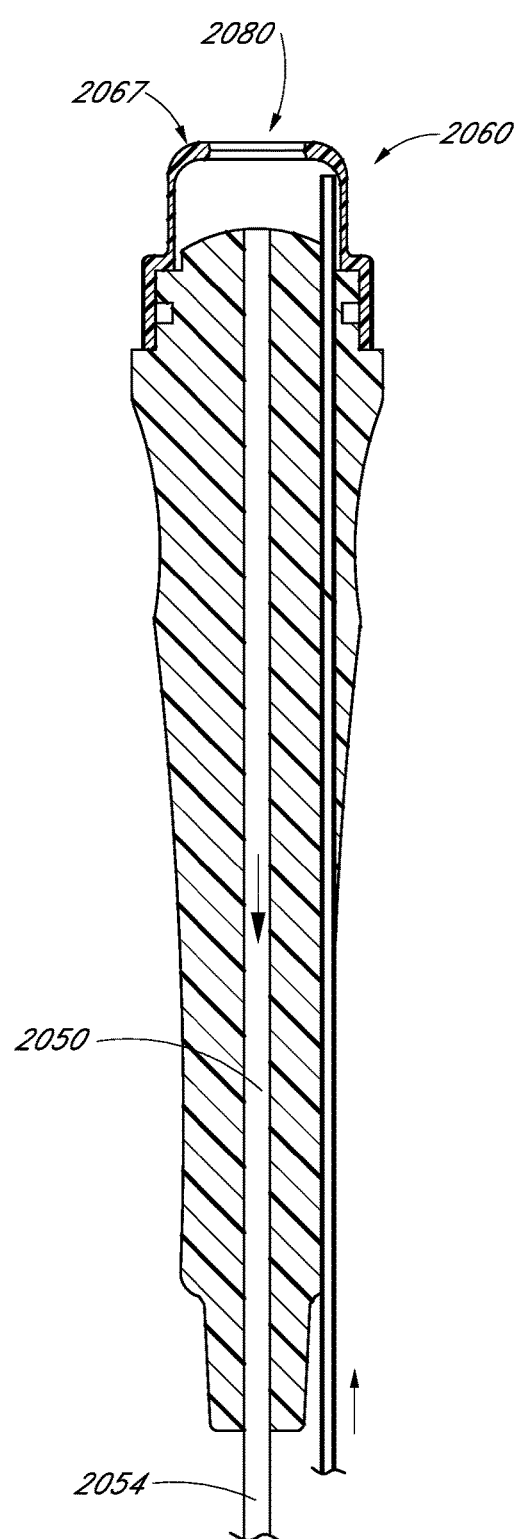
*FIG. 20B*  *FIG. 20C*

DEVICES, SYSTEMS AND METHODS FOR SKIN TREATMENT

CROSS REFERENCE TO RELATED APPLICATIONS

This application is a continuation application of U.S. patent application Ser. No. 17/332,897, filed May 27, 2021, which is a continuation application of U.S. patent application Ser. No. 14/734,995, filed Jun. 9, 2015 and issued as U.S. Pat. No. 11,020,577 on Jun. 1, 2021, which is a continuation application of U.S. patent application Ser. No. 12/362,353, filed Jan. 29, 2009 and issued as U.S. Pat. No. 9,056,193 on Jun. 16, 2015, which claims the priority benefit under 35 U.S.C. § 119(e) of U.S. Provisional Application No. 61/024,504, filed Jan. 29, 2008, the entireties of all of which are hereby incorporated by reference as if fully set forth herein.

BACKGROUND

Field of the Inventions

This application relates generally to skin treatment, and more specifically, to apparatuses, systems and methods for treating a person's skin.

Description of the Related Art

Abrasion of the outer layer or epidermis of the skin is desirable to smooth or blend scars, blemishes or other skin conditions that may be caused by, for example, sun exposure, acne, other skin disorders, aging and/or the like. Standard techniques used to abrade the skin have generally been separated into two fields that are commonly referred to as dermabrasion and microdermabrasion. In both techniques, portions of the epidermis (e.g., the stratum corneum) are removed. As part of its normal regeneration function, the body then replaces the lost skin cells, resulting in a new outer layer of skin. Additionally, despite the mild edema and erythema associated with the procedures, the skin eventually looks and feels smoother than prior to the treatment because of the new outer layer of skin.

Dermabrasion generally refers to a procedure in which the outer surface of the skin is removed due to mechanical rubbing by a handpiece with an abrasive element that is often in the form of a burr, wheel, disc or the like. This process tends to be messy and painful, sometimes necessitating the administration of a local anesthetic to the person being treated. In general, dermabrasion leaves the skin red and raw-looking. The removed skin can take several months to regrow and heal. Recent efforts have led to the use of lasers instead of abrasive elements, resulting in less bleeding. However, the pain and messiness of such procedures normally remain.

Efforts have been made to decrease the mess caused by the process waste, such as, for example, removed skin, blood, other debris and the like, by adding a suction element. As the process waste is drawn into the suction opening, skin that has not been removed is also pulled against the grit surrounding the suction opening, so the procedure remains relatively messy due to the abrasion that takes place outside of the handpiece by the grit.

In general, microdermabrasion refers generally to a procedure in which the surface of the skin is removed by mechanical rubbing using a handpiece that can discharge a stream of sand or grit. For example, a handpiece can be used to direct a fluid containing crystals of aluminum oxide, sodium chloride and/or sodium bicarbonate. The velocity and momentum of the grit helps wear away cell layers of the skin with each pass of the handpiece. Alternatively, new "crystal-free" microdermabrasion techniques utilize a diamond-tipped handpiece without a stream of grit.

Efforts to add a suction element have been more successful in microdermabrasion than in dermabrasion, because the handpiece applying the stream of grit is more controllable to a localized area. That is, as the removed skin is drawn into the suction opening, skin that has not been removed is also pulled towards the handpiece where it is treated with the grit stream, allowing for simultaneous local treatment and suction.

Microdermabrasion typically removes moisture from the skin. Thus, the procedure is generally followed by the application of moisturizing creams, other agents and/or other materials. However, similar to topical application of moisturizing creams prior to microdermabrasion, the moisturizing elements only work as deep as the active ingredients can passively migrate through the remaining epidermis.

SUMMARY

According to certain embodiments of the present application, a handpiece assembly for treating a skin surface comprises a recess configured to receive a cartridge or other container. The cartridge or other container comprises one or more treatment materials, such as, for example, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In one embodiment, the handpiece assembly comprises a valve or other flow control device or feature to enable a user to selectively regulate a flowrate of a treatment material through the handpiece assembly. In other embodiments, the cartridge or other container comprises an inlet configured to be in fluid communication with water, saline, another dilutant or dissolvent or another fluid. The water, saline, another dilutant or dissolvent or another fluid is configured to be delivered through the inlet and to an interior of the cartridge so as to mix or combine with a treatment material contained therein. In some embodiments, the treatment material contained within the cartridge or container is a liquid, solid, gel, granulated material or concentrated solution. In some embodiments, one or more treatment fluids are conveyed from an outlet of the cartridge or container to a tip attached to a distal end of the handpiece assembly.

According to other embodiments, a treatment material disposed on or near the tip of the handpiece assembly is configured to be mixed or combined with water, saline or another fluid being delivered through the handpiece assembly to create a treatment fluid. In certain embodiments, the treatment material is provided as a solid, semi-solid, gel, granulated material or concentrated fluid or solution. In some arrangements, the treatment material is positioned within a recess of the tip, between the tip and a main body portion of the handpiece assembly or within the main body portion of the handpiece assembly. In some embodiments, water, saline, treatment fluid or other fluid being conveyed through the handpiece assembly is configured to be heated.

According to certain embodiments of the present application, a device for treating a skin surface comprises a handpiece assembly having a distal end and a proximal end. The handpiece assembly comprises at least one delivery conduit and at least one waste conduit. The handpiece assembly further comprising a recess or other opening configured to receive a cartridge or other container having an interior cavity. In one embodiment, the interior cavity of the cartridge is placed in fluid communication with the fluid delivery conduit when the cartridge is secured within the recess. The device additionally includes a tip positioned along the distal end of the handpiece assembly, such that the tip is configured to contact the skin surface. In certain embodiments, the tip comprises a peripheral lip, a first opening in fluid communication with the fluid delivery conduit and a second opening in fluid communication with the waste conduit and an abrasive element. The first opening, the second opening and the abrasive element are generally positioned along an interior of the peripheral lip. In one embodiment, the waste conduit is configured to be in fluid communication with a vacuum to selectively remove debris away from the tip. In other arrangements, the delivery conduit is placed in fluid communication with the waste conduit and the vacuum when the peripheral lip contacts a skin surface.

In certain arrangements, the device further includes a valve generally positioned between the interior cavity of the cartridge and the fluid delivery conduit. The valve can be adapted to control the flowrate of a fluid being conveyed from the interior cavity of the cartridge to the tip. In other embodiments, the handpiece assembly comprises an adjustable intermediate space positioned generally between the interior cavity of the cartridge and the fluid delivery conduit. In one arrangement, a volume of the adjustable intermediate space can be selectively modified by moving an actuator on the handpiece assembly. In other configurations, the handpiece assembly comprises a stem in fluid communication with the fluid delivery conduit. The stem can be adapted to extend into the interior cavity of a cartridge when the cartridge is positioned with the recess of the handpiece assembly. In other embodiments, the tip is selectively removable from the handpiece assembly. In one arrangement, the abrasive element comprises a plurality of posts, other protruding members, a spiral-shaped ridge, an abrasive surface, a foam pad, another type of pad and/or the like. In some arrangements, the device further includes a heating element configured to selectively heat a fluid being conveyed through the delivery conduit, another interior passage or conduit of the handpiece assembly, the tip, an inlet line and/or the like. In other embodiments, the cartridge comprises an inlet configured to be placed in fluid communication with a delivery source.

According to other arrangements, a skin treatment system includes a handpiece assembly having a distal end and a proximal end. The handpiece assembly comprises a fluid delivery conduit. In one embodiment, the handpiece assembly comprises a first portion and a second portion, with the first portion being selectively movable relative to the second portion. The skin treatment system further includes a tip adapted to contact skin and positioned on the distal end of the handpiece assembly. In one embodiment, the tip comprises a first opening, which is in fluid communication with the fluid delivery conduit, and an abrasive element. The system further comprises an intermediate space generally defined between the first and second portions of the handpiece assembly. Movement of the first portion with respect to the second portion can modify the volume of the intermediate space and generally control the flowrate of a fluid being conveyed through the fluid delivery conduit. In some embodiments, the system further includes an actuator on the handpiece assembly for moving the first portion relative to the second portion.

According to other embodiments, movement of the first portion with respect to the second portion is produced by rotating the second portion relative to the first portion. In some arrangements, the tip is selectively removable from the second portion. In another adaptation, the tip comprises a plurality of posts or protruding members configured to treat skin. In other arrangements, the tip comprises one or more ridges (e.g., spiral-shaped ridges), abrasive surfaces or elements and/or other features or components configured to treat skin. In certain embodiments, the handpiece assembly further comprises a waste channel in fluid communication with a second opening in the tip. In another embodiment, the handpiece assembly includes a recessed area configured to receive a cartridge comprising at least one treatment fluid or material. In other arrangements, the cartridge includes an interior portion which is at least partially defined by a membrane. The membrane can be configured to be pierced by a hollow spike of the first portion of the handpiece assembly when the cartridge is properly inserted within the recessed area, so that the hollow spike is placed in fluid communication with the delivery channel. In certain configurations, the interior portion of the cartridge comprises human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance. In other arrangements, the device comprises a heater configured to selectively heat a fluid being conveyed through the fluid delivery conduit toward the tip.

According to certain embodiments, a method of providing a treatment fluid to a skin surface while treating said skin surface with a handpiece device includes providing at least one treatment material on or within a handpiece device. In one arrangement, a tip is configured to be removably positioned along a distal end of a main body portion of the handpiece assembly. The tip can be adapted to abrade or otherwise treat skin when moved relative to a skin surface. The treatment method additionally includes directing a first fluid through a delivery passage of the handpiece assembly so that said delivery passage generally contacts at least one treatment material of the tip. In some arrangements, the treatment material is configured to at least partially dissolve, dilute or combine with the first fluid so as to create a desired treatment fluid. Further, the treatment fluid can be configured to be provided to the tip and to the skin surface being treated while a distal end of the tip is being translated over said skin surface.

In some arrangements, the treatment material comprises a solid, granular material, gel or concentrated solution and/or any other material. In other embodiments, the first fluid comprises water (e.g., sterile, tap, distilled, filtered, etc.), saline, other dilutants or dissolvents and/or any other fluid. In other arrangements, the treatment fluid comprises human growth factors, cytokines, soluble collagen, antioxidants or matrix proteins. In another embodiment, the treatment material is positioned in or near the tip, such as, for example, within a post, other protruding member, other recess, underneath the tip and/or like. In other arrangements, the treatment material comprises a disc, tablet, capsule, granular material, gel and/or the like. In one embodiment, the treatment material is configured to be positioned within a cage or other porous container. In other arrangements, the disc, table, capsule or other treatment material is configured to be secured generally between the main body portion and the tip of the handpiece assembly. In one configuration, the method further includes regulating a flowrate of the first fluid by selectively controlling a valve on the handpiece assembly. In another arrangement, the method additionally includes selectively heating the first fluid using a heating member positioned in thermal communication with the delivery passage of the handpiece assembly. In some embodiments, the treatment material is positioned within a cartridge which is configured to be removably secured to a receiving area of the handpiece assembly.

According to some embodiments disclosed in the present application, a device for treating the skin comprises a handpiece assembly having a distal end and a proximal end, a cartridge comprising an interior cavity and a tip on the distal end of the handpiece assembly. The handpiece assembly includes a fluid delivery conduit and a waste conduit. In addition, the cartridge is coupled to the handpiece assembly, with the interior cavity of the cartridge being in fluid communication with the fluid delivery conduit. Further, the tip is configured to contact the skin. The tip comprises a peripheral lip, a first opening in fluid communication with the fluid delivery conduit, a second opening in fluid communication with the waste conduit and an abrasive element. The first opening, the second opening and the abrasive element of the tip are generally positioned within the peripheral lip.

In some embodiments, the device further comprising a valve positioned between the interior cavity of the cartridge and the fluid delivery conduit. In one embodiment, the handpiece assembly comprises an adjustable intermediate space positioned generally between the interior cavity of the cartridge and the fluid delivery conduit. In another arrangement, a volume of the adjustable intermediate space can be selectively modified by moving an actuator on the handpiece assembly. In other embodiments, the handpiece assembly comprises a recessed area configured to receive the cartridge.

According to other embodiments, the handpiece assembly comprises a stem that is in fluid communication with the fluid delivery conduit as the stem is configured to extend into the interior cavity of a cartridge when the cartridge is coupled to the handpiece assembly. In another embodiment, the tip is selectively removable from the handpiece assembly. In some arrangements, the abrasive element comprises a plurality of protruding members. In other embodiments, the tip comprises an abrasive edge.

According to another embodiment, a system for treating the skin comprises a handpiece assembly having a distal end and a proximal end and a tip on the distal end of the handpiece assembly configured to contact the skin. The handpiece assembly includes a fluid delivery conduit and first and second portions. Further, the tip includes a first opening in fluid communication with the fluid delivery conduit and an abrasive element. An intermediate space generally defined between the first and second portions of the handpiece assembly is in fluid communication with the fluid delivery conduit. In one embodiment, movement of the first portion with respect to the second portion modifies the volume of the intermediate space to control a flowrate through the fluid delivery conduit. The system further comprises an actuator on the handpiece assembly for actuating movement between the first portion and the second portion.

In some embodiments, movement of the first portion with respect to the second portion is produced by rotating the second portion relative to the first portion. In other embodiments, the tip is selectively removable from the second portion. In still other arrangements, the tip comprises a plurality of protruding members configured to treat skin. In another embodiment, the tip comprises an abrasive surface configured to treat skin.

According to some embodiments, the handpiece assembly further comprises a waste channel in fluid communication with a second opening in the tip. In another arrangement, the handpiece assembly includes a recessed area configured to receive a cartridge comprising at least one treatment fluid or material. In other embodiments, the cartridge includes an interior portion at least partially defined by a membrane. The membrane is configured to be pierced by a hollow spike of the first portion of the handpiece assembly. Further, the hollow spike is in fluid communication with the delivery channel. In one embodiment, the interior portion of the cartridge comprises human growth factors, cytokines, soluble collagen, antioxidants and/or matrix proteins.

According to other embodiments, the present application discloses a method for treating the skin of a patient with a skin treatment device having a working end that includes an abrading structure configured to engage and abrade skin. The method includes placing the working end of the skin treatment device against the skin of the patient, translating the working end over the skin to abrade a skin surface, providing a treatment fluid to the skin through an opening in the working end and aspirating skin debris from the skin surface through an aspiration opening in the working end of the skin treatment device. In some embodiments, the treatment fluid comprises human growth factors, cytokines, soluble collagen, antioxidants and/or matrix proteins.

According to some embodiments disclosed in the present application, a device for treating the skin comprises a handpiece assembly having a distal end and a proximal end. The handpiece assembly includes a fluid delivery conduit and a waste conduit. In addition, the handpiece assembly is adapted to receive a cartridge having an interior cavity. Further, the device includes a tip attached to the distal end of the handpiece assembly and comprising a surface configured to treat skin. The waste conduit is configured to be in fluid communication with a vacuum source and the fluid delivery conduit is configured to be in fluid communication with an interior cavity of a cartridge when a cartridge is secured to the handpiece assembly.

In some embodiments, the handpiece assembly comprises a flow control feature configured to selectively regulate a flowrate through the fluid delivery conduit. In another arrangement, the handpiece assembly includes a main body portion and an adjustable portion attached to the main body portion. The flow control feature can comprise an adjustable intermediate space generally located between the main body portion and the adjustable portion. In other embodiments, a volume of the adjustable intermediate space can be selectively modified by moving the main body portion relative to the adjustable portion of the handpiece assembly.

In one embodiment, the handpiece assembly comprises a recessed area configured to secure a cartridge. In another arrangement, the handpiece assembly comprises a stem adapted to access an interior cavity of a cartridge when a cartridge is secured to the handpiece assembly. According to some embodiments, the tip is selectively removable from the handpiece assembly. In other embodiments, the tip comprises a plurality of protruding members configured to treat skin. In still other arrangements, the tip comprises an abrasive surface configured to treat skin.

According to another embodiment, a system for treating the skin includes a handpiece assembly. The handpiece assembly comprises a tip configured to treat skin, a first portion and a second portion. The first portion includes a delivery conduit, which has a first longitudinal axis, and is configured to be in fluid communication with at least one fluid source. Further, the second portion includes a distal end and a proximal end, with the proximal end being attached to the main body portion and the distal end being attached to the tip. The second portion includes a delivery channel having a second longitudinal axis and being in fluid communication with the tip and the delivery conduit. In addition, the second portion further comprises a removal channel being in fluid communication with the tip and a suction source. In some embodiments, an intermediate space is generally defined between the first and second portions of the handpiece assembly. Such an intermediate space is in fluid communication with the delivery conduit of the first portion and the delivery channel of the second portion. Further, a volume of the intermediate space is configured to be adjusted by selectively modifying a separation distance between the first portion and the second portion. Accordingly, a flowrate from a fluid source to the tip can be selectively controlled by modifying the separation distance between the first portion and the second portion.

In some embodiments, the separation distance between the first portion and the second portion is modified by rotating the second portion relative to the first portion. In other arrangements, the first longitudinal axis of the delivery conduit is generally offset with the second longitudinal axis of the delivery channel. In one embodiment, the tip is selectively removable from the second portion.

According to some embodiments, the tip comprises a plurality of protruding members configured to treat skin. In other embodiments, the tip comprises an abrasive surface configured to treat skin. In one embodiment, the first portion further comprises a waste channel in fluid communication with the removal channel of the second portion. In another arrangement, the first portion includes a recessed area configured to receive a cartridge comprising at least one treatment fluid or material. In some embodiments, the cartridge includes an interior portion at least partially defined by a membrane which is configured to be pierced by a hollow spike of the first portion of the handpiece assembly. The hollow spike is in fluid communication with the delivery channel. According to other embodiments, the cartridge the interior portion of the cartridge comprises human growth factors, cytokines, soluble collagen, antioxidants or matrix proteins.

According to other embodiments disclosed in the present application, a method of treating the skin comprises providing a handpiece assembly comprising a body and a tip having a distal end. The handpiece assembly includes a delivery conduit and a waste conduit that are in fluid communication with the distal end of the tip. The method further includes placing the delivery conduit of the handpiece assembly in fluid communication with a fluid source for providing at least one treatment fluid to the distal end of the tip and placing the waste conduit of the handpiece assembly in fluid communication with a suction source for removing waste materials from the distal end of the tip. In addition, the method comprises moving the handpiece assembly along a person's skin and activating the suction source to remove a volume of waste materials from the distal end of the tip and to simultaneously deliver a volume of the treatment fluid to the distal end of the tip. In one embodiment, the flowrate at which treatment fluids and/or other materials are delivered to the tip can be varied by a valve or other flow control feature of the handpiece assembly. In some embodiments, the treatment fluid comprises human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents (e.g., kojic acid), peptides, acids, anesthetics, medicants, other non-active or active compounds, other fluids or materials, combination or mixtures thereof and/or any other substance.

BRIEF DESCRIPTION OF THE DRAWINGS

These and other features, aspects and advantages of the present inventions are described with reference to drawings of certain preferred embodiments, which are intended to illustrate, but not to limit, the present inventions. The drawings include fifty-eight (58) figures. It is to be understood that the attached drawings are for the purpose of illustrating concepts of the present inventions and may not be to scale.

FIG. 3A illustrates an exploded perspective view of the handpiece assembly of FIG. 1;

FIG. 6A illustrates a side view of one embodiment of a cartridge adapted to be inserted within a handpiece assembly;

FIG. 6B illustrates a side view of another embodiment of a cartridge adapted to be inserted within a handpiece assembly;

FIG. 6C illustrates a front view of the cartridge of FIG. 6A;

FIG. 6D illustrates a front view of the cartridge of FIG. 6B;

FIG. 20B illustrates a side view of the handpiece assembly of FIG. 20A;

FIG. 20C illustrates a cross-sectional view of the handpiece assembly of FIG. 20A;

DETAILED DESCRIPTION OF THE PREFERRED EMBODIMENTS

Figure 1:
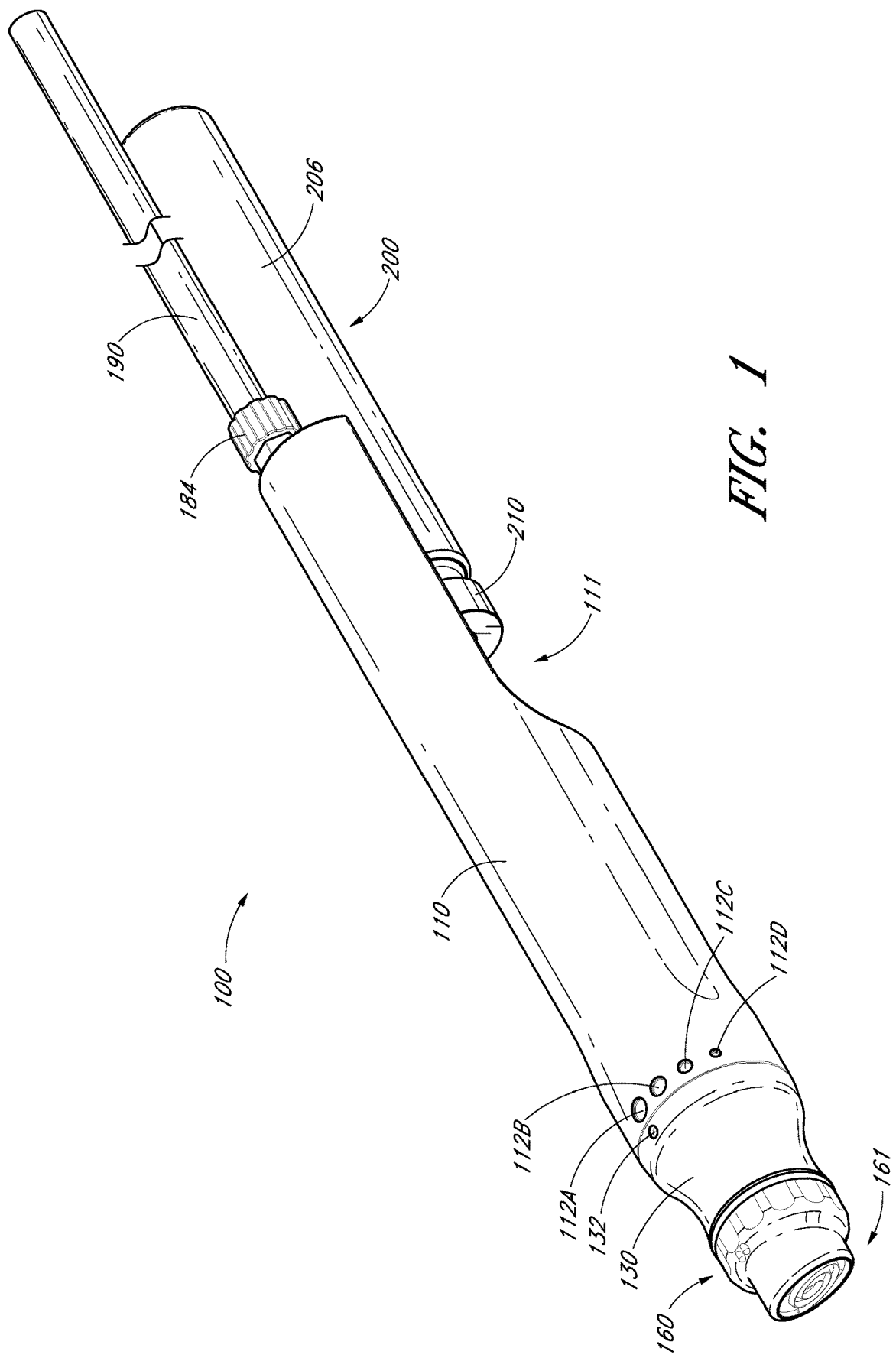
FIG. 1 illustrates a perspective view of a handpiece assembly configured for use with a skin treatment system according to one embodiment.

FIG. 1 illustrates one embodiment of a handpiece assembly 100 configured for use with a skin treatment system. Although the various embodiments of a handpiece assembly, a tip and related components have specific relevance to a skin treatment system, the features, advantages and other characteristics disclosed herein may have direct or indirect applicability in other applications, such as, for example, other medical devices, mechanical devices and/or the like. As shown, the handpiece assembly 100 can include a main body portion 110, an adjustable distal portion 130 and a tip 160. In addition, as illustrated in the depicted embodiment, the handpiece assembly 100 can include one or more connections that are configured to transfer fluids or other materials to and/or from the working end of the assembly 100. For example, as discussed in greater detailed herein, the handpiece assembly 100 can be in fluid communication with a waste conduit 190 that is adapted to remove exfoliated skin, serums, other fluids or materials and/or the like from the working surface.

With continued reference to FIG. 1, the handpiece assembly 100 can be advantageously configured to receive a cartridge 200. In some embodiments, the cartridge 200 comprises human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents (e.g., kojic acid), peptides, acids, anesthetics, medicants, other non-active or active compounds, other fluids or materials, combination or mixtures thereof and/or any other substance. As discussed in greater detail herein, such materials can be selectively delivered to a user's skin while the handpiece assembly 100 is being used. In some embodiments, the handpiece assembly 100 includes an adjustable valve or other flow control feature to enable a user to regulate the rate of delivery of such fluids or other materials to the treatment surface.

In alternative embodiments, such as, for example, those discussed herein with reference to FIGS. 11-16, 19A, 19B, 20A-20D, 21A and 21B, one or more materials can be strategically embedded, impregnated, placed, stored and/or otherwise disposed on one or more surfaces or areas of the tip or other portion or component of the skin treatment system (e.g., the foam pads of FIG. 19A-20B). Such materials can comprise solids, semi-solids, other dried substances, gels, concentrated solutions and/or the like. For example, such materials can be provided in loose form (e.g., positioned on or within a recess, other portion of the tip, within a cartridge or other container, adhered to one or more surfaces, etc.), as a tablet, capsule, pill, disc or other dissolvable solid, saturated within a foam pad or other sponge-like material and/or the like. Thus, in certain arrangements, water (e.g., distilled, tap water, filtered, etc.), saline, other dilutants and/or other fluids which are delivered to the tip can selectively dissolve, liquefy, melt, soften, dilute or otherwise prepare the materials embedded, impregnated and/or otherwise positioned on the tip, within a cartridge or other container and/or on or within another portion or component of a skin treatment system (e.g., handpiece assembly, fluid line upstream of the handpiece assembly, etc.). Accordingly, the desired human growth factors, cytokines, soluble collagen, antioxidants, matrix proteins, serums, water, saline, other dilutants or dissolvents, vitamins, chemical exfoliation agents, lotions, soothing agents, brightening or lightening agents, peptides, acids, anesthetics, medicants, other non-active or active compounds, other fluids or materials, combination or mixtures thereof and/or any other substance can be advantageously provided to the skin surface being treated, as desired or required.

In addition, as illustrated in FIG. 1, the handpiece assembly 100 can be connected to a vacuum. For example, the waste conduit 190 of the handpiece assembly can be placed in fluid communication with a suction source in order to remove exfoliated skin, spent fluids, waste materials and/or other substances away from the treatment surface. According to certain arrangements, the handpiece assembly 100 is configured to receive one or more removable tips 160, which may be selected based upon the specific procedure being performed, the desired result and/or any other considerations. Additional details regarding removable tips are provided with reference to certain embodiments disclosed herein.

Figure 2A:
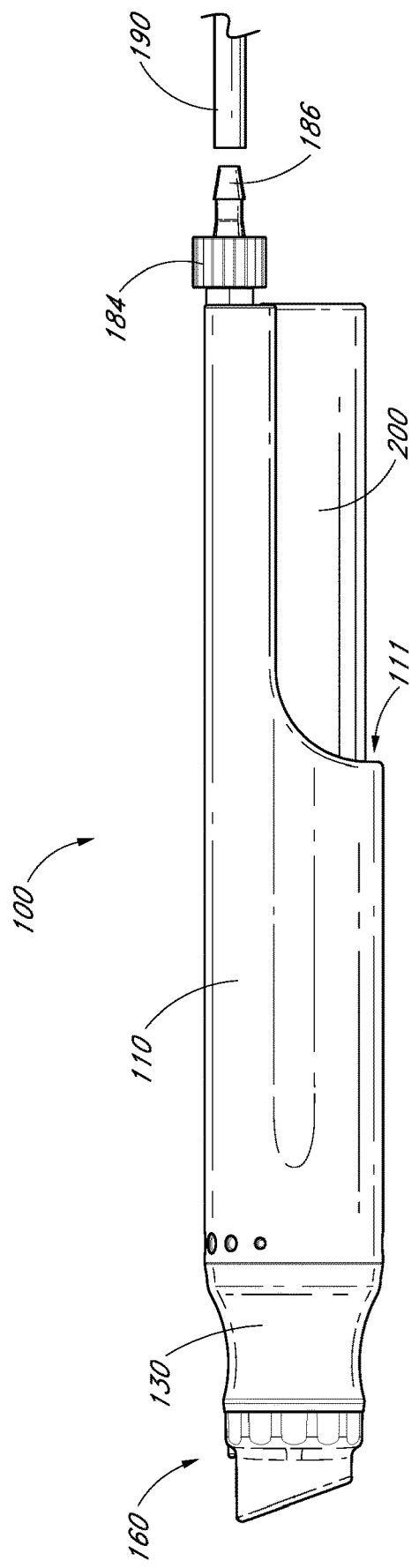
FIG. 2A illustrates a side view of the handpiece assembly of FIG. 1.
Figure 2B:
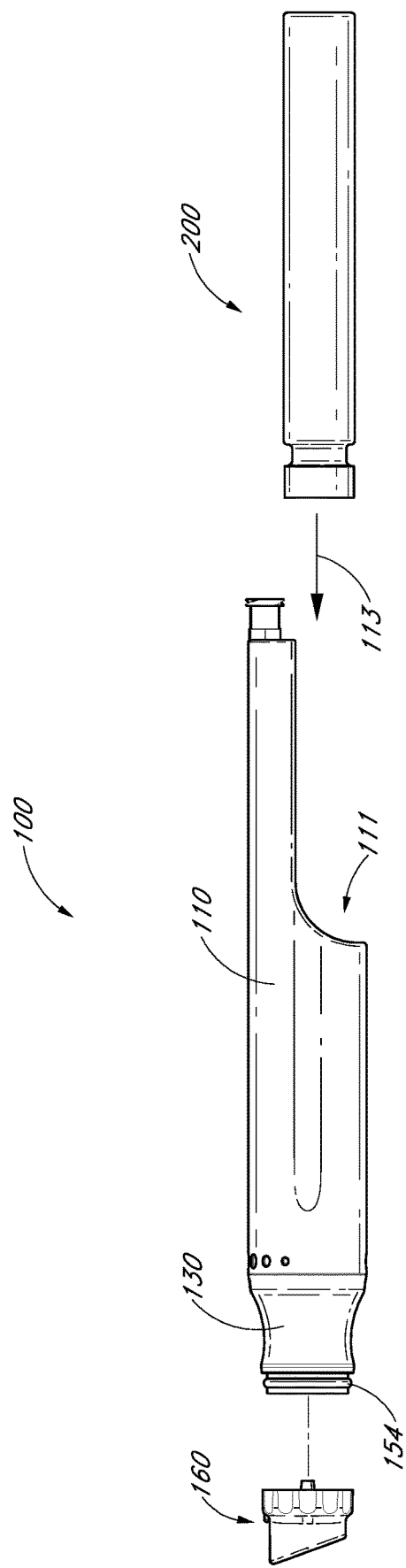
FIG. 2B illustrates an exploded side view of the handpiece assembly of FIG. 1.

With reference to FIGS. 2A and 2B, the handpiece assembly 100 can comprise a recess 111 along the main body portion 110. Such a recess 111 or other region can be sized, shaped and otherwise adapted to receive a cartridge 200. In any of the embodiments described herein, the cartridge 200 can include, without limitation, a standard or non-standard vial, ampoule or any other container. As discussed in greater detail herein, the handpiece assembly 100 can be configured to secure the cartridge 200 or other container within the recess 111 or any other area during use. In some embodiments, serums, other fluids and/or other materials contained within the cartridge 200 can be drawn toward the tip 160 using one or more suction sources (e.g., the vacuum source configured to remove waste materials from the tip 160). In other embodiments, the fluids and/or other materials contained within the cartridge gravity flow toward the tip 160 or are conveyed with the help of a fluid transfer device. The cartridge 200 can be selectively removed from the handpiece assembly 100 when a desired volume or other amount of serum or other material has been delivered to the tip 160.

In other arrangements, two or more different cartridges 200 can be used during a skin treatment procedure. For example, a particular procedure may require the contents (e.g., serums, proteins, brightening or lightening agents, peptides, other fluids or substances, etc.) of two or more different cartridges 200. Thus, a user can load and/or unload a combination of cartridges 200 or other containers within a handpiece assembly 100 during a treatment procedure, either at the same time or sequentially (e.g., one after another). With continued reference to FIG. 2B, the cartridge 200 can be inserted into the recess 111 in a direction generally represented by arrow 113.

FIG. 3A illustrates an exploded perspective view of one embodiment of a handpiece assembly 100 identical or similar to the one depicted in FIG. 1. As shown, the handpiece assembly 100 can comprise a main body portion 110 and an adjustable distal portion 130 rotatably attached thereto. As discussed and illustrated with reference to certain embodiments disclosed herein, rotation of the adjustable distal portion 130 relative to the main portion 110 can advantageously permit a user to regulate the flow of serums, other fluids, materials and/or the like being delivered from the container 200 to the tip 160 of the handpiece assembly 100.

As illustrated in FIG. 3A, the adjustable distal portion 130 of the handpiece assembly 100 can comprise one or more tabs 136 or other protruding members that are configured to align with corresponding recesses 116 or other features of the main body portion 110. In one embodiment, once the tabs 136 of the distal portion 130 are aligned with the recesses 116, the adjustable distal portion 130 can be moved toward the main body portion 110 until the tabs 136 reach a recessed annular ring 118. Consequently, the distal portion 130 can be rotated relative to the main body portion 110 so that the tabs 136 slide or otherwise move within the recessed annular ring 118 of the main body portion 110. Such a feature can help secure the adjustable distal portion 130 to the main body portion 110. As discussed in greater detail herein, rotation of the adjustable distal portion 130 relative to the main body portion 110 can help regulate the flowrate of fluids or other substances from a cartridge 200 to the tip 160 of the handpiece assembly 100. In other arrangements, the main body portion 110 comprises one or more other protruding members or features, and the adjustable distal portion 130 comprises corresponding recessed or other receiving areas or portion. Alternatively, one or more other interconnecting members or features can be used to secure the main body portion 110 to the adjustable distal portion 130.

In the embodiment illustrated in FIG. 3A, the distal portion 130 comprises one or more O-rings 138 or other sealing members to prevent undesirable leaks between the main body portion 110 and the adjustable distal portion 130. Further, the opposite end of the adjustable distal portion 130 can be shaped, sized and otherwise configured to receive a tip 160. In some embodiments, the tips 160 are removable, allowing a user to select between different tip designs, as desired or required by a particular application or use. In alternative arrangements, however, the tip 160 is permanently or semi-permanently attached to the handpiece assembly 100. Further, as shown in FIG. 3A, one or more O-rings 154 or other sealing members can be positioned between a tip 160 and the adjustable distal portion 130 of the handpiece assembly 100.

Figure 3B:
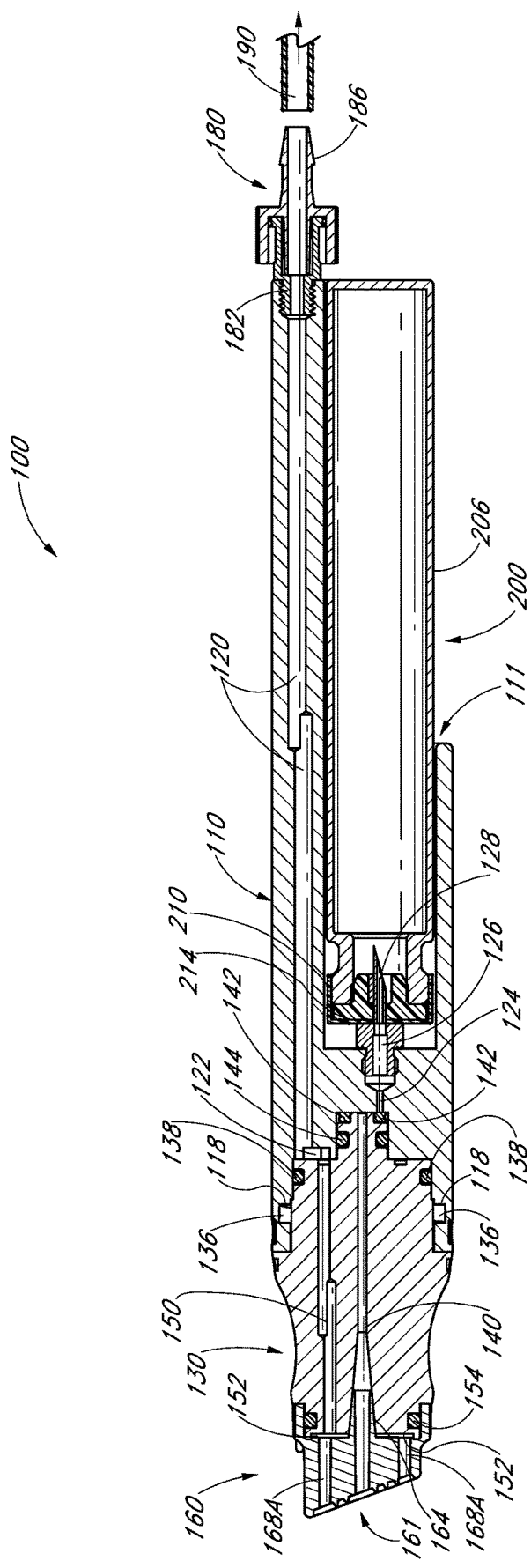
FIG. 3B illustrates a longitudinal cross-sectional view of the handpiece assembly of FIG. 1.

FIG. 3B illustrates a cross-sectional view of the handpiece assembly 100 depicted in FIG. 3A. In the illustrated embodiment, a cartridge 200 has been secured within a recess 111 or other receiving area of the handpiece assembly 100. The size, shape, location and/or other details of the recess 111 can vary, depending on the size of the cartridge 200 that will be inserted therein or as otherwise required or desired. As shown in FIG. 3A, the cartridge 200 can include a main cylindrical portion 206 and a nozzle portion 210. In some arrangements, the nozzle portion 210 comprises a septum 214, membrane or other member that can be pierced, punctured or otherwise compromised to access the interior contents of the cartridge 200 (e.g., serum, other liquids or materials, etc.). The septum 214 can include one or more flexible, rigid and/or semi-rigid materials, such as, for example, rubber, plastic, paper and/or the like.

The cartridge 200 can include one or more suitable materials, such as, for example, glass, metals (e.g., stainless steel), plastic, other synthetic or natural materials and/or the like. In some embodiments, for instance, a nozzle portion 210 comprising aluminum or other metal is crimped onto a glass main cylindrical portion 206 of the cartridge 200. However, the nozzle portion 210 and the main cylindrical portion 206 of the cartridge 200 can comprise any other materials. However, the nozzle portion 210 can be attached to the cylindrical portion 206 using one or more other methods or devices, such as, for example, a threaded connection, snap connection, adhesives, other fasteners and/or the like. In still other embodiments, the cartridge 200 may include more or fewer portions, compartments, features and/or the like, as desired or required.

With continued reference to FIG. 3B, the interior of the recess 111 of the handpiece assembly 100 can comprise a hollow spike 126 or other piercing member. As shown, the spike 126 can be sized, shaped, positioned and otherwise configured to penetrate the septum 214, membrane or other member of a cartridge 200 when a cartridge 200 is pushed sufficiently far within the recess 111. In other embodiments, the spike 126 or other member can be adapted to access an interior portion of a cartridge 200 in one or more other ways. Accordingly, once the cartridge 200 has been properly inserted into the handpiece assembly 100 and the septum 214 of the cartridge 200 has been compromised, the hollow spike 126 can be placed in fluid communication with the interior contents (e.g., human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance, etc.) of the cartridge 200. In other arrangements, as discussed in greater detail herein, the cartridge 200 can comprise water, saline, other dilutants or dissolvents and/or other fluids that can be selectively delivered to the tip 160 to dissolve, dilute and/or otherwise come in contact with one or more solids, granular materials, gels, concentrated solution and/or other substances positioned within, on and/or near the tip or other portion of a handpiece assembly.

In the illustrated embodiment, the spike 126 includes an angled or sloped tip 128 to further facilitate the piercing or puncturing of the cartridge's septum 214 or other sealing member. Although not illustrated herein, the handpiece assembly 100 can include one or more other needles that are configured to penetrate into the interior of a cartridge 200. For example, one or more vent needles can be used to facilitate the removal of fluids and/or other materials from a cartridge 200 which has been loaded into a handpiece assembly 100.

As discussed, the cartridge 200 can be sized, shaped and otherwise configured to snugly or generally snugly fit within the handpiece assembly 100. Therefore, in some arrangements, the cartridge 200 is secured to the handpiece assembly 100 by friction or by the generally tight tolerances of the recess 111 of the handpiece assembly 100. In FIG. 3B, the friction between spike 126 and the septum 214 or other sealing member can help maintain the cartridge 200 within the handpiece assembly 100.

In other embodiments, however, a cartridge 200 can be secured to one or more other portions of a handpiece assembly 100. In addition, the handpiece assembly 100 can include one or more other methods or devices for securing a cartridge 200. For example, the handpiece assembly 100 can include tabs, flanges, other protrusion members and/or any other features or items that help positively engage one or more portions of the cartridge 200 positioned therein. In some embodiments, delivery of a cartridge 200 to a desired depth of the recess 111 or other receiving area of the handpiece assembly 100 can produce an audible click, a positive engagement mechanism and/or the like. Such features can help notify the user that a cartridge 200 has been property secured within the handpiece assembly 100. In other arrangements, a separate device, such as, as a locking cap, strap or other member can be used to ensure that the cartridge 200 remains in fluid communication with the spike 126 and within the recess 111 or other desired receiving location of the handpiece assembly 100 during use.

Figure 4A:
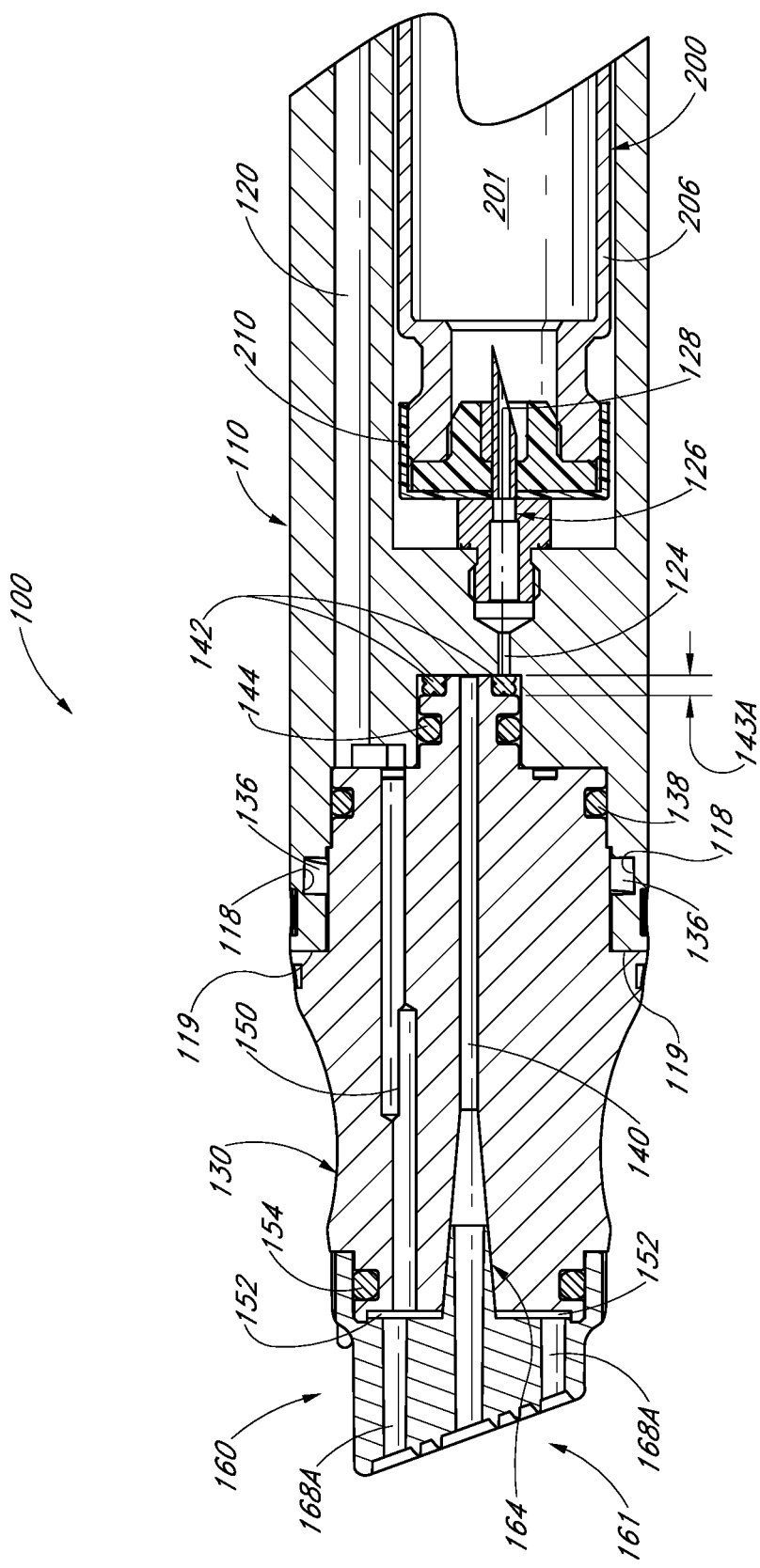
FIG. 4A illustrates a partial cross-sectional view of the handpiece assembly of FIG. 1 with an internal fluid delivery valve in a first position.

FIG. 4A illustrates a cross-sectional view of the handpiece assembly 100 comprising a spike 126 that is in fluid communication with the interior 201 of a cartridge 200. As shown, a delivery conduit 124 can be used to place the spike 126 in fluid communication with an intermediate region or space 142 generally formed between the main body portion 110 and the adjustable distal portion 130. One or more O-rings 144 or other sealing members can be used to ensure that fluid remains within this intermediate region 142. Further, the handpiece assembly 100 can be configured so that a user can selectively modify the size of the intermediate region 142. For example, as illustrated by the differences between FIGS. 4A and 4B, rotation of the adjustable distal portion 130 relative to the main body portion 110 can alter the width 143A, 143B of the intermediate region 142. In some embodiments, rotation of the adjustable distal portion 130 relative to the main body portion 110 causes the two portions 130, 110 to move closer to or further apart from each other, depending on the direction of rotation. Consequently, the width 143A, 143B, and thus the overall size, of the intermediate region 142 can be selectively varied by a user during a treatment procedure, as desired or required.

In some embodiments, the longitudinal axes of the delivery conduit 124 and the spike 126 can be offset (e.g., generally not aligned) with each other. This can permit the width 143A, 143B or other separation distance between the main body portion 110 and the adjustable distal portion 130 to be selectively varied. As discussed in greater detail herein, this can help modify the hydraulic characteristics of fluids and/or other materials being conveyed from the spike 126 to the delivery conduit 124, and thus, from a cartridge 200 or other fluid source to the tip 160 of the handpiece assembly 100. In some embodiments, the longitudinal axes of the delivery conduit 124 and the spike 126 remain offset as the adjustable distal portion 130 is rotated or otherwise moved relative to the main body portion 110.

In the illustrated embodiment, the distance between the recessed annular ring 118 of the main body portion 110 and the interface 119 between the main body portion 110 and the adjustable distal portion 130 varies depending on the circumferential position of the annular ring 118. In other words, by rotating the adjustable distal portion 130 relative to the main body portion 110, the distance between these portions 130, 110 can be selectively adjusted.

With continued reference to FIG. 4A, the adjustable distal portion 130 can include a delivery channel 140 or other conduit that places the intermediate region 142 in fluid communication with the tip 160. However, in order for serums or other materials to be delivered from the intermediate region 142 to the tip 160, a fluid path must be created between the intermediate region 142 and the delivery channel 140 through the adjustable distal portion 130. In FIG. 4A, there is little or no space between the distal portion 130 and the main body portion 110. Therefore, fluids or other materials will be prevented or severely limited from flowing from the intermediate region 142, and thus the cartridge 200, to the tip 160 of the handpiece assembly 100.

Figure 4B:
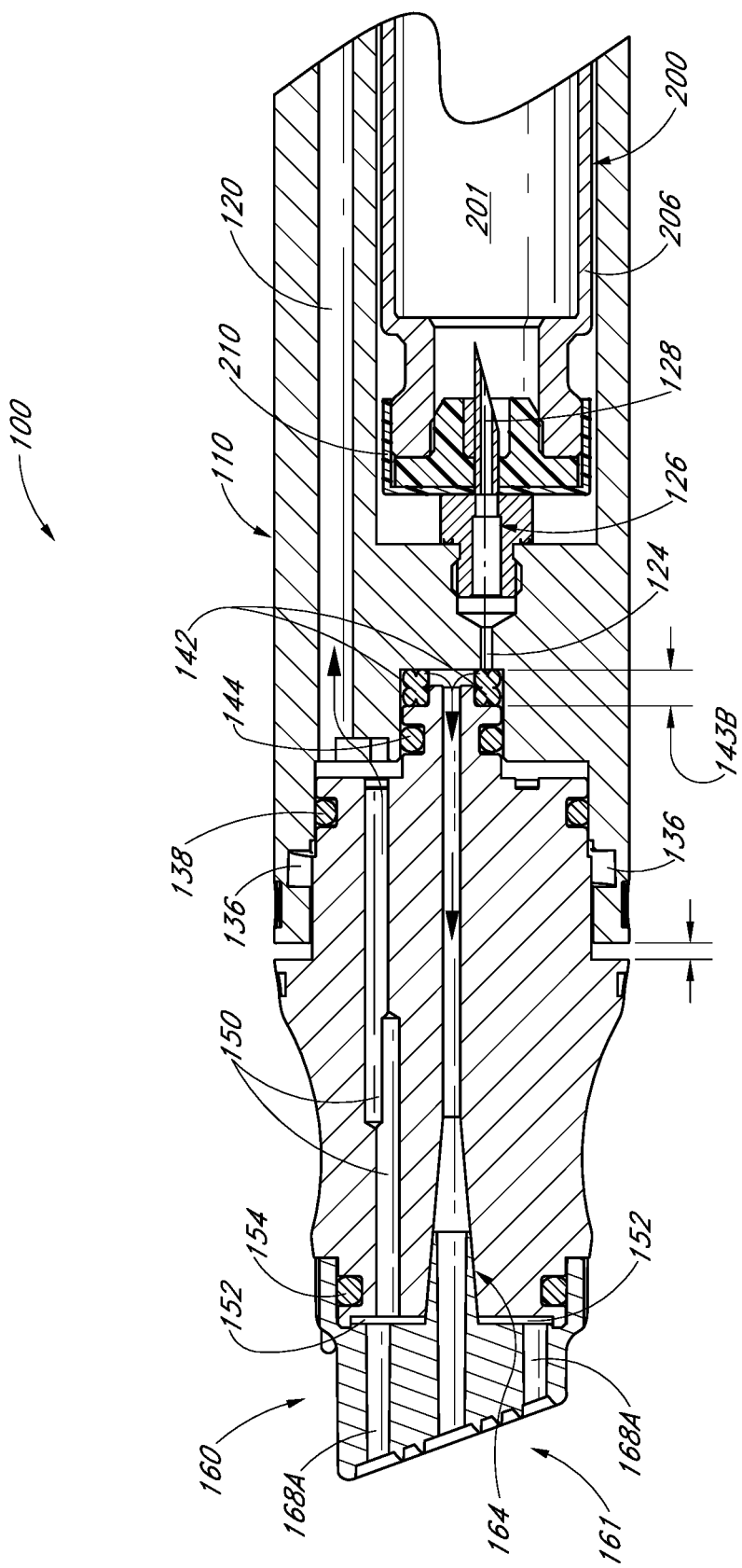
FIG. 4B illustrates a partial cross-sectional view of the handpiece assembly of FIG. 1 with an internal fluid delivery valve in a second position.

Alternatively, as illustrated in FIG. 4B, when sufficient separation exists between the adjacent surfaces of the adjustable distal portion 130 and the main body housing 110, a flow path is created from the intermediate region 142 to the delivery channel 140 of the distal portion 130. Accordingly, serums and/or other fluids or materials can be conveyed from the cartridge 200 toward the tip 160 of the handpiece assembly 100. Accordingly, by rotating the adjustable distal portion 130 relative to the main body housing 110, as discussed herein, the flowrate of liquids and/or other materials from the cartridge 200 toward the tip 160 can be selectively regulated.

With continued reference to FIGS. 1 and 3A, the adjustable distal portion 130 can include a setting indicator 132 along its exterior surface, near the interface of the adjustable distal portion 130 and the adjacent main body portion 110. Likewise, the main body portion 110 can include a plurality of corresponding markers 112A-112D with which the indicator 132 of the distal portion 130 can align. In the illustrated embodiment, the main body portion 110 comprises a total of four markers 112A-112D, each corresponding to a different flowrate setting through the handpiece assembly 100. However, a handpiece assembly 100 can include more or fewer indicators 132 and/or markers 112A-112D, as desired or required by a particular application or use. As discussed, rotation of the adjustable distal portion 130 relative to the main body portion 110 can vary the distance between the two portions 110, 130. Thus, the flow path for serums and/or other fluids or materials through the handpiece assembly 100 can be adjusted.

In the embodiment illustrated in FIGS. 1 and 3A, the markers 112A-112D along the outside of the main body portion are generally circular in shape. Further, the diameter of each of the markers 112A-112D varies depending on the relative flowrate through the handpiece assembly 100 to which each marker corresponds or relates. For example, in some embodiments, the larger markers represent a greater separation distance between adjacent surfaces of the adjustable distal portion 130 and the main body portion 110, and thus, a relatively higher flowrate of fluids and/or other materials from the cartridge 200 through the handpiece assembly 100 to the tip 160. As shown, the handpiece assembly 100 can be configured so that a user selects a flowrate setting by aligning the setting indicator 132 on the distal portion 130 with the desired marker 112A-112D on the main body portion 110. In accordance with the arrangements disclosed herein, this can be accomplished by rotating the adjustable distal portion 130 relative to the main body portion 110.

However, a handpiece assembly 100 can include one or more other methods of selecting a desired flowrate of fluids and/or other materials therethrough. For example, in some embodiments, the handpiece assembly 100 includes one or more dials, knobs, buttons and/or other devices or features for adjusting the flowrate. Such controllers can be graduated so as to permit a user to select a specific flowrate or relative flow setting (e.g., "HIGH," "MEDIUM," "LOW," etc.). In other arrangements, the handpiece assembly 100 comprises a display (e.g., LED, LCD, etc.) that is adapted to provide information regarding a current flowrate or setting. Further, such a display can be configured to permit users to make flowrate adjustments (e.g., touchscreen display). Further, selection devices or features (e.g., knobs, buttons, dials, etc.) and/or displays can be positioned on the handpiece assembly 100. Alternatively, the controllers can be separate from the handpiece assembly. For example, such devices or features can be connected to the assembly through one or more hardwired and/or wireless connections (e.g., cable, Ethernet line, radio frequency, Bluetooth, Wi-Fi, etc.).

In other embodiments, a handpiece assembly 100 includes one or more different methods and/or devices for controlling the flowrate of fluids or other materials from a cartridge 200 toward the tip 160. For example, the handpiece assembly 100 can comprise different types of flow control valves or devices than those disclosed herein. Regardless of the exact flow control method or device used, it may be desirable to provide users with the ability to selectively regulate the rate at which serums, other fluids or materials and/or the like are delivered from a cartridge 200 to the tip 160 of the handpiece assembly 100. This can further enhance a particular skin treatment procedure by allowing a desired volume of fluids or other materials to be delivered to the treatment surface (e.g., skin-tip interface). For instance, during the initial exfoliation phase, a relatively high volume of serum or other lubricating fluids may be desired. However, during subsequent stages of a treatment procedure, a reduced flowrate of fluids and/or other substances may be desired or required.

With continued reference to FIG. 3B, the tip 160 can include an internal delivery stem 164 or other conduit that is configured receive fluids and/or other substances from the delivery channel 140 of the adjustable distal portion 130 and convey them to the distal end 161 of the tip 160. As illustrated in FIGS. 3B, 4A and 4B, the internal stem 164 of the tip 160 can be sized, shaped and otherwise configured to be in fluid communication with the delivery channel 140 extending through the interior of the distal portion 130. In some embodiments, a handpiece assembly 100 includes two or more internal delivery channels 140 or other conduits through which fluids and/or other materials may be conveyed. Likewise, the tip 160 can include additional delivery stems 164 or other conduits configured to transfer fluids and/or other materials toward the distal end 161 of the tip 160.

As depicted in FIG. 3B, the tip 160 can include one or more removal conduits 168A. According to certain embodiments, such conduits 168A are also in fluid communication with the distal end 161 of the tip 160. The removal conduits 168A can be advantageously sized, shaped, located and otherwise configured to transfer exfoliated skin, spent serums and other waste materials away from the treatment surface. In some arrangements, a tip 160 comprises a plurality of removal conduits 168A located at or near the tip periphery. However, in other embodiments, the quantity, spacing, location and other details of the removal conduits 168A can vary, as desired or required by a particular application or use.

With continued reference to the cross-sectional views of FIGS. 3B, 4A and 4B, exfoliated skin, spent serums, other fluids and/or any other materials can be transferred from the distal end 161 of the tip 160 to a common collection area 152 located at or near a proximal end of the tip 160. According to some embodiments, the collection area 152 is positioned at or near the location where the tip 160 attaches to the adjustable distal portion 130. Accordingly, exfoliated skin, spent or waste fluids and/or other materials can be delivered into one or more removal channels 150 of the distal portion 130. In addition, the main body portion 110 can include one or more waste channels 120 or conduits that are configured to be in fluid communication with the removal channels 150 of the distal portion 130. In the depicted embodiments, a cavity 122 or other common area is used to place the channels 120 of the main body portion 110 in fluid communication with the removal channels 150 of the distal portion 130. Such a cavity or other common area can be located at or near the interface of the adjacent portions 110, 130 of the handpiece assembly 100. Further, the cavity 122 can be advantageously configured to maintain the waste channel 120 in fluid communication with the removal channel 150 throughout the entire range of relative movement between the main body portion 110 and the adjustable distal portion 130. As shown, the cavity 122 or other common area can comprise an annular region that completely or partially extends around an interior portion of the handpiece assembly 100.

In some embodiments, the main body portion 110 of the handpiece assembly 100 includes a discharge nozzle 180 or port. As illustrated in FIG. 3B, the nozzle 180 can include a threaded portion 182 that attaches to the handpiece assembly 100. The nozzle can further include a fitting generally opposite of the threaded portion 182 that is shaped, sized and otherwise configured to receive tubing 190 or some other fluid line or conduit. The nozzle 180 can comprise a different shape, size or general design than illustrated in FIG. 3B. In addition, the nozzle 180 can be adapted to connect to the handpiece assembly 100 and/or tubing 190 (or fluid conduits) using other methods or devices. For example, the nozzle 180 can form a generally uniform structure with an adjacent portion of the handpiece assembly 100. According to another arrangement, the nozzle 180 includes a quick-connect fitting to facilitate connection to and/or removal from a waste conduit (e.g., rubber or other flexible tubing, hose or other line). Regardless of its exact shape, size, method of attachment and/or other characteristics or details, the nozzle 180 can be advantageously configured to place the handpiece assembly 100 in fluid communication with a vacuum or other suction source (e.g., via the tubing 180 or other conduit) that can selectively remove exfoliated skin, spent serums other fluids and/or any other materials away from the skin surface being treated.

According to some embodiments, the conduit 190 or other channel (e.g., flexible tubing or hose) to which the handpiece assembly 100 connect are in fluid communication with a vacuum or other suction source (e.g., pump, other fluid transfer device, etc.). Thus, exfoliated skin, spent fluids and/or other waste materials can be transported away from the distal end 161 of the tip 160 to a canister (not shown) or other waste source. The rate of transfer of such waste materials can depend on one or more factors, such as, for example, the setting of the vacuum or suction source, the characteristics (e.g., diameter, length, smoothness, etc.) of the various conduits or channels 168A, 150, 120, 180, 190 through which the waste materials are conveyed, the viscosity, density and other fluid properties of the waste materials and/or the like.

Figure 4C:
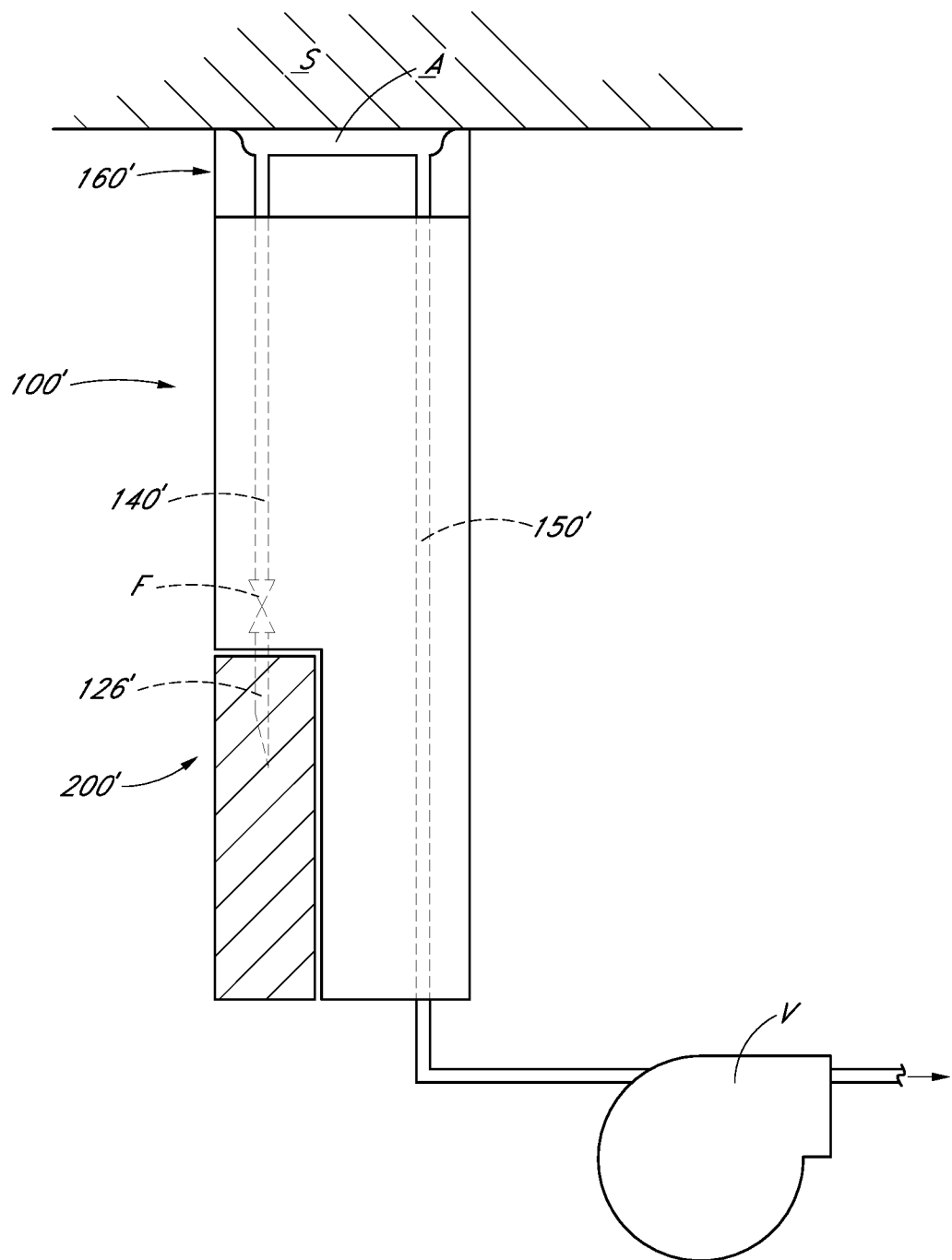
FIG. 4C schematically illustrates a handpiece assembly which comprises a cartridge and which is in fluid communication with a vacuum source according to one embodiment.

FIG. 4C schematically illustrates one embodiment of a handpiece assembly 100' which comprises a cartridge 200' and which is in fluid communication with a vacuum V or other suction source. In the depicted arrangement, the vacuum V is configured to remove waste materials from the tip 160' and help deliver serums, other fluids and/or any other materials from the cartridge 200' to the tip 160'. When the tip 160' is positioned against the skin S being treated, suction created by the vacuum source V can be transmitted to the delivery channel 140' of the assembly 100'. In some embodiments, such a suction force within the delivery channel 140' remains intact as long as the tip 160' is maintained against or substantially against the skin S. Consequently, the suction force can be transferred to the delivery channel 140' via an enclosed or substantially enclosed area A near the working surface of the tip 160'.

With continued reference to FIG. 4C, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents (e.g., kojic acid), peptides, peeling agents, acids, anesthetics, medicants, other non-active or active compounds, other fluids or materials, combination or mixtures thereof and/or any other substance situated within a cartridge 200' can be placed in fluid communication with the delivery channel 140' using a spike 126' or other member. A valve F or other flow control device or mechanism can be used to regulate the rate at which such fluids and/or other materials are transferred to the tip 160'. For example, the handpiece assembly 100' can comprise a main body portion that is movable (e.g., rotatable) relative to a distal portion as disclosed herein with reference to FIGS. 1-3B and 5A. As discussed, the relative movement of these portions can help regulate the flowrate of serums, other fluids and/or other materials from the cartridge 200' to the tip 160' of the handpiece assembly 100'. In alternative embodiments, as discussed in greater detail herein, the delivery channel 140' can be configured to convey water, saline, other dilutants or dissolvents and/or other fluids from the cartridge 200' to the tip 160'. Accordingly, solid materials, gels, other concentrated materials and/or other substances positioned on or near the tip 160' can be advantageously mixed or combined with these fluids to produce a desired and/or required effect.

In other embodiments, however, the contents of a container 200' are transferred to the tip 160' using one or more other methods or devices, either in addition to or in lieu of the methods discussed herein with reference to FIG. 4C. For example, the handpiece assembly 100' can comprise an internal pump or other fluid transfer device that is configured to convey serums, other fluids and/or other materials from the cartridge 200' to the tip 160'. In other embodiments, the internal contents of the cartridge 200' are configured to, at least partially, gravity flow toward the tip 160' of the assembly 100'. One or more other ways of transferring fluids and other materials to the tip 160' of the handpiece assembly 100' can be used, either in lieu of or in combination with methods and devices disclosed herein.

In any of the embodiments of a handpiece assembly disclosed herein, including but not limited to those illustrated and discussed with reference to FIGS. 1, 2A, 2B, 3A, 3B, 4A-4C, 5A-5C, 7, 14A, 16A, 17, 18A, 18B, 19A, 19B, 20A-20D, 21A and 21B, or variations thereof, the direction of flow through the various channels, conduits and/or other hydraulic components of the tip, handpiece assembly and other components of a skin treatment system can be reversed. By way of example, in the arrangement shown in FIGS. 1-4B, the handpiece assembly 100 can be differently configured so that spent fluids, exfoliated skin, debris and other waste materials are removed away from the skin through a centrally located opening in the tip (e.g., the delivery stem 164) and/or a centrally located channel (e.g., the delivery channel 140) of the handpiece assembly 100. In such embodiments, one or more of the fluid channels, connectors and/or other fluid lines may need to be reconfigured to adequately place the centrally-located removal opening of the tip in fluid communication with a vacuum or other suction source, as desired or required.

Further, the serums, other fluids and/or other materials can be delivered to the tip 160 (e.g., from a cartridge, an external source, etc.) through one or more peripheral or other non-centrally located channels, conduits and/or other lines or fittings. For instance, in the handpiece assembly 100 illustrated in FIGS. 1-4B, such fluids and/or other materials can be routed through channels 150 of the assembly and/or waste conduits 168A of the tip 160. Thus, one or more of the channels, connectors and/or other hydraulic components may need to be reconfigured to adequately place the non-centrally located delivery openings of the tip in fluid communication with corresponding delivery lines of the handpiece assembly 100.

Accordingly, in any of the embodiments disclosed herein, water (e.g., distilled, tap water, sterile, filtered, etc.), saline, serums, growth factors, other dilutants, other solutions, mixtures or fluids and/or the like can be delivered to the tip through one or more centrally and/or non-centrally located (e.g., peripheral, offset, etc.) openings. Thus, the flow pattern of such fluids and/or other materials across the tip (e.g., from the tip inlet to the tip outlet) can be advantageously controlled as desired or required for a particular application or use. For instance, in some embodiments, it may be desirable to introduce fluids and/or other materials through one, two or more peripheral or non-centrally located openings (e.g., 572A, 572B) of a tip (e.g., 560 of FIG. 8A), and to collect the spent fluids, removed skin, other debris and other waste materials through a centrally-located opening (e.g., 570).

Figure 5A:
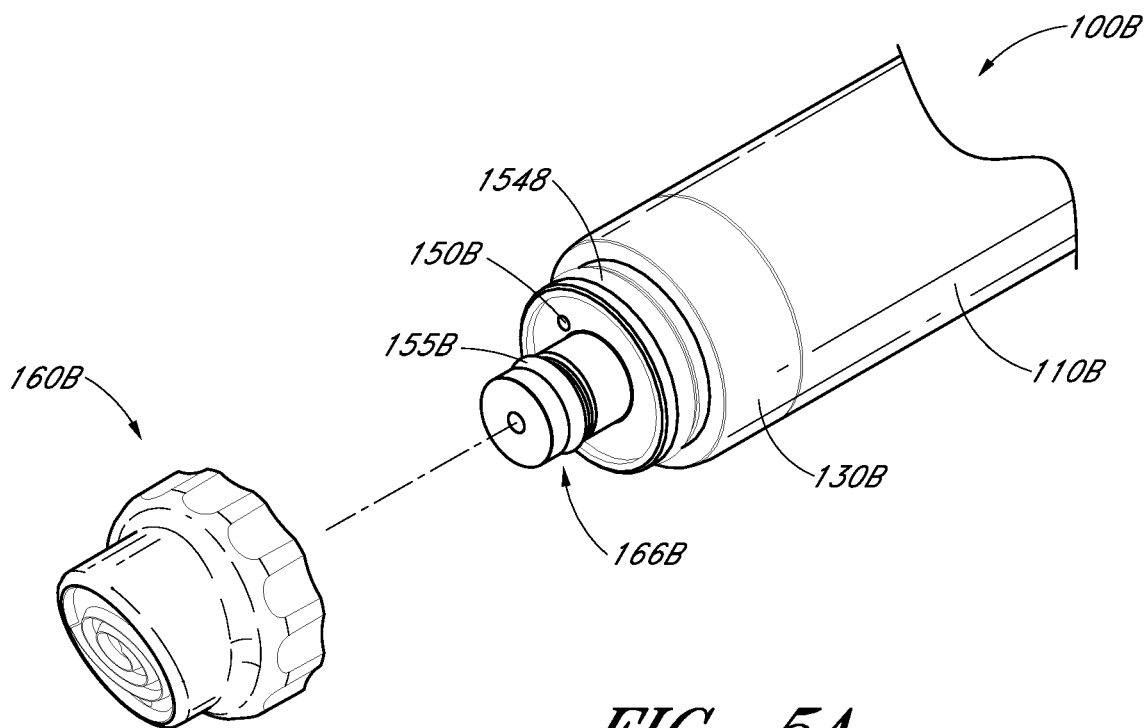
FIG. 5A illustrates an exploded perspective view of a handpiece assembly according to another embodiment.

FIG. 5A illustrates a partial exploded view of another embodiment of a handpiece assembly 100B. As with the arrangement of FIG. 3A, the depicted handpiece assembly 100B can be configured to receive a removable tip 160B along its distal end. Further, as with other embodiments discussed and illustrated herein, the handpiece assembly 100B can include an adjustable distal portion 130B that is selectively movable (e.g., rotatable) relative to the adjacent main body portion 110B. Such relative rotation or other movement can advantageously permit a user to regulate the flow of serums, chemical exfoliation compounds or mixtures, antioxidants, growth factors, lotions, vitamins, medicants, brightening or lightening agents, peptides, peeling agents, acids, other active or non-active agents, water (e.g., distilled, tap water, filtered, sterile, etc.), saline, other dilutants, other fluids or materials and/or the like being delivered to the tip 160B of the handpiece assembly 100B.

Figure 5B:
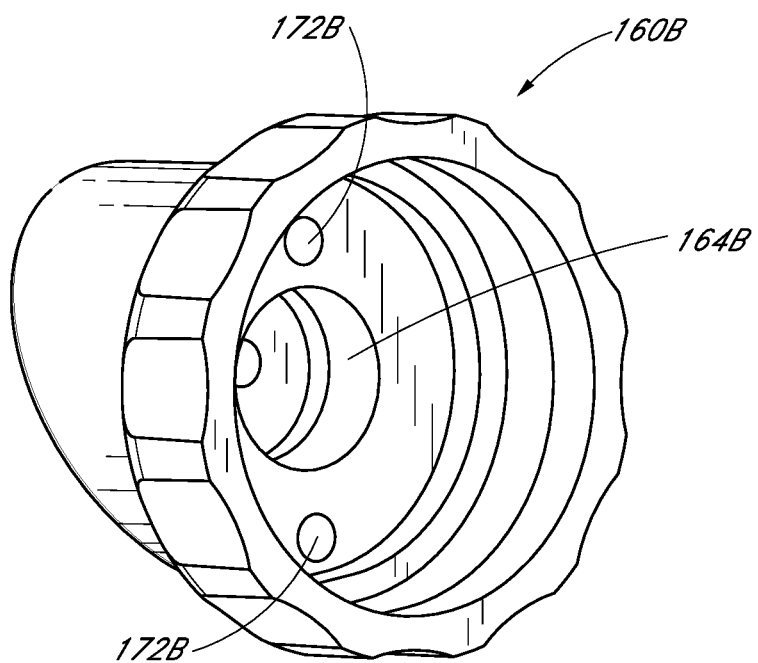
FIG. 5B illustrates a bottom perspective view of one embodiment of a tip configured to be secured to the handpiece assembly of FIG. 5A.

In FIG. 5A, the adjustable distal portion 130B of the handpiece assembly 100B comprises a nozzle 166B or other member that helps place the tip 160B in fluid communication with a vacuum source and/or a fluid delivery source. In some embodiments, the tip 160B is advantageously designed to receive or otherwise accommodate the nozzle 164B. For example, as illustrated in FIG. 5B, an interior portion of the tip 160B can include a recess 164B that is shaped, sized and otherwise configured to receive the nozzle 166B of the adjustable distal portion 130B. As shown, the handpiece assembly 100B and/or the tip 160B can include one or more O-rings 154B, 155B, gaskets and/or other sealing members or devices to help reduce or eliminate the likelihood of leaks as fluids and other materials are transferred between the handpiece assembly 100B and the tip 160B. The tip 160B can be secured to the distal end of the handpiece assembly 100B using a friction connection, a threaded connection, a snap connection, another type of mechanical connection and/or any other type of attachment device or method.

Such configurations in which the distal end of a handpiece assembly comprises a nozzle, fitting or other protruding member that is adapted to be secured within a corresponding recess, other feature or other area of the tip can be incorporated into any of the handpiece assembly and/or tip embodiments disclosed herein, or variations thereof. As discussed in greater detail herein, such a nozzle-recess connection can be configured to place the tip in fluid communication with either a suction source or a fluid delivery source, as desired or required. One or more additional openings, conduits, channels and/or other hydraulic components in the tip and/or the handpiece assembly can be configured to transfer fluids and/or materials to and/or from the tip.

Figure 5C:
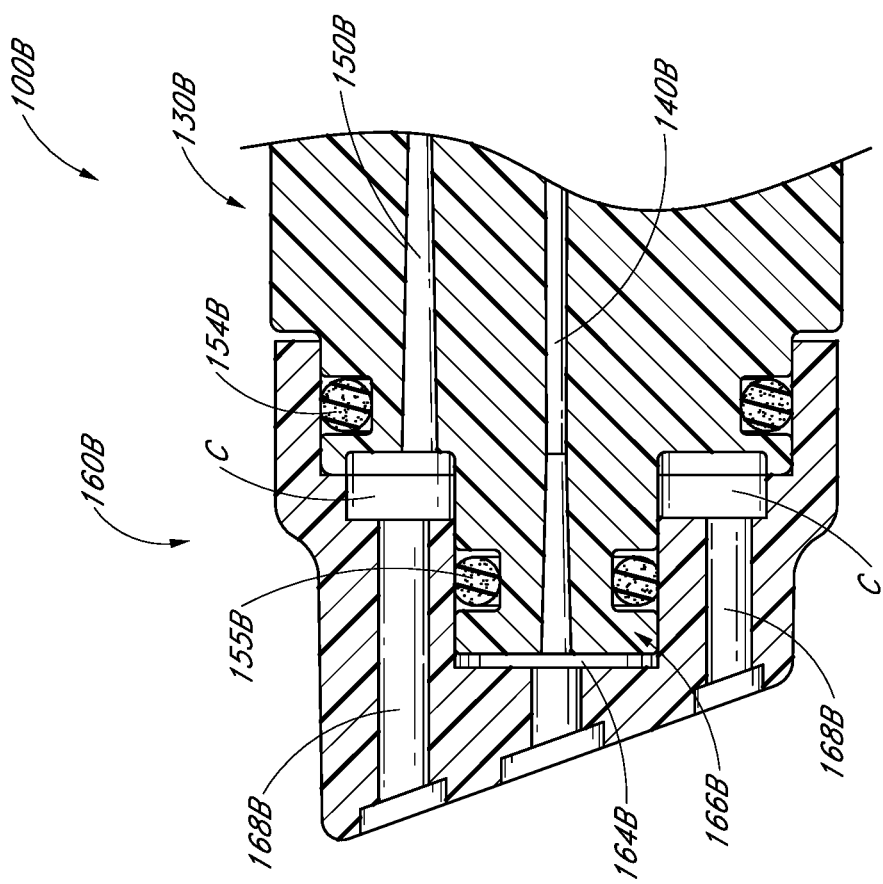
FIG. 5C illustrates a cross-sectional view of the handpiece assembly and the tip of FIG. 5A.

With reference to the cross-sectional view of FIG. 5C, once the tip 160B has been properly secured to the handpiece assembly 100A (e.g., to the adjustable distal portion 130B), the distal end of the tip 160B can be placed in fluid communication with one or more delivery channels 150B and/or waste channels 140B of the handpiece assembly 100B. For example, in the embodiment depicted in FIG. 5C, serums, water (e.g., distilled, tap water, filtered, etc.), other dilutants, other fluids or materials and/or the like can be delivered to the tip 160 through a delivery conduit 150B of the handpiece assembly 100B, through a common area C (e.g., located between the tip 160B and the adjustable distal portion 130B of the handpiece assembly 100B) and through two peripherally located delivery conduits 168B of the tip 160B. In addition, waste materials can be removed from the tip through a centrally-located opening and recess 164B of the tip 160B and a waste channel of the handpiece assembly 100B. However, as discussed, in alternative embodiments, the direction of flow through such channels, conduits and/or other hydraulic components of the tip 160B and/or the handpiece assembly 100B can be reversed or otherwise varied, as desired or required.

FIG. 6A illustrates a side view of one embodiment of a cartridge 300 configured to be secured within or onto a handpiece assembly as disclosed herein. The cartridge 300 can include a main cylindrical portion 306 and a nozzle portion 310 or closure. As illustrated in FIG. 6C, the closure 310 can comprise a septum 314, membrane or other member that can be pierced, punctured or otherwise compromised to access the interior contents of the cartridge 300 (e.g., serum, other liquids or materials, etc.). In some embodiments, for example, the septum 314 or other member is adapted to be selectively pierced or punctured by a hollow spike, needle or similar device when the cartridge 300 is inserted into the handpiece assembly. As discussed, the septum 314 can include one or more flexible materials, such as, for example, rubber, plastic, paper and/or the like.

For any embodiments of a cartridge, vial or other container disclosed herein, the septum 314, membrane or other surface configured to be pierced, punctured or otherwise compromised can be re-sealable. In other words, such a septum 314 can be adapted to re-seal the internal contents of the cartridge 300 when the cartridge is removed from the handpiece assembly. Therefore, leakage of serums, other fluids and/or other materials contained within a cartridge can be reduced or prevented. In addition, the septum 314 can help ensure against contamination of the internal contents by preventing one or more materials from entering the cartridge.

As discussed, cartridges configured to be secured within a handpiece assembly can include any combination of serums, human growth factors, cytokines, collagen, brightening or lightening agents, peptides, peeling agents, acids, antioxidants, matrix proteins, saline, water (e.g., distilled, tap water, filtered, etc.) and/or other liquids or substances, as desired or required by a particular application or use. In certain embodiments, a treatment protocol may require the use of one, two or more different cartridges for a specific procedure. Thus, cartridges can be removed from or inserted into a handpiece assembly prior to or during a particular procedure.

Another embodiment of a cartridge 400 that is sized, shaped and otherwise configured for placement within a handpiece assembly is illustrated in FIG. 6B. As shown, the cartridge 400 can include a tip 410 and a main tubular portion 406. With reference to the front view of FIG. 6D, at least a portion of the end surface 414 of the tip 410 can include one or more septa, membranes or other layers or members that are configured to be pierced, punctured or otherwise compromised by a spike or other protruding member when the cartridge 400 is secured in a handpiece assembly.

With continued reference to FIG. 6B, the cartridge 400 can include an internal channel 420 that is adapted to be in fluid communication with a tubular spike or other protruding member of the handpiece assembly when a surface 414 of the cartridge 400 is pierced or punctured (e.g., when the cartridge 400 is properly inserted within a handpiece assembly). In some embodiments, as illustrated in FIG. 6B, the cartridge 400 includes a nozzle 430 or other fitting that is sized, shaped and otherwise configured to receive or connect to a fluid line 450 or other conduit. For example, in the depicted arrangement, the nozzle 430 includes a port 438 to which tubing or some other fluid conduit 450 can attach. In some embodiments, the nozzle 430 is secured to the cartridge 400 using a threaded connection 434. However, one or more other types of methods or devices can be used to join the nozzle 430 to the cartridge 400. In other embodiments, the cartridge 400 and the nozzle 430 form a generally unitary structure (e.g., molded as a single member).

A cartridge 400, such as the one illustrated in FIG. 6B, can advantageously permit a user to deliver human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance to a handpiece assembly from one or more external fluid sources. For example, in some embodiments, the conduit 450 to which the cartridge 400 is connected, is placed in fluid communication with one or more containers. Such containers can comprise the desired serums, human growth factors, cytokines, collagen, antioxidants, matrix proteins, brightening or lightening agents, peptides, peeling agents, acids, medicants, other fluids or substances, combinations thereof and/or the like, as desired or required by a particular treatment. Thus, the cartridge 400 can be used as an interface between the handpiece assembly and a relatively larger source of treatment media. For example, the cartridge 400 can be placed in fluid communication with a multi-container system such as the one disclosed in U.S. patent application Ser. No. 11/392,348, filed on Mar. 29, 2006 and published on Jul. 5, 2007 as U.S. Publication 2007/0156124, the entirety of which is hereby incorporated by reference herein.

According to certain arrangements, a cartridge 400 includes one or more solids, granular materials, gels, concentrated fluids and/or other substances that are adapted to dissolve, dilute, soften or otherwise mix when contacted by water, saline, other dilutants or dissolvents and/or other fluids. Thus, such materials or other substances can be placed within the cartridge 400 in one or more forms, such as, for example, as powder, granular material, a tablet, a capsule, a pill, other dissolvable solid, a concentrated solution, a gel and/or the like. In other embodiments, such solids, gels and/or other materials can be situated on the tip or other portion of the system (e.g., within a post or recess, adhered to one or more other exposed or hidden surfaces, within a removable cartridge upstream of the handpiece assembly as illustrated, for example, in FIG. 18A, etc.), impregnated into a foam pad or other member (see, as depicted in FIGS. 19A, 19B and 20A-20C) and/or at any other location. Regardless of their exact composition, location and/or other details, such materials and/or other substances can be configured to dissolve, dilute and/or otherwise mix with water, saline and/or other fluids being conveyed through the cartridge 400.

As discussed, in any of the embodiments of the cartridge (e.g., vial, ampoule, other standard or non-standard container, etc.) disclosed herein, the cartridge can be configured to releasably lock or otherwise secure to one or more portions of a handpiece assembly (e.g., recess). In other embodiments, a cartridge includes threads, tabs, slots and/or other features that are configured to engage corresponding portions of the handpiece assembly. In alternative arrangements, the cartridge is adapted to remain within a receiving portion of the handpiece assembly by friction or some other mechanism or feature, as desired or required.

Figure 7:
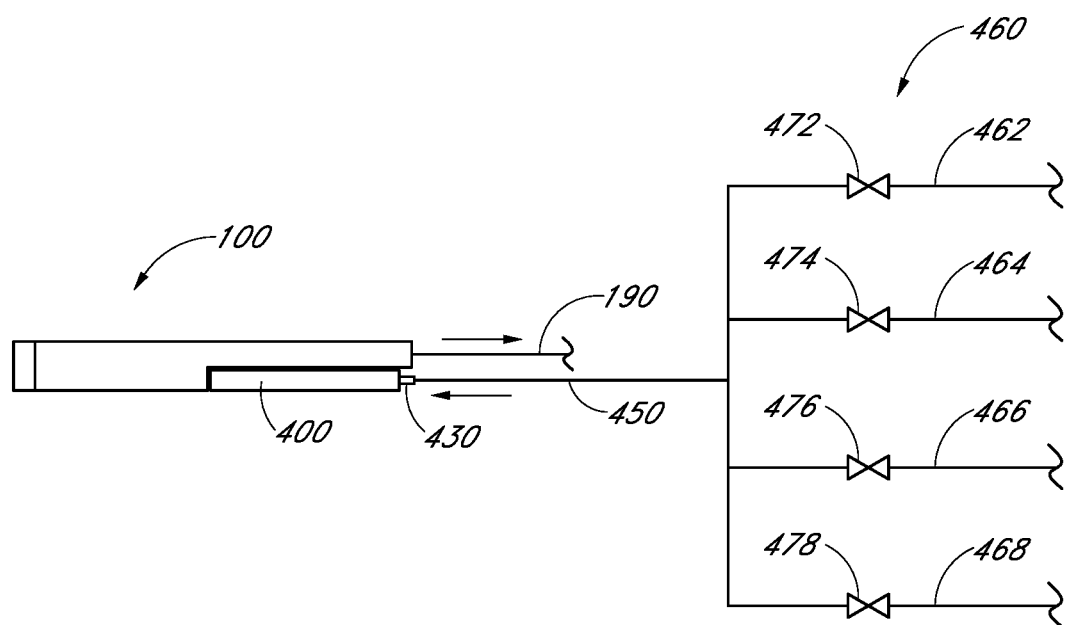
FIG. 7 schematically illustrates the cartridge of FIG. 6B positioned within a handpiece assembly and being in fluid communication with a fluid delivery system according to one embodiment.

According to certain embodiments, as illustrated in FIG. 7, the cartridge 400 is placed in fluid communication with a manifold system 460 that may comprise a plurality of individual fluid lines 462, 464, 466, 468. In turn, one or more of these fluid lines 462, 464, 466, 468 can be in fluid communication with a separate container (not shown). In the illustrated embodiment, all the individual fluid lines 462, 464, 466, 468 feed into the main fluid line 450, which connects to the nozzle 430 of the cartridge 400. One or more of the fluid lines 450, 462, 464, 466, 468 can comprise a valve 472, 474, 476, 478 or other flow control device or feature to selectively regulate the transfer of fluids and/or other materials to the handpiece assembly 100. In the illustrated arrangement, the manifold system 460 comprises a total of four fluid branches 462, 464, 466, 468. However, a system can comprise more or fewer fluid branches, as desired or required by a particular application.

According to certain embodiments, one or more of the fluid lines fluid lines 450, 462, 464, 466, 468 of the system schematically illustrated in FIG. 7 are configured to provide water (e.g., distilled, tap water, filtered, etc.), saline, other dilutants or dissolvents, other fluids and/or the like to the handpiece assembly 100. As discussed in greater detail herein, such fluids can be adapted to contact and dissolve, dilute, liquefy, soften and/or otherwise mix with one or more solids, gels and/or other materials positioned within or on various surfaces or portions of the handpiece assembly 100 (e.g., tip). This can provide a convenient method of providing one or more materials at the skin-tip interface and/or any other location where such materials are desired or required.

FIGS. 8A-8F illustrate different views of one embodiment of a removable tip 560 configured for placement on a handpiece assembly as disclosed herein. As shown, the tip 560 can include a tip body portion 563 and a tip skirt portion 562 extending along the bottom of the tip body portion 563. According to certain embodiments, the skirt portion 562 includes a plurality of gripping members or other features (e.g., recesses, protrusions, etc.) to facilitate the handling of the tip 560.

With reference back to the exploded perspective view of FIG. 3A, a tip 160 can be configured to slidably connect to the distal end of a handpiece assembly 100 (e.g., the end of the adjustable distal portion 130). For example, in some embodiments, the tip 160 is adapted to be press fit onto the handpiece assembly 100. As illustrated in FIG. 3A, one or more O-rings 154 or other sealing members can be used between adjacent surfaces of the tip 160 and the handpiece assembly 100 to prevent or reduce the likelihood of undesirable leaks or pressure (e.g., positive, negative or vacuum, etc.). In other embodiments, a tip 160 is removably secured to a handpiece assembly 100 using any other method or device, such as, for example, a threaded connection, interlocking tabs, flanges, members, other fasteners, other mechanical devices and/or the like. In other arrangements, the tip 160 is permanently or semi-permanently attached to the handpiece assembly 100.

In the embodiment illustrated in FIGS. 8A-8F, the tip 560 comprises one or more surfaces along its distal end 561 that are configured to treat (e.g., exfoliate) skin. Any of the embodiments of a tip disclosed herein, including but not limited to those illustrated in FIGS. 1-21B, tip designs incorporated by reference or any other tip designs, or variations thereof, can include one or more abrasive elements configured to treat skin. In addition, such tips can include one or more treatment elements, either in addition to or in lieu of abrasive elements. As used herein, "abrasive element" is a broad term and includes, without limitation, protruding elements, abrasive materials (e.g., grit, sandpaper-like material, other coarse materials, etc.), roughened surfaces, contoured surfaces, surfaces with openings, recesses or other features, brushes, blades, surfaces impregnated with diamonds or other materials and/or the like. Further, as used herein, "treatment element" is a broad term and includes, without limitation, an abrasive element, massage elements or features, elements or features configured to moisturize or apply one or more treatment agents or fluids, polishing or soothing elements or features and/or the like.

Figure 8A:
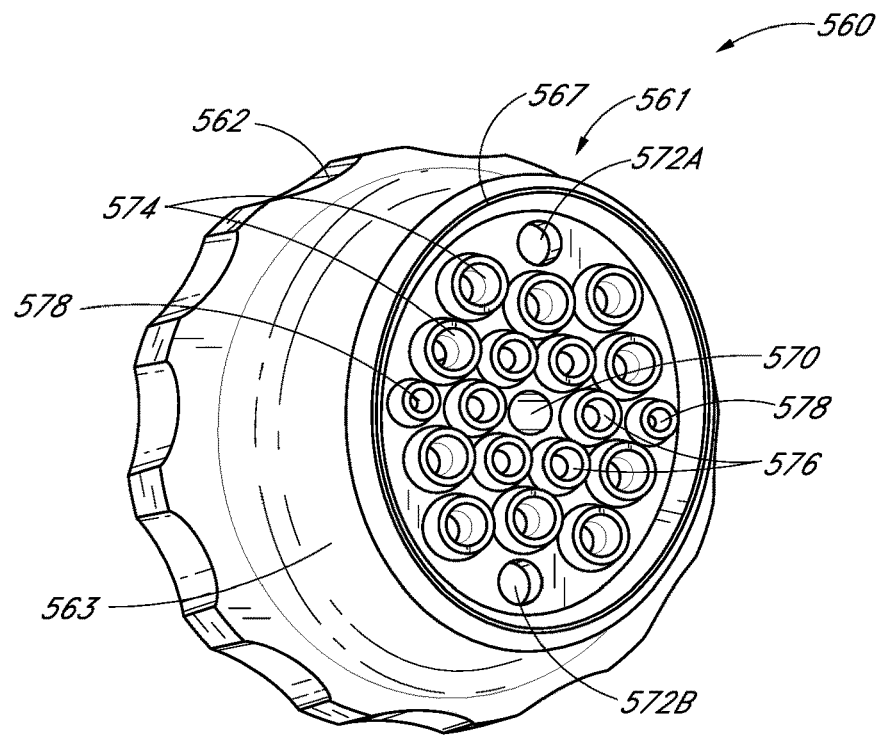
FIG. 8A illustrates a top perspective view of one embodiment of a removable tip configured to be placed along the distal end of a handpiece device.
Figure 8B:
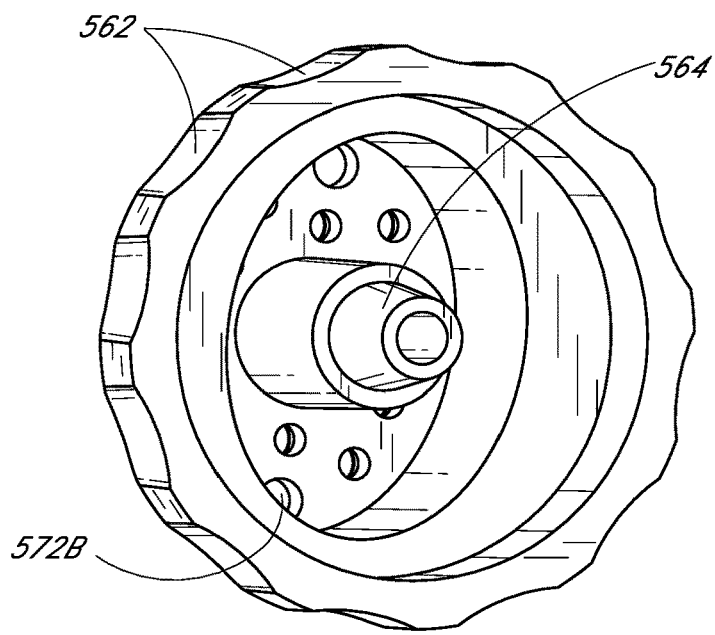
FIG. 8B illustrates a bottom perspective view of the removable tip of FIG. 8A.
Figure 8C:
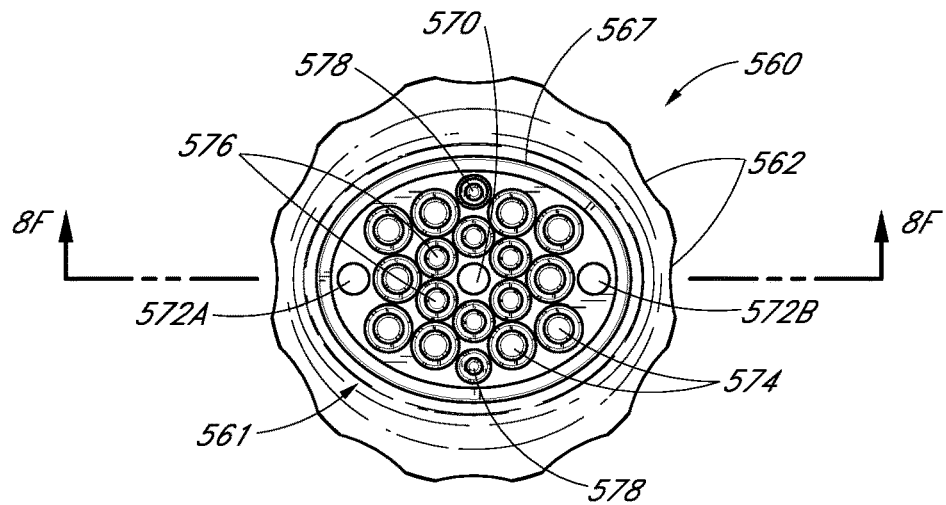
FIG. 8C illustrates a top view of the removable tip of FIG. 8A.
Figure 8D:
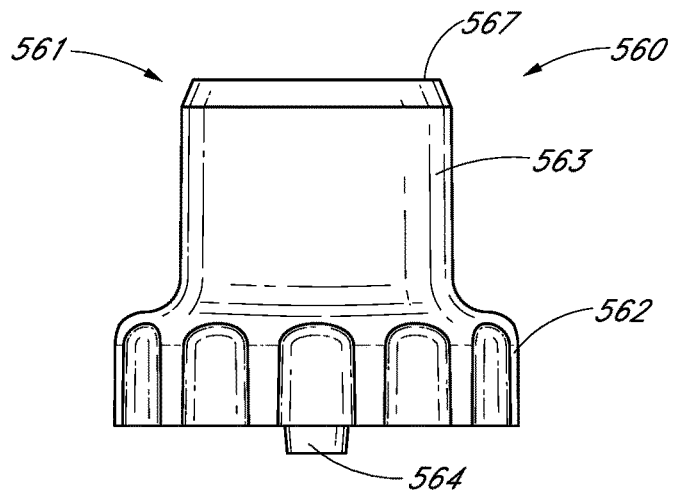
FIG. 8D illustrates a side view of the removable tip of FIG. 8A.
Figure 8E:
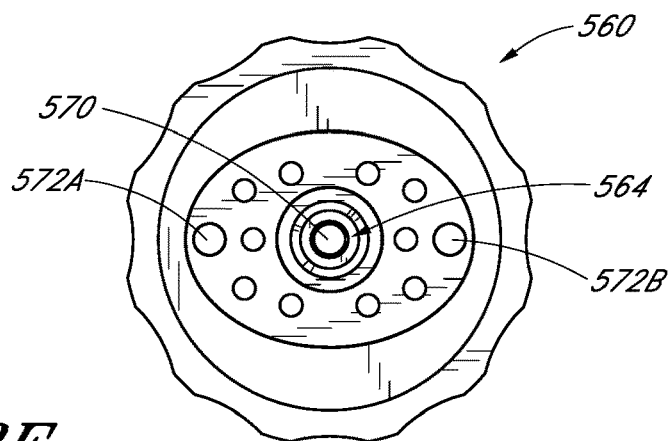
FIG. 8E illustrates a bottom view of the removable tip of FIG. 8A.
Figure 8F:
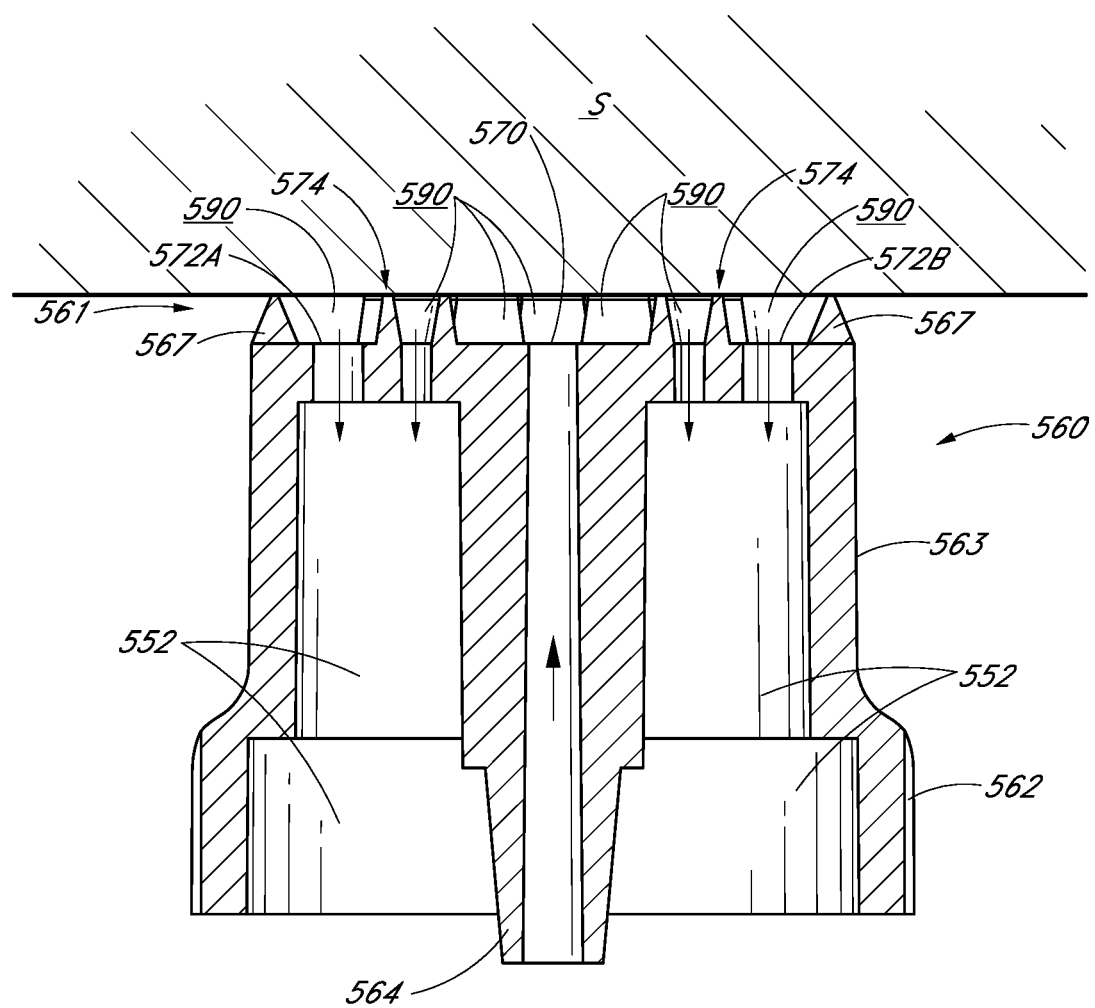
FIG. 8F illustrates a cross-sectional view of the removable tip of FIG. 8A.

As illustrated in FIGS. 8A, 8C and 8D, the tip can include a lip 567 or other ridge member along or near its outer periphery. The lip member 567 can generally define the periphery of the distal end 561 of the tip 560. In some embodiments, when the tip 560 is positioned against the skin S, as depicted in FIG. 8F, the lip member 567 completely, substantially or partially inhibits fluids or other materials from escaping a space 590 (or a plurality of spaces 590) generally defined between the tip 560 and the adjacent skin surface S.

With continued reference to FIGS. 8A-8F, the tip 560 can include a plurality of protruding members 574, 576, 578 positioned along its distal end 561 and within the interior of the lip member 567. The protruding members 574, 576, 578 can be posts or other cylindrically-shaped objects. In some embodiments, the protruding members 574, 576, 578 comprise relatively sharp edges, which can be configured to remove skin. The protruding members 574, 576, 578 can have relatively sharp planing blades. The plurality of protruding members 574, 576, 578 can ablate or roughen areas of the skin being treated.

As illustrated in FIGS. 8A-8F, the outer diameter or other comparable dimension (e.g., length, width, etc.) of the posts 574, 576, 578 or other protruding members can vary. For example, in the depicted embodiment, the tip 560 includes a number of large-sized posts 574, a number of medium-sized posts 576 and a number of small-sized posts 578. In other arrangements, the diameter and/or other dimensions of the protruding members can be similar or substantiality similar. The posts or other protruding members 574, 576, 578 can be located, spaced and otherwise oriented along the distal end 561 of the tip 560 in any desired or required manner.

Moreover, the location, spacing, orientation, layout and/or other characteristics of the posts 574, 576, 578 or other protruding members can be different than illustrated or discussed herein, as desired or required by a particular procedure or application. As discussed, the lip member 567 of the tip 560 can help create an enclosed space 590 (or a plurality of spaces 590) generally defined between the distal end 561 of the tip 560 and the skin surface being treated. Therefore, according to some embodiments, the lip member 567 extends above the top of the protruding members 574, 576, 578 so that the protruding members are within the enclosed space during a treatment procedure. In other embodiments, however, the top surface of the lip 567 is below or generally aligned with the top surface of the protruding members 574, 576, 578.

With continued reference to FIGS. 8A-8E, the tip 560 can include an interior delivery stem 564 that is configured to place the distal end 561 of the tip 560 in fluid communication with the one or more delivery channels or other conduits located within the handpiece assembly. For example, as discussed herein with reference to FIGS. 4, 5A and 5B, the delivery stem 164, 564 of the tip 160, 560 can be sized, shaped and otherwise adapted to receive serums, fluids and/or other materials from a delivery channel 140 of the adjustable distal portion 130 when the tip 160, 560 is properly secured within or to the handpiece assembly 100.

As illustrated in FIGS. 8A and 8C, the distal end 561 of the tip 560 can include an opening 570 through which fluids and/or other materials conveyed by the delivery stem 564 may exit. As shown, the opening 570 is located at or near the center of the distal end 561 of the tip 560. In other arrangements, a tip 560 can include additional stems 564 and/or openings 570. In addition, the size, shape, location and/or other details of the openings 570 can be different than illustrated herein.

Moreover, the distal end 561 of the tip 560 can include one or more outlet openings 572A, 572B through which exfoliated skin, spent serums, other waste liquids, fluids and other materials and/or the like can be removed. In the embodiment illustrated in FIGS. 8A-8F, the tip 560 includes two outlet openings 572A, 572B. However, more or fewer openings can be included, as desired or required. In addition, as shown in the cross-sectional view of FIG. 8F, some or all of the posts or other protruding members 574, 576, 578 can be generally hollow so that they perform a similar function as other outlet openings 572A, 572B of the tip 560. In other embodiments, however, some or all of the protruding members are not hollow or do not include openings therethrough. Regardless of the quantity, shape, size, orientation, spacing, layout and/or other characteristics of the outlet openings 572A, 572B and/or the hollow protruding members 574, 576, 576 included along the distal end 561 of the tip 560, exfoliated skin, spent serums, other fluids and/or any other materials can be removed from the enclosed space 590 to one or more collection areas 552 positioned within an interior portion of the tip 560.

In some embodiments, the outlet openings 572A, 572B and/or the protruding members 574, 576, 578 are in fluid communication with outlet stems (not shown) that extend toward one or more collection areas 552 within an interior portion of the tip 560. Once within an interior cavity or other portion of the tip 560, such waste materials can be drawn into one or more removal or waste channels 120, 150 positioned within the handpiece assembly 100 (FIG. 3B). An adequate vacuum or other suction source can transport such waste fluids and/or materials to a canister, other container and/or any other desired location via tubing 190 or another fluid conduit.

As discussed herein with reference to the schematic of FIG. 4C, in some embodiments, when the distal end 561 of a tip 560 is positioned against the skin being treated, one or more enclosed spaces are created between the skin surface and tip, generally along the interior of a peripheral lip member or other ridge. Therefore, as a vacuum or another suction force is applied to the removal or waste channels of a handpiece assembly, exfoliated skin, spent serum, other fluids and/or other materials can be removed from the enclosed spaces. In FIG. 8F, the enclosed space 590 is at least partially defined between the lip 567 of the tip 560 and the adjacent skin surface S being treated. At the same time, the delivery stem 564 of the tip 560, the delivery channel 140 of the handpiece assembly 100 (FIG. 4) and any other conduit or space that is in fluid communication with the enclosed space 590 of the tip 560 can also be subjected to a vacuum or other suction force. Consequently, serums, other treatment materials and/or the like can be advantageously transported to the distal end 561 of the tip 560 through one or more openings 570. As discussed, tip designs discussed or illustrated herein, or variations thereof, can comprise any combination of treatment elements and/or abrasive elements, as desired or required by a particular application.

For any of the tip embodiments disclosed herein, including those discussed with reference to FIGS. 1-21B, or variations thereof, the tips can comprise one or more rigid, semi-rigid and/or flexible materials, including without limitation, plastic or other polymers, metal (e.g., stainless steel), alloys, rubber, other synthetic or natural materials, combination thereof and/or the like.

Another embodiment of a removable tip 660 is illustrated in FIGS. 9A-9F. As shown, the tip 660 can include a generally oval or oblong shape. However, the tip 660 can have a different overall shape, such as, for example, circular, rectangular, other polygonal and/or the like, as desired or required. In some arrangements, the tip 660 comprises a lip 667, ridge or other feature along its outer periphery. As discussed herein with respect to the tip illustrated in FIGS. 8A-8F, such a lip 667 can help create one or more spaces along the distal end 661 of the tip generally defined by the tip 660 and the skin surface being treated.

Figure 9A:
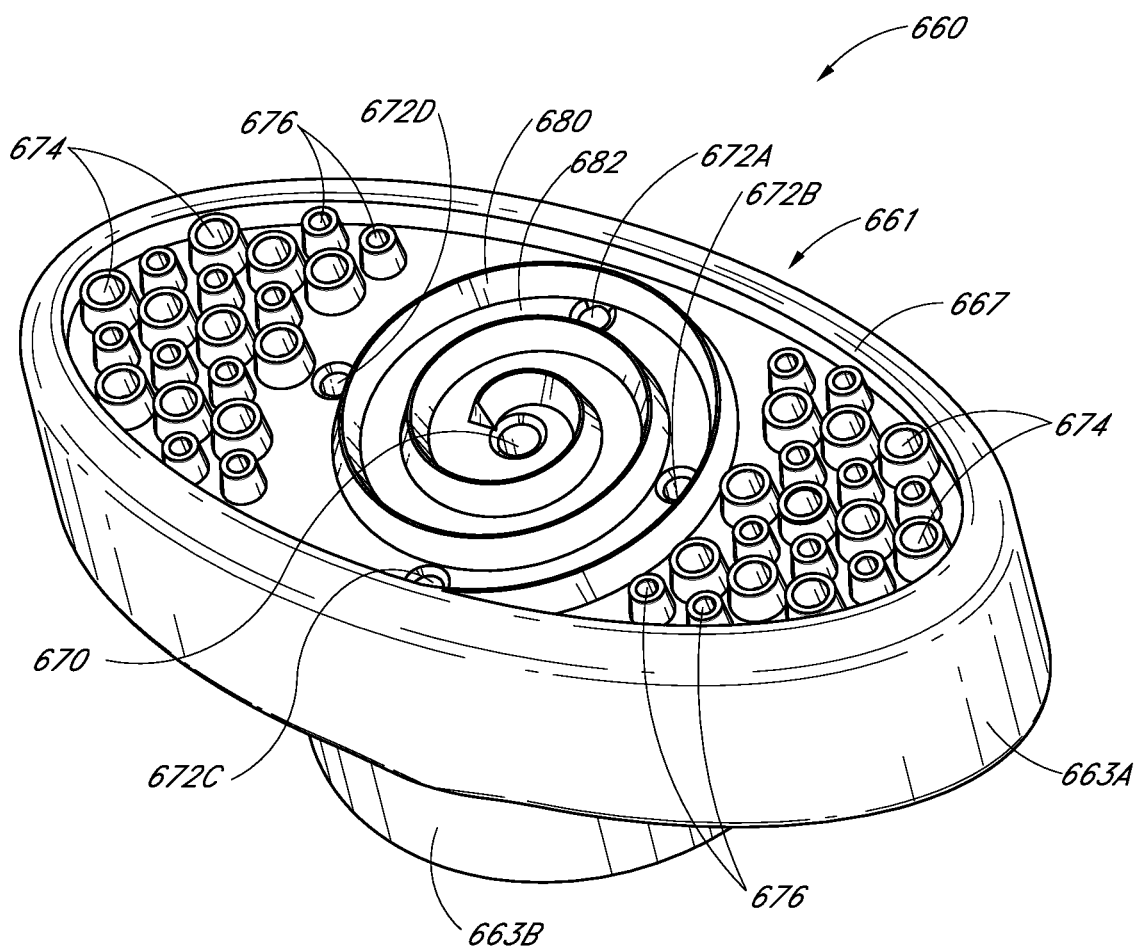
FIG. 9A illustrates a top perspective view of another embodiment of a removable tip configured to be placed along the distal end of a handpiece device.
Figure 9B:
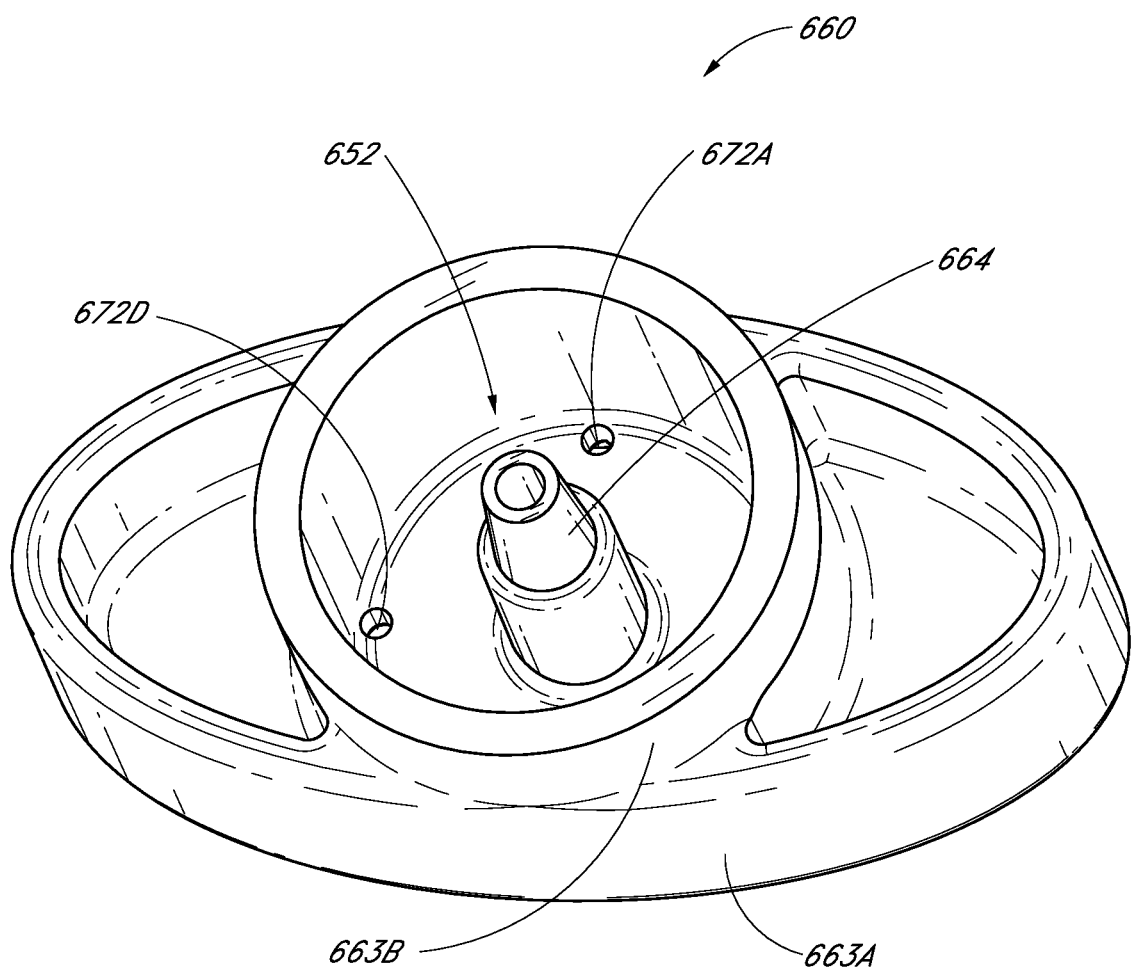
FIG. 9B illustrates a bottom perspective view of the removable tip of FIG. 9A.
Figure 9C:
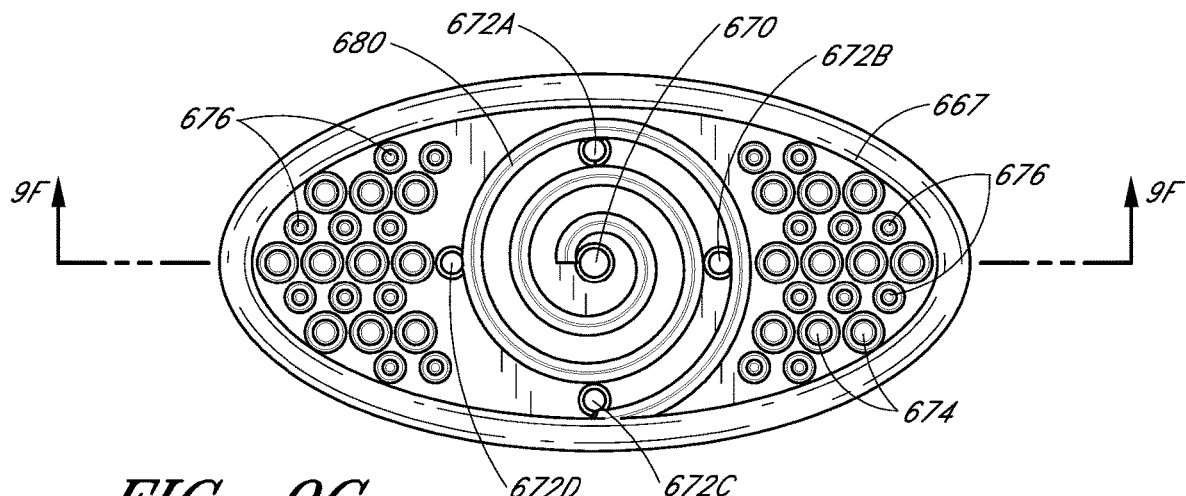
FIG. 9C illustrates a top view of the removable tip of FIG. 9A.
Figure 9D:
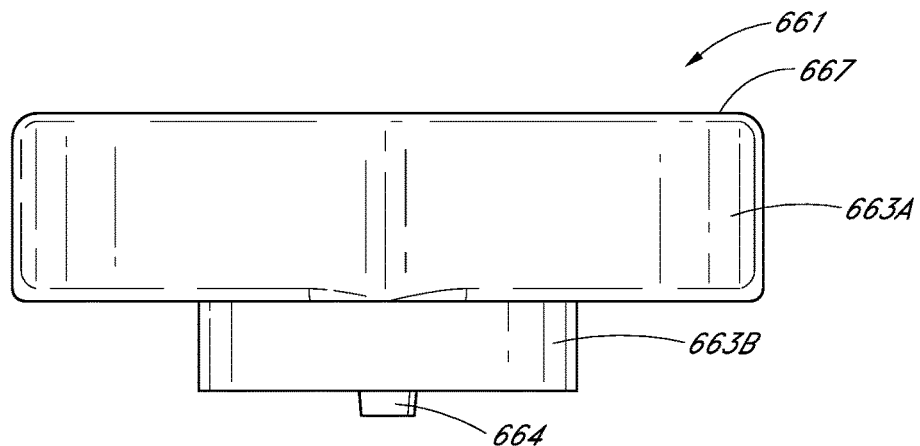
FIG. 9D illustrates a side view of the removable tip of FIG. 9A.
Figure 9E:
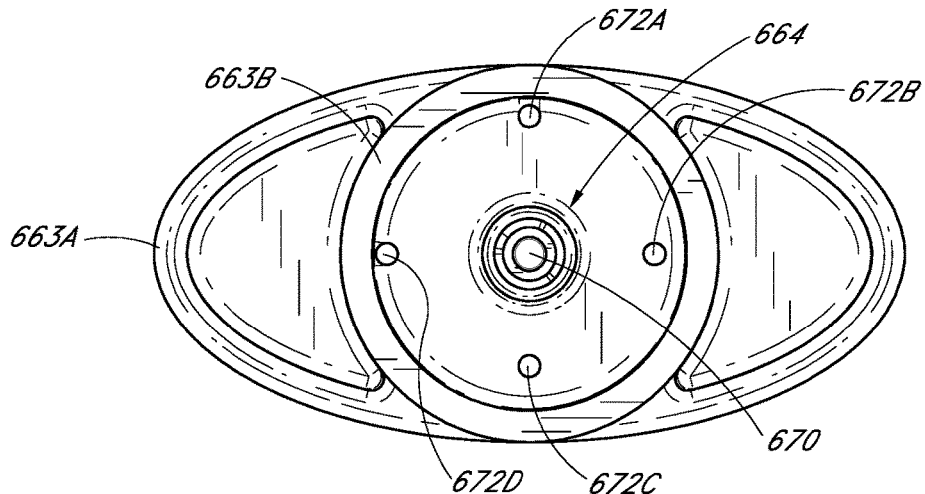
FIG. 9E illustrates a bottom view of the removable tip of FIG. 9A.
Figure 9F:
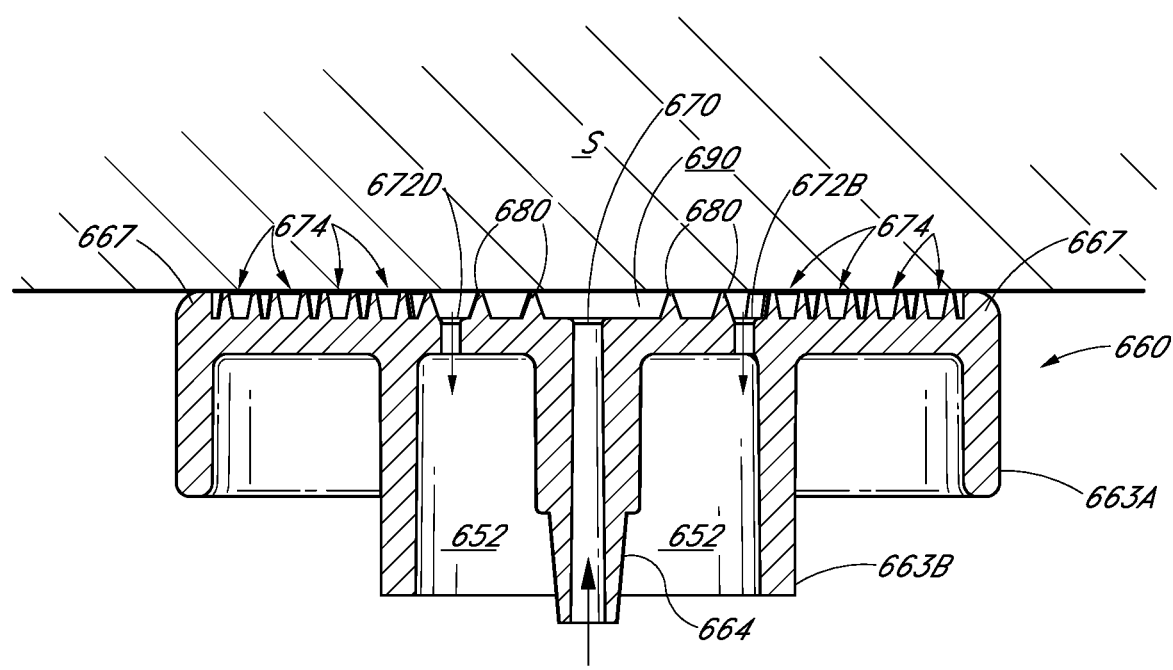
FIG. 9F illustrates a cross-sectional view of the removable tip of FIG. 9A.

With further reference to FIGS. 9A, 9C and 9F, the distal end 661 of the tip 660 can include a spiral-shaped channel 682 generally formed by a ridge 680 or other member. In the illustrated embodiment, the channel 682 extends generally continuously from a central opening 670 through which serums, other fluids and/or other materials conveyed to the tip 660 may exit. As shown, the tip 660 can include one or more outlet openings 672A-672D to permit exfoliated skin, spent serums and other fluids and/or any other waste materials to be removed from the distal end 661 of the tip 660. The outlet openings 672A-672D can be located within or near the channel 682 and/or anywhere else along the distal end 661.

With continued reference to FIGS. 9A and 9C, the tip 660 can include a plurality of protruding members 674, 676 that extend along its distal end 661. As discussed with reference to FIGS. 8A-8F, such protruding members 674, 676 can include relatively sharp edges that are configured to remove skin. In the illustrated arrangement, the protruding members 674, 676 include a generally cylindrical shape and are disposed along the outer portions of the tip 660. In addition, some of the protruding members 676 can have a different diameter (or other comparable dimension), length or other dimension than other protruding members 674. However, the quantity, diameter or other dimensions, size, shape, spacing, location, orientation, density, layout and/or other properties of the protruding members 674, 676 can vary as desired or required by a particular application or use.

In the depicted arrangement, since they are not in fluid communication with a vacuum or other suction force, some or all of the protruding members 674, 676 are not hollow and/or do not include openings therethrough. In other embodiments, however, one, some or all of the protruding members 674, 676 are configured to be in fluid communication with a collection area 652 of the tip 660. As illustrated in FIGS. 9B, 9D and 9F, the tip 660 can include an upper body portion 663A and a lower body portion 663B. In some embodiments, the delivery stem 564 through which serum, water, other liquids and/or other treatment materials are delivered to the distal end 661 and one or more collection areas 652 to which waste materials are directed can be housed within the lower body portion 663B. As discussed, the tip 660 depicted in FIGS. 9A-9F and discussed herein, or variations thereof, can comprise any combination of treatment elements and/or abrasive elements, as desired or required by a particular application.

FIGS. 10A-10F illustrate another embodiment of a removable tip 760 configured to be secured to a handpiece assembly. As with other arrangements disclosed herein, the tip 760 preferably includes one or more features that are adapted to remove skin during a treatment procedure. For example, in the illustrated embodiment, the tip 760 includes one or more pads 780A-780D or other members having a generally abrasive surface. The abrasive surface can include grit, a plurality of members (e.g., members similar to the protrusion members or posts described and illustrated herein) and/or the like. In some embodiments, the pads 780A-780D and/or other abrasive members are selectively removable from the tip 760. This permits users to advantageously change the abrasive portion of a tip 760 without replacing the entire tip 760. A pad 780A-780D or other abrasive member can be secured to the tip 760 using adhesives, snap connections, press-fit connections, hinged connections, tabs, screws, rivets, other fasteners and/or any other method or device. For example, if a pad is attached to a tip using an adhesive layer or substance, the pad can be removed by physically scraping or otherwise separating the pad and adhesives from the adjacent surfaces of the tip. Accordingly, a new pad or other abrasive member can then be glued or otherwise attached to the tip. In other embodiments, as illustrated in FIGS. 19A-20D and discussed in greater detail herein, the tip can be configured to receive a removable pad comprising one or more abrasive surfaces.

Tips comprising removable pads 780A-780D or other abrasive members can help enhance the flexibility of a skin treatment device or system. For instance, such pads can allow a user to make changes to the skin treatment properties of a tip without having to replace the entire tip or changing the tip design. For example, a user can selectively change the roughness and/or abrasiveness of the tip by replacing only the pads 780A-780D along the distal end 761.

Figure 10A:
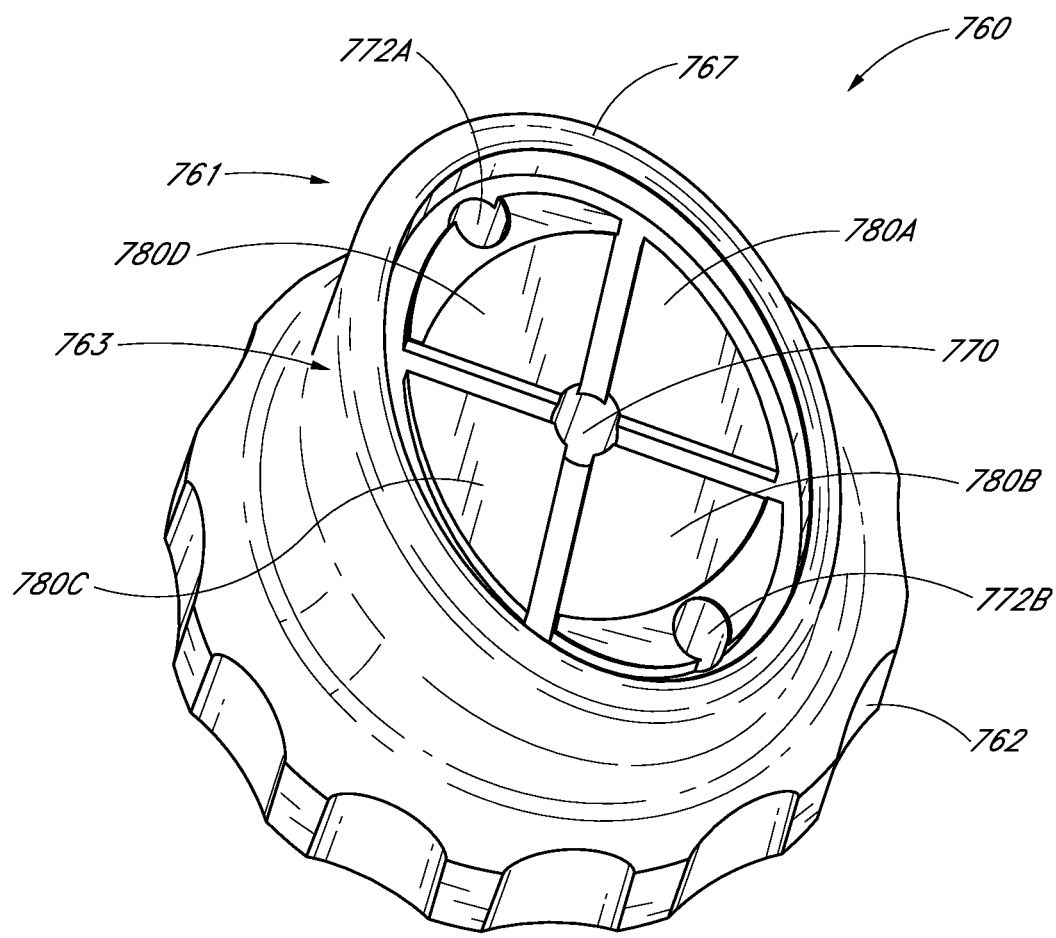
FIG. 10A illustrates a top perspective view of another embodiment of a removable tip configured to be placed along the distal end of a handpiece device.
Figure 10B:
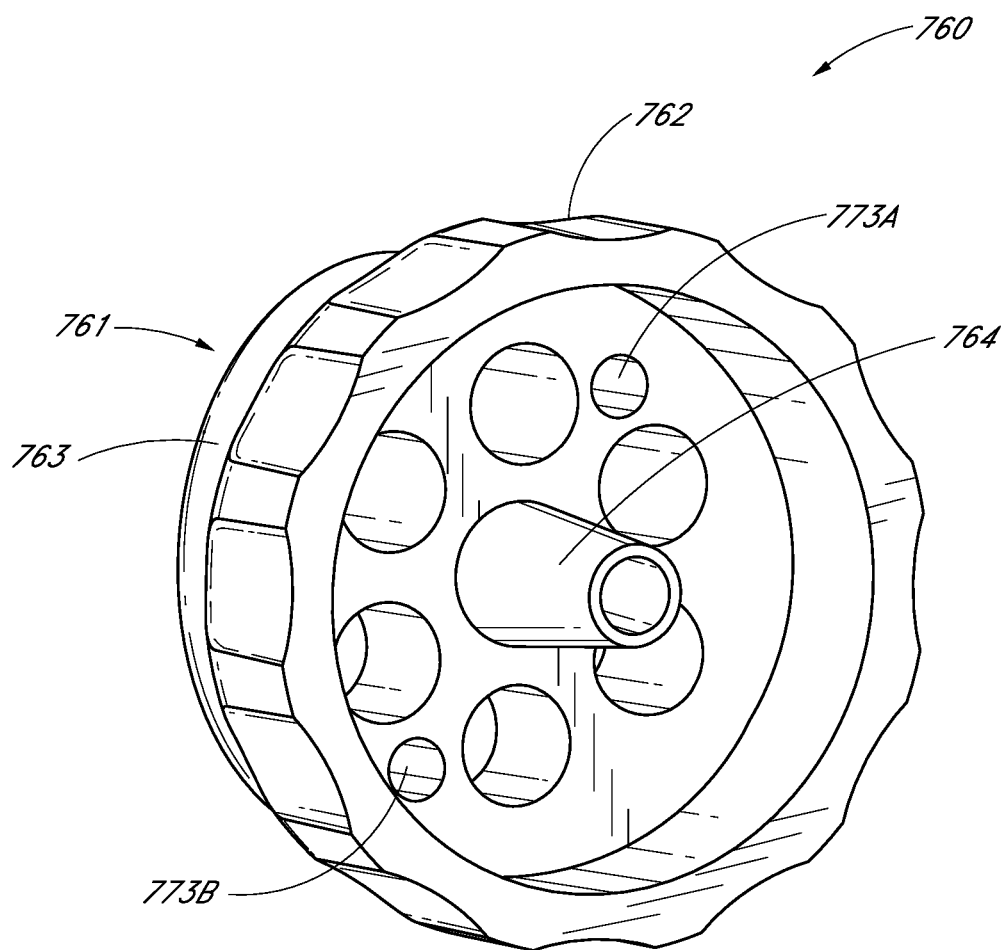
FIG. 10B illustrates a bottom perspective view of the removable tip of FIG. 10A.
Figure 10C:
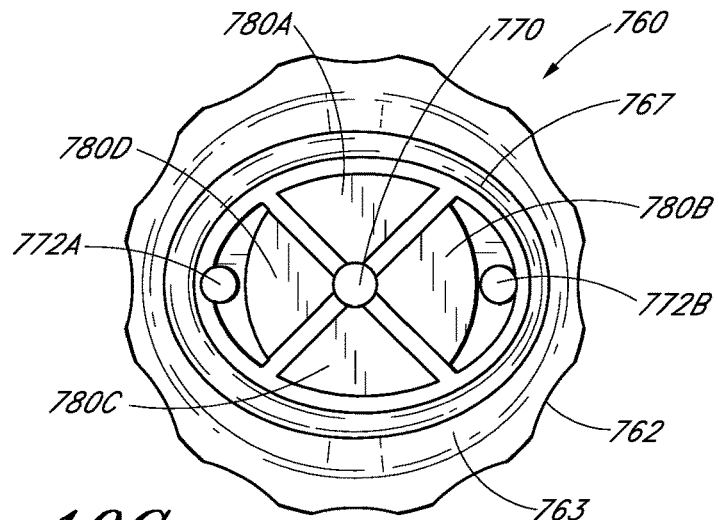
FIG. 10C illustrates a top view of the removable tip of FIG. 10A.
Figure 10D:
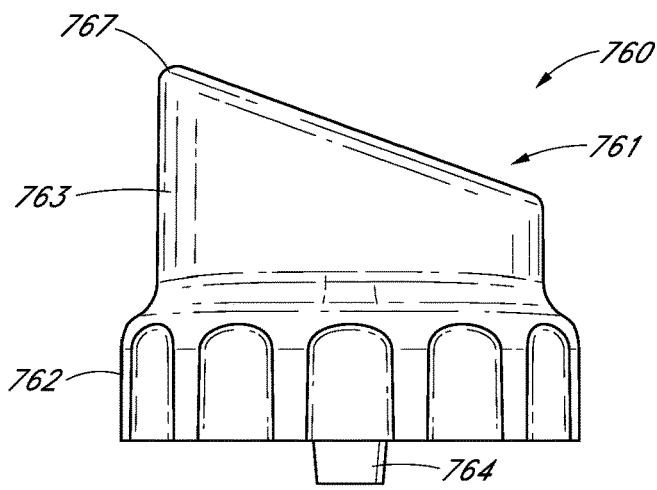
FIG. 10D illustrates a side view of the removable tip of FIG. 10A.
Figure 10E:
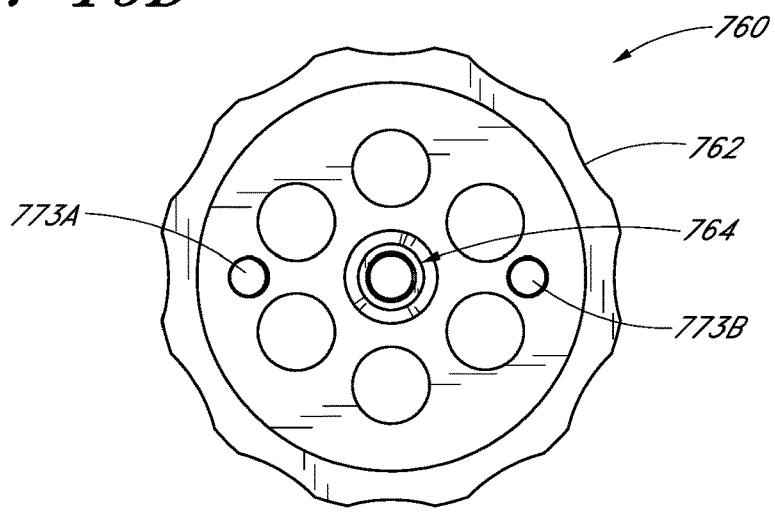
FIG. 10E illustrates a bottom view of the removable tip of FIG. 10A.

With continued reference to FIGS. 10A and 10C, the tip 760 can comprise a plurality of separate pads 780A-780D or other abrasive members. Alternatively, the tip 760 can include more or fewer (e.g., one, two, three, four, five, more than five, etc.) pads 780A-780D, as desired or required by a particular application or use. The pads 780A-780D or other members can be sized, shaped, oriented and/or otherwise configured to cover all, most or some of the distal end 761 of the tip 760.

As with other tip arrangements discussed and/or illustrated herein, the tip 760 depicted in FIGS. 10A-10F comprises an opening 770 along its distal end 761 that is in fluid communication with a delivery stem 764 or other conduit. Thus, serums, water, other fluids and/or any other materials can be delivered to the distal end 761 of the tip 760 through one or more such openings 770. In addition, the tip 760 can include one or more outlet openings 772A, 772B through which exfoliated skin, spent serums, other fluids and/or any other waste materials can be removed from the distal end 761. As illustrated in the cross-sectional view of FIG. 10F, such waste materials can be conveyed to one or more collection areas 752 within an interior portion of the tip 760 through corresponding waste channels 773A, 773B or other conduits. Alternatively, waste fluids and other materials can be directed to a collection area 752 without a dedicated waste channel of conduit 773A, 773B (see FIGS. 8A-8F and 9A-9F).

Figure 10F:
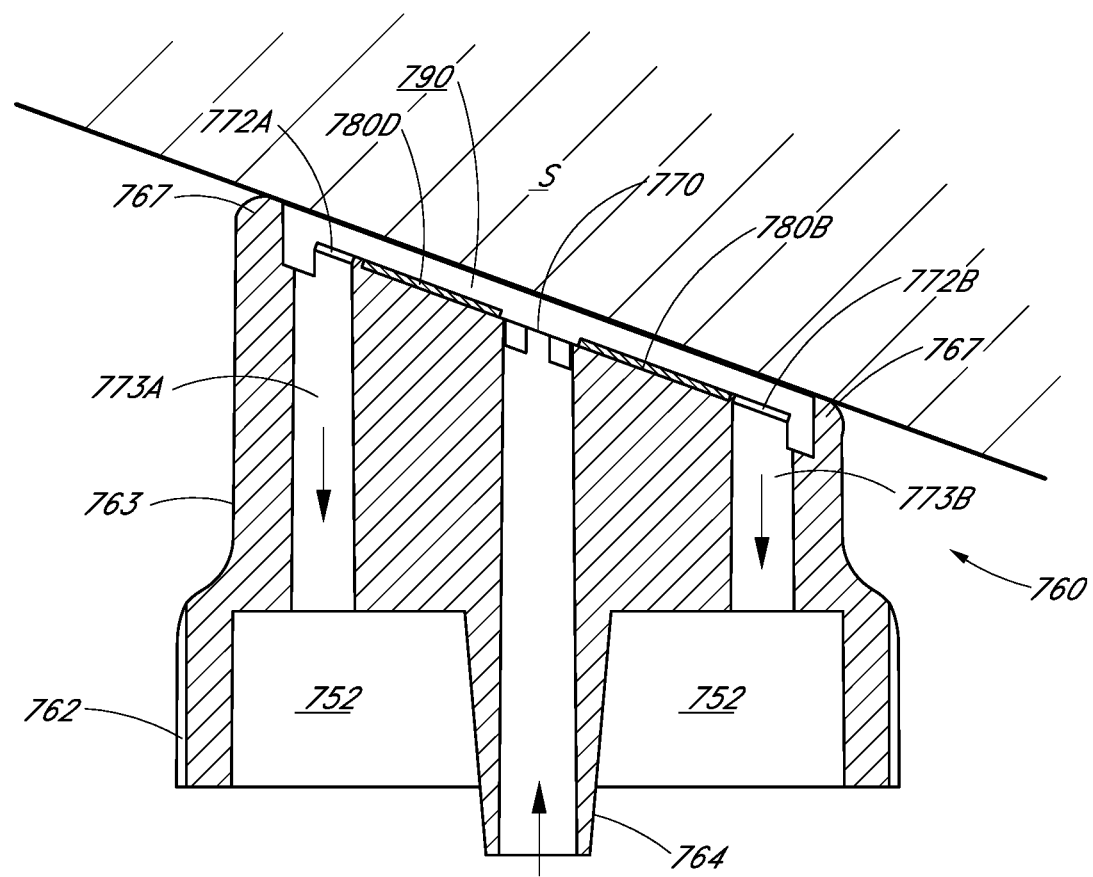
FIG. 10F illustrates a cross-sectional view of the removable tip of FIG. 10A.

With continued reference to FIG. 10F, the tip 760 can include an outer lip 767 or other peripheral member that is configured to create an enclosed space 790 when the tip 760 is generally positioned against skin. As discussed, the application of an adequate vacuum or other suction force to such an enclosed space 790 can help remove spent fluids, exfoliated skin and other waste materials from the distal end 761 of the tip, while simultaneously drawing serums and/or other treatment fluids or materials toward the tip (e.g., from a cartridge via a delivery stem 764).

As discussed, any of the tip embodiments disclosed herein, including but not limited to those illustrated in FIGS. 1-21B, can be configured so that the flow direction of serums, other fluids and/or other materials passing through the various conduits, channels, passages or other hydraulic components of such tips can be selectively reversed, as desired or required. For example, a tip, along with the handpiece assembly to which it is attached, can be configured so that fluids and/or other materials pass through one or more centrally-located passages, conduits or other portions thereof. Alternatively, the tip and handpiece assembly can be configured so that fluids and/or other materials pass through one or more non-centrally located (e.g., peripheral, offset, etc.) passages, conduits or other portions thereof.

Further, the connection and/or other hydraulic details of the tip and adjacent portions of the handpiece assembly can vary, as desired or required. For example, as discussed with reference to the embodiment of FIGS. 5A-5C, the adjustable distal portion of the handpiece assembly can include a nozzle or other protruding member that is configured to be secured within a recess or other corresponding portion of the tip to mechanically connect and place the two members in fluid communication with one another. However, in other arrangements, such as, for example, those illustrated in FIGS. 3A-4B, a nozzle or other protruding portion of the tip is adapted to be secured within a corresponding area of the adjustable distal portion of the handpiece assembly. Thus, the size, shape, general design, other connection and/or hydraulic details and/or other characteristics of any of the embodiments of a tip, handpiece assembly and/or other components of a skin treatment system disclosed herein, or variations thereof, can be modified, as desired or required.

Although only certain embodiments of tips are illustrated and discussed herein, any other tip configurations or designs can be used on a handpiece assembly to perform a skin treatment procedure. As discussed, in some embodiments, the tips are removable, allowing a user to selectively interchange tips either during a procedure or between procedures, as desired or required by a particular application. In other arrangements, tips are more permanently or semi-permanently attached to the handpiece assembly. Additional embodiments of tips are disclosed in U.S. patent application Ser. No. 11/392,348, filed on Mar. 29, 2006 and published on Jul. 5, 2007 as U.S. Publication No. 2007/0156124, and U.S. patent application Ser. No. 09/699,220, filed on Oct. 27, 2000 and issued on Oct. 7, 2003 as U.S. Pat. No. 6,629,983, the entireties of both of which are hereby incorporated by reference herein.

In any of the embodiments disclosed herein, or variations thereof, the tip, the handpiece assembly and/or any other component or device can include rigid and/or semi-rigid materials. For example, a tip can comprise plastic, another polymeric material, rubber, metal and/or the like. Accordingly, the tips and/or other portions of the handpiece assembly can be manufactured using any suitable method, such as, for example, injection or compression molding, thermoforming, other molding methods, casting and/or the like. The tips can be disposable so that they are used once or only for a limited number of times. Alternatively, if properly treated, the tips can be reused. Therefore, in such embodiments, the tips are preferably configured to withstand the required cleaning, sterilizing, disinfecting and/or other treatment procedures to which they may be exposed.

Any of the tips disclosed herein can be used in wet and/or dry systems. In general, wet systems include skin treatment devices, assemblies or systems in which serums, water, other fluids and/or other materials are conveyed, either continuously or intermittently, to the tip during a procedure. As discussed in greater detail herein, such fluids and/or other materials can be delivered through the handpiece assembly, tip and/or other components of the skin treatment system in their final, usable form. In other arrangements, such materials and/or substances are positioned on the tip and/or other portions the system (e.g., as solids, gels, concentrated solutions, etc.) and are adapted to be dissolved, diluted, mixed or otherwise combined with water (e.g., distilled, tap water, sterile, filtered, etc.), saline, other dilutants or dissolvents and/or other fluids to prepare them for use. On the other hand, dry systems can include skin treatment devices, assemblies and systems in which fluids and/or other materials are generally not conveyed to the tip during the procedure.

As discussed, one or more fluids and/or other substances can be delivered to the tip of a handpiece assembly during a skin treatment procedure. In some embodiments, such fluids and/or other materials are stored within a cartridge (e.g., vial, ampoule, other container, etc.) that is secured to or within the handpiece assembly. Alternatively, these fluids and/or other materials can be stored in a canister or other container that is separate from the handpiece assembly. In such arrangements, as discussed herein with reference to FIGS. 6B and 7, the handpiece assembly can be placed in fluid communication with one or more containers using conduits or other fluid lines.

In some embodiments, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance are selectively delivered to the skin during a treatment procedure. Such materials can be delivered individually or as part of a mixture. Such materials or combination of materials can be provided in a cartridge or other container, which, as discussed, can be placed in fluid communication with a handpiece assembly. These treatment fluids and other materials, either alone or in combination, can help reduce the appearance of wrinkles, fine lines, age spots, scarring and/or other skin conditions. In addition, such fluids and/or other materials can help to reduce skin roughness, thereby facilitating rejuvenation of the skin and/or improving skin texture. Further, such fluids or other treatment materials can provide one or more other therapeutic, comfort, anesthetic, aesthetic or other benefits to a user or his or her skin.

In any of the embodiments described and/or illustrated herein, or variations thereof, treatment fluids and/or other materials can be delivered to the tip of a handpiece assembly using one or more devices or methods. For example, in some embodiments, such substances are selectively delivered through a cartridge, supply canister, fluid bottle, combinations thereof and/or the like. Such serums, compositions, other fluids and/or other materials or substances can be pre-mixed so that they are delivered to the tip and the skin unmodified or substantially unmodified.

As discussed in greater detail herein, in some embodiments, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance are provided to users as a pack or in other forms. For example, such materials and other substances can be provided as a solid (e.g., tablet, capsule, etc.), dry granular materials, viscous gels, concentrated fluids or other solutions and/or the like. Such packs or other solids, semi-solid, gelatinous and/or other substances can be configured to be combined or mixed with water, saline and/or some other fluid by a user to achieve a desired end product or concentration.

In other embodiments, one or more treatment materials can be impregnated, embedded, deposited or otherwise positioned within and/or on the tips and any other portion of a handpiece assembly. Thus, such materials (e.g., powders, tablets, capsules, other solids, granular materials, gels, etc.) can advantageously dissolve, melt, break down or otherwise transform when they are contacted by water, saline, other dilutants, dissolvents and/or other liquids or fluids delivered to the tip (e.g., through the handpiece assembly, by an external fluid source, etc.) In other arrangements, the treatment materials are contained within a capsule, tablet or other enclosure. Such enclosures can be configured to dissolve when placed in water or some other fluid. Therefore, a user may be required to place a capsule, the contents of a pack or some other materials into a cartridge, canister or other container and add or otherwise supply water, saline, other fluids and/or other dissolvent before use.

Figure 11:
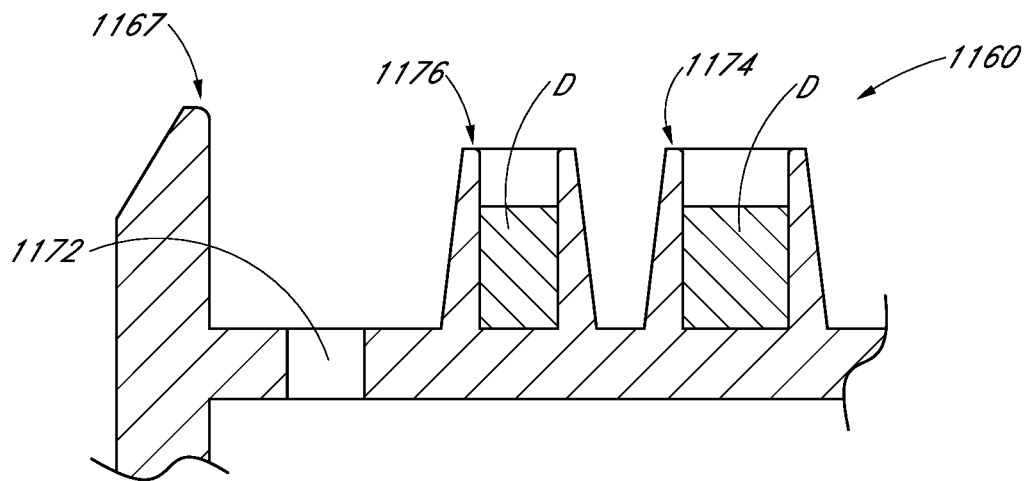
FIG. 11 illustrates a cross-sectional view of a tip comprising posts that have been partially filled with solids, gels and/or other materials configured to be mixed or combined with water, other dilutants or other fluids, according to one embodiment.

FIG. 11 illustrates a partial cross-sectional view of a tip 1160 configured to be secured to the distal end of a handpiece assembly. As shown, the tip 1160 can include one or more fluid inlet openings 1172 through which water, saline, other dilutants or dissolvents, other fluids and/or other materials can be selectively delivered to the tip, in accordance with the various embodiments disclosed herein. Further, the tip 1160 can include one or more outlet openings (not shown) through which exfoliated skin, spent serums or other fluids, debris and/or other waste materials can be removed away from the skin surface being treated.

With continued reference to FIG. 11, the tip 1160 can additionally comprise a plurality of protruding members 1174, 1176 positioned along its distal end and within the interior of the tip's outer lip member 1167. As discussed, such protruding members 1174, 1176 can be posts or other cylindrically-shaped objects. In some embodiments, the protruding members 1174, 1176 comprise relatively sharp edges that are configured to remove skin when the tip is moved relative to a skin surface. The protruding members 1174, 1176 can have relatively sharp planing blades. The plurality of protruding members 1174, 1176 can ablate or roughen areas of the skin being treated.

According to some embodiments, some or all of the posts 1174, 1776 or other protruding members comprise one or more materials or other substances D. For example, the posts can be at least partially filled with dried or granular materials, tablets, capsules, powders, gels, concentrated liquids and/or other substances that are configured to dissolve, melt, soften, dilute, disperse, mix or otherwise be removed from an interior of the protruding members 1174, 1176. Such materials or other substances, which can be provided in one or more different forms or phases (e.g., liquid, solid, gel, etc.), can include, without limitation, human growth factors, cytokines, collagen, antioxidants, matrix proteins, serums, vitamins, chemical exfoliation agents, lotions, soothing agents, brightening or lightening agents (e.g., kojic acid), peptides, peeling agents, acids, anesthetics, medicants, other non-active or active compounds, other fluids or materials, combination or mixtures thereof and/or the like.

With continued reference to FIG. 11, as water (e.g., distilled, tap water, filtered, etc.), saline, other dilutants or dissolvents, other fluids and/or the like are selectively delivered through the handpiece assembly and through one or more openings 1172 of the tip 1160, the various materials and/or other substances D situated within the posts 1174, 1176 can be dissolved, diluted and/or otherwise mixed to form a desired solution or mixture. Thus, a tip 1160 can be customized for a particular skin treatment procedure by including one or more desired or required substances within the protruding members and/or other cavities of the tip 1160. Accordingly, the various solutions conveyed, dissolved and/or otherwise generated at or near the tip 1160 can used to achieve a desired result, such as, for example, providing vitamins, growth factors, soothing agents or lotions, healing agents and/or other substances to treated skin, moisturizing the skin, enhancing the comfort of the person being treated and/or the like. Further, such materials impregnated or otherwise disposed on the tip can be customized to target a particular treatment procedure or phase, skin type, skin ailment or condition and/or the like.

Providing the desired materials and/or other substances on the tip can help simplify a microdermabrasion or other skin treatment procedure. For instance, in such embodiments, the user may only need to provide water, saline and/or some other basic fluid to perform the procedure. Thus, the need to deliver separate serums, other fluids and/or materials through the handpiece assembly (e.g., using a manifold system, a cartridge, etc.) can be advantageously eliminated or simplified. As a result, the likelihood of a user making mistakes can be reduced or eliminated. In addition, by delivering only water, saline and/or other relatively clean fluids through the various delivery conduits, passages, ports, openings and other hydraulic components of the tip, handpiece assembly and other components of a skin treatment system, the need to periodically clean the various devices and other equipment can be advantageously reduced or eliminated. Thus, the effective life of the skin treatment system can be extended. Relatedly, the likelihood of potentially dangerous or undesirable cross-contamination between the various serums, agents, other fluids and/or other materials can also be reduced or eliminated.

Figure 12A:
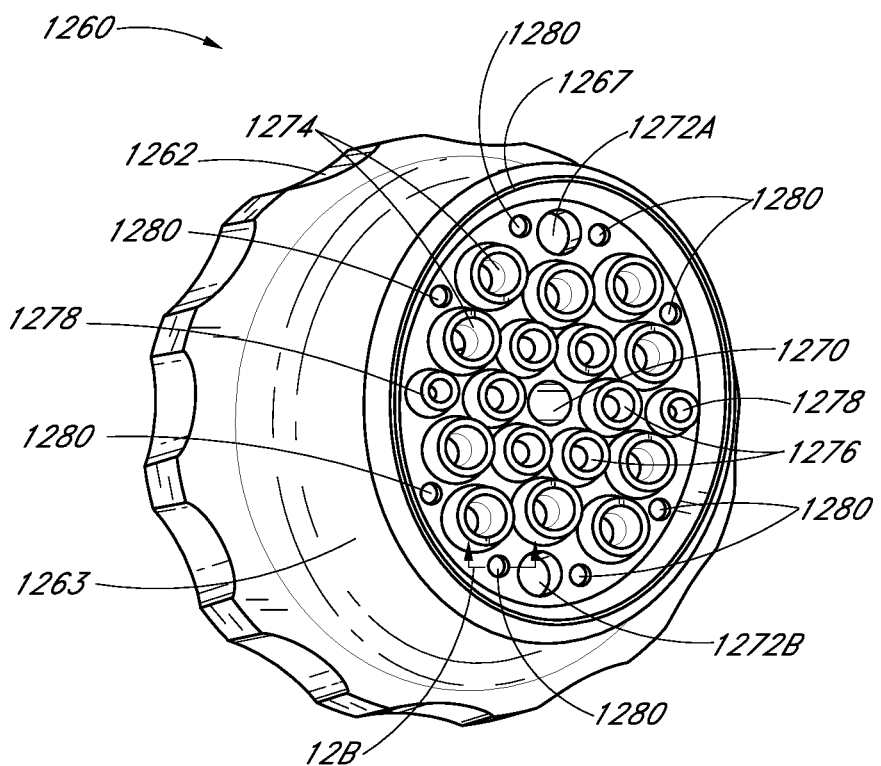
FIG. 12A illustrates a front perspective view of one embodiment of a tip comprising a plurality of recesses that can be selectively filled solids, gels and/or other materials.

FIG. 12A illustrates one embodiment of a tip 1260 comprising a plurality of recesses 1280 or other openings located along its distal surface. As shown, such recesses 1280 or other openings can be positioned along an outer periphery of the tip's distal surface. However, in alternative embodiments, one or more recesses 1280 are located between the posts 1274, 1276, 1278 and/or at any other location, either in lieu of or in addition to the recesses 1280 being positioned along an outer periphery of the tip. Such recesses or other openings can be configured to include one or more solids, gels, concentrated solution, dissolvable materials and/or other substances D therein.

Figure 12B:
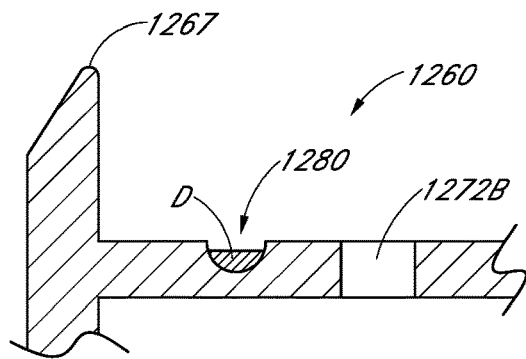
FIG. 12B illustrates a cross-sectional view of the tip of FIG. 12A.
Figure 12C:
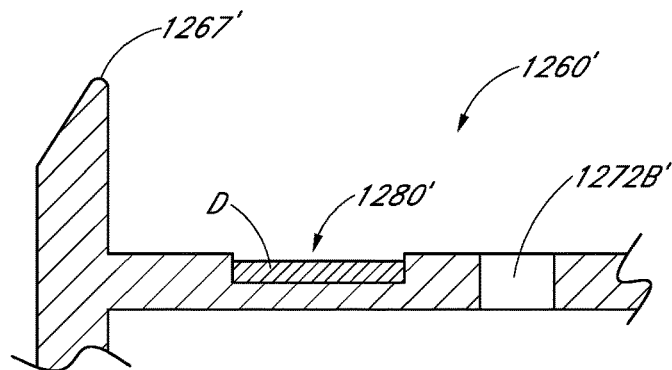
FIG. 12C illustrates a cross-sectional view of another embodiment of a tip comprising one or more recesses that are configured to selectively receive solids, gels and/or other materials.

With reference to the cross-sectional view of FIG. 12B, the recesses can include a semi-circular, curvate or other rounded shape. In certain embodiments, the recesses 1280 are at least partially filled with dried or granular materials D, tablets, capsules, powders, gels, concentrated liquids and/or other substances that are configured to at least partially dissolve, melt, soften, dilute, disperse, mix or otherwise be removed from an interior of the recesses or other openings. As discussed herein with reference to other embodiments, such materials or other substances, which can be provided in one or more different forms or phases (e.g., liquid, solid, gel, etc.), can include, without limitation, human growth factors, cytokines, collagen, antioxidants, matrix proteins, serums, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or the like.

The quantity, size, depth, shape, capacity, location, spacing and/or other details of the recesses or other openings positioned along one or more tip surfaces can vary, as desired or required. For example, in the tip arrangement of FIG. 12C, the illustrated recess 1280' includes a generally rectangular cross-sectional shape. However, a recess or other opening can include any other cross-sectional shape, such as, for example, triangular, other polygonal, irregular and/or the like.

Figure 13A:
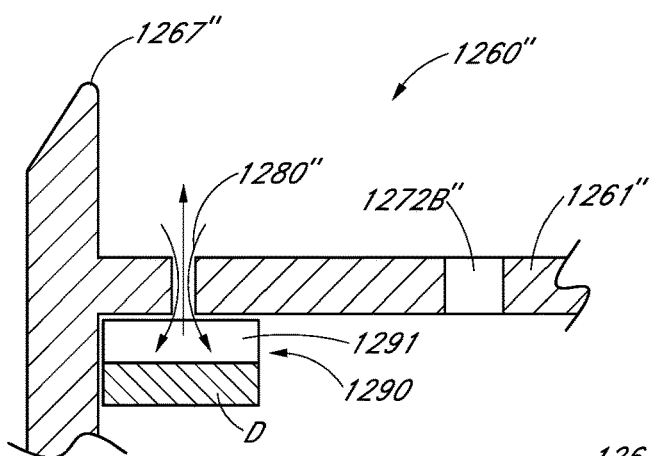
FIG. 13A illustrates a cross-sectional view of a tip having a cartridge or other container comprising solids, gels and/or other materials secured thereto, according to one embodiment.
Figure 13B:
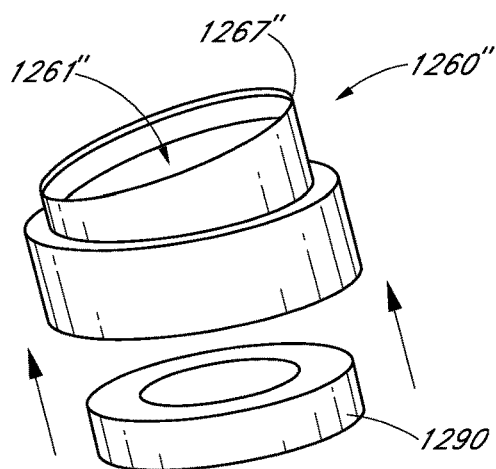
FIG. 13B illustrates an exploded perspective view of the tip and cartridge of FIG. 13A.

In alternative embodiments, the desired solids D, other dry or semi-dry materials, gels, concentrated materials and/or other substances are included within a cartridge or other container. As illustrated in FIGS. 13A and 13B, such a cartridge 1290 or other container can be secured to one or more portions of the tip 1260". In the depicted arrangement, the cartridge 1290 is situated below the top surface 1261" of the tip 1260" and aligned with one or more openings 1280" of the top surface 1261". Accordingly, the solids, gels, fluids and/or other materials or substances stored within an interior of the cartridge 1290 can be configured to exit the cartridge 1290 through one or more openings 1280" of the tip's top surface 1261". In some embodiments, the cartridge or other container 1290 includes one or more slots, perforations, orifices or other openings through which the various materials D can exit. Alternatively, the cartridge 1290 can include one or more porous surfaces that allow the internal contents D to freely exit the cartridge 1290. Thus, the cartridge 1290 can include a outer cage, a perforated or other porous surface and/or the like.

With continued reference to FIG. 13A, water (e.g., distilled, tap water, filtered, etc.), saline, other dilutants or dissolvents and/or other fluids that are delivered to the tip 1260" (e.g., through one or more openings 1272" along the top surface 1261" of the tip 1260") can be configured to enter into an interior 1291 of the cartridge 1290 through one or more openings 1280". Accordingly, the materials and/or other substances D contained within the cartridge 1290 can be at least partially dissolved, melted, diluted, reacted and/or otherwise mixed or combined with the water, saline or other fluids. This can facilitate the controlled removal of these materials D toward the distal working surface of the tip 1260".

As illustrated in FIG. 13B, the cartridge 1290 can have a generally toroidal or donut-shape. In some embodiments, the cartridge 1290 or other container is configured to be positioned within an interior portion of the tip 1260". The cartridge 1290 can be secured to the tip 1260" using a friction fit connection, one or more mechanical features or devices (e.g., threads, clips, screws, tabs, etc.) and/or any other attachment device or method. In addition, the shape, size, orientation relative to the tip 1260" and/or any other characteristics of the cartridge 1290 can be different than illustrated in FIGS. 13A and 13B. For instance, the cartridge 1290 or other container can have a generally rectangular, circular or any other shape. Further, the cartridge 1290 can be configured so that it does not extend around the entire perimeter of the tip 1260". In other embodiments, a cartridge or other container comprising solids, gels and/or other materials is positioned along a different portion of the tip, such as, for example, at or near the center, locations between the center and the periphery and/or the like.

Figure 14A:
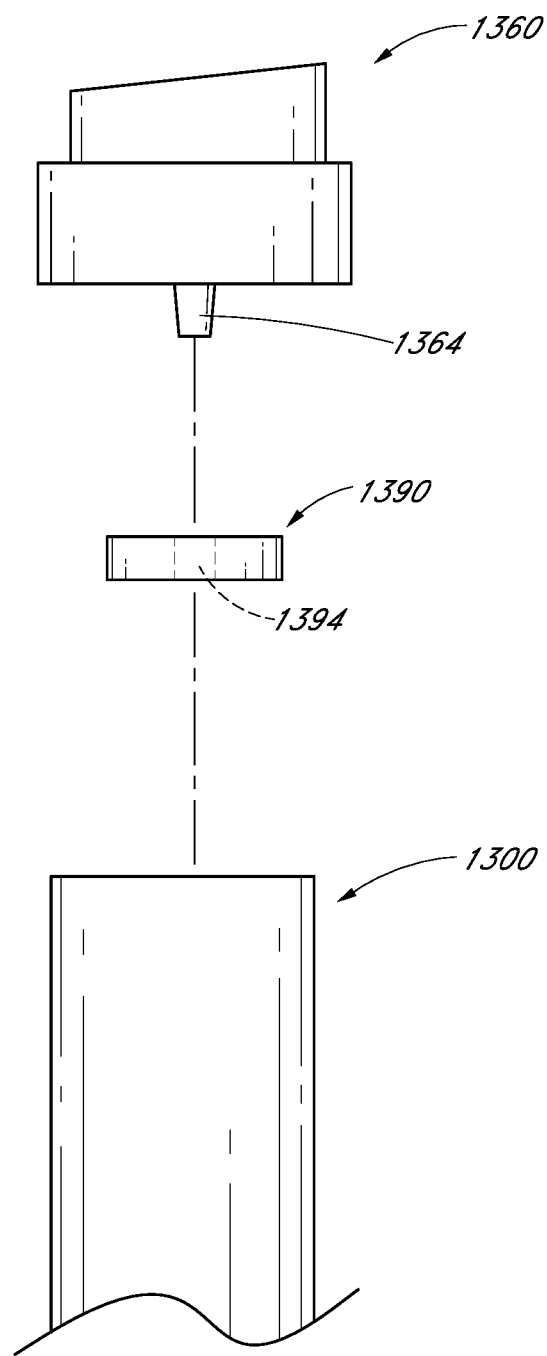
FIG. 14A schematically illustrates an exploded view of a handpiece assembly, a tip and a cartridge or other container according to one embodiment.

FIG. 14A schematically illustrates an embodiment of a disc 1390, capsule or other item comprising one or more solids, other dried or partially dried substances, gels, concentrated solutions and/or the like. These materials can comprise some, most or the entire portion of the disc 1390 or other item. Alternatively, the materials can be embedded, impregnated and/or otherwise situated on or within one or more portions or areas (e.g., surface) of the disc 1390 or other item. In other embodiments, such solids, gels and/or other materials are provided in a cartridge or other container that includes one or more openings through which the substances may exit (e.g., in their original form, after being at least partially dissolved, diluted or otherwise mixed with water or another fluid, etc.).

With continued reference to FIG. 14A, the disc 1390, capsule or other item can be sized, shaped and otherwise configured to be positioned between the tip 1360 and the main body portion 1300 of a handpiece assembly. According to some embodiments, the disc 1390 or other item includes an opening 1394 or other feature that is adapted to engage and secure to one or more regions of the tip 1360, the main body portion 1300 and/or any other area of a handpiece assembly. In certain arrangements, the disc 1390 is maintained in a desired orientation when the tip 1360 is properly connected to the main body portion 1300 of the handpiece assembly. However, a desired or required position of a disc 1390, capsule or any other items comprising one or more solids, gels, concentrated solutions or other fluids and/or other materials can be maintained using any other attachment method or device.

Figure 14B:
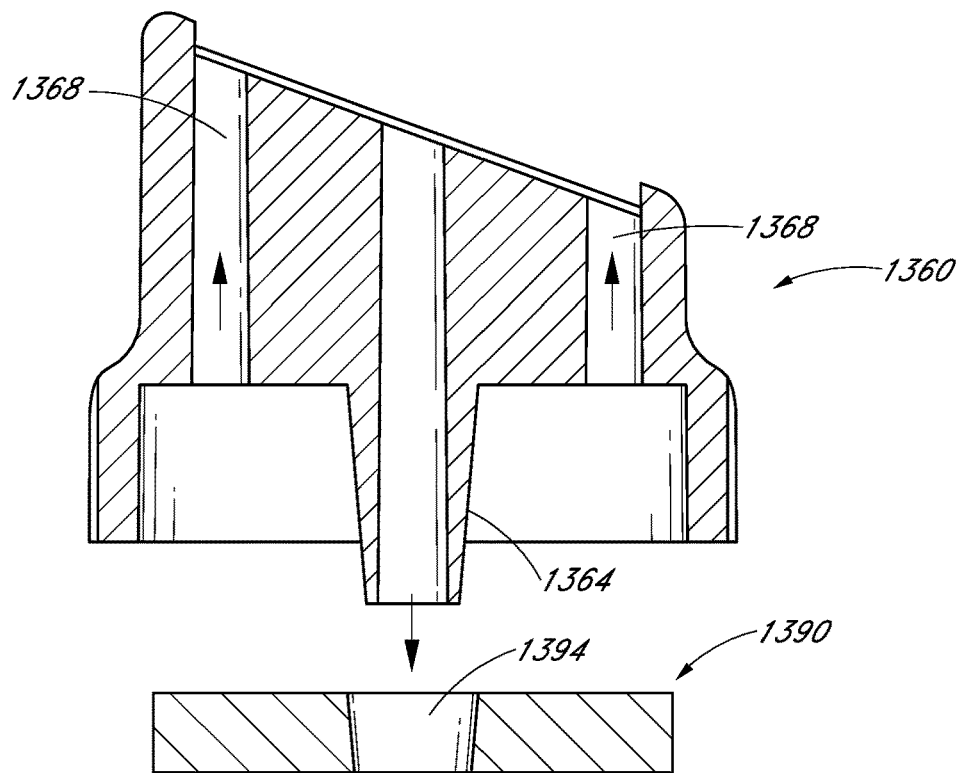
FIG. 14B illustrates an exploded cross-sectional view of one embodiment of a tip and a cartridge or other container comprising solids, gels and/or other materials.
Figure 14C:
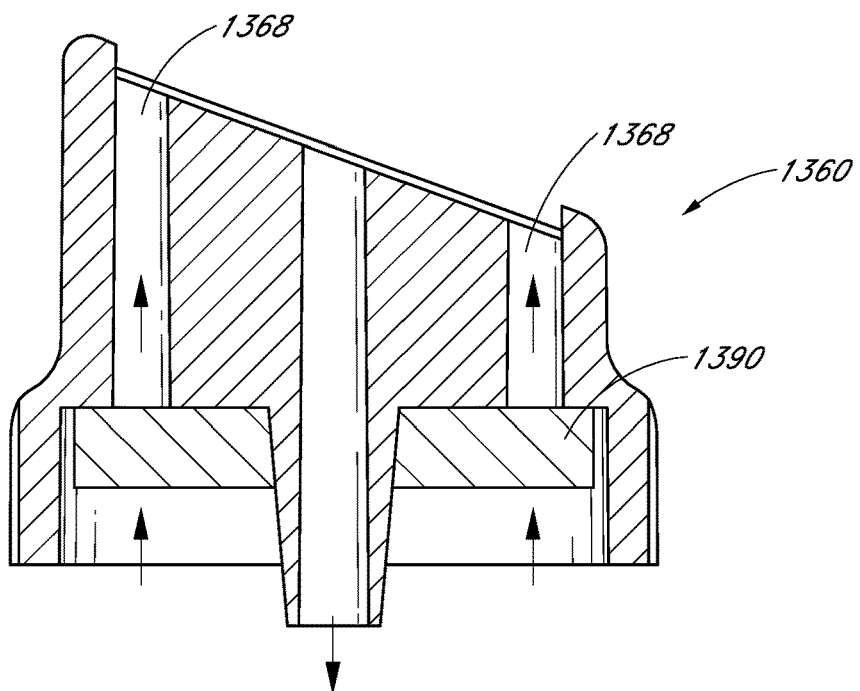
FIG. 14C illustrates a cross-sectional view of the cartridge and tip of FIG. 14B with the cartridge secured within an interior portion of the tip according to one embodiment.

FIGS. 14B and 14C illustrate one embodiment of a disc 1390, capsule or other item comprising one or more human growth factors, cytokines, soluble collagen, antioxidants, matrix proteins, serums, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or other substances. For example, as discussed, such materials can be provided on or within the disc 1390 (e.g., along an exterior surface, within an interior portion, etc.).

According to some embodiments, the disc 1390 includes a center opening 1394 to permit the disc 1390 to be positioned over a stem 1364 extending within an interior of the tip 1360. In the illustrated arrangement, the stem 1364 comprises an outlet conduit or channel that is configured to remove exfoliated skin, spent treatment materials and other debris away from the distal end of the tip 1360. However, as discussed herein with reference to the tip of FIGS. 15A and 15B, the stem 1364 can include one or more conduits or channels that are configured to deliver water, saline, other dis solvents, dis solvents, dissolving agents and/or other fluids toward the skin surface being treated.

With continued reference to FIGS. 14B and 14C, the disc 1390, capsule, cartridge or container or other item comprising the desired materials can be configured to be removably fixed to the stem 1364 of the tip 1360 using a press-fit or other friction connection. For example, in some embodiments, the disc 1390 can be positioned far enough into an interior of the tip 1360 so that the exterior surface of the tip's stem 1364 frictionally engages the inner surface of the disc's opening 1394. However, as discussed, one or more other attachment methods or devices can be used in addition to or in lieu of such a friction or press fit connection in order to secure the disc 1390 to the tip 1360.

Once the disc 1390, capsule or other member has been properly secured to the tip 1360, as depicted in FIG. 14C, the tip 1360 can be attached to the distal end of the handpiece assembly (e.g., adjustable distal portion). Thus, water (e.g., distilled, tap water, filtered, etc.), saline, other dilutants or dissolvents or other fluids being delivered to the tip 1360 can be configured to contact the various substances (e.g., tablets, capsules, other solids, granulated materials, gels, concentrated solutions or other materials, etc.) situated on or within the disc 1390. Such materials and other substances can be advantageously dissolved, diluted, melted, softened and/or otherwise conditioned so that they are delivered to the distal end of the tip 1360 through one or more conduits 1368 of the tip 1360. As a result, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance can be advantageously delivered to the skin being treated, as desired or required.

According to some embodiments, water, saline or other fluids are configured to flow past the exterior surfaces of the disc 1390, capsule or other item. Thus, solids, gels, fluids and/or other materials impregnated on such surfaces, positioned within recesses or other openings in fluid communication with such surfaces and/or the like can be transferred to the skin surface being treated. In alternative embodiments, the solids, gels, fluids and/or other materials are positioned within an interior cavity of the disc 1390 or other item. For example, the disc 1390 or capsule can comprise a cage or other porous structure that is configured to house one or more dissolvable or dilutable solids or gels. Therefore, water, saline and/or other fluids can be adapted to travel through one or more openings of the disc 1390 or other member in order to contact the various materials contained therein. Accordingly, the disc 1390 can be configured to lose mass over time as water or other fluids dissolve, dilute or otherwise combine with the materials positioned on or within the disc 1390. In alternative embodiments, the disc 1390 (e.g., cage, container having one or more openings, etc.) or other item secured within the tip 1360 is adapted to maintain its shape over time if such a disc is used to merely contain the solids, gels, fluids and/or other materials that will be selectively transported toward the distal end of the tip 1360.

Such discs 1390, capsules, containers or other items can be used in conjunction with any of the tip designs illustrated or discussed herein, or variations thereof. Further, the size, shape, general configuration, location relative to the tip or other adjacent portions of the handpiece assembly and/or any other characteristics of the disc 1390 can vary, as desired or required. For instance, the disc 1390 can include a non-circular shape (e.g., rectangular, triangular, other polygonal, elliptical, etc.). Further, the disc 1390 can include a curved or fluted surface. In other arrangements, a disc 1390 does not extend completely around a stem 1464 or other central portion of the tip interior. Thus, the disc 1390 can be asymmetrically positioned relative to the stem 1464 or tip centerline. In another embodiment, the disc 1390 is positioned on only one side of the stem 1464.

Figure 15A:
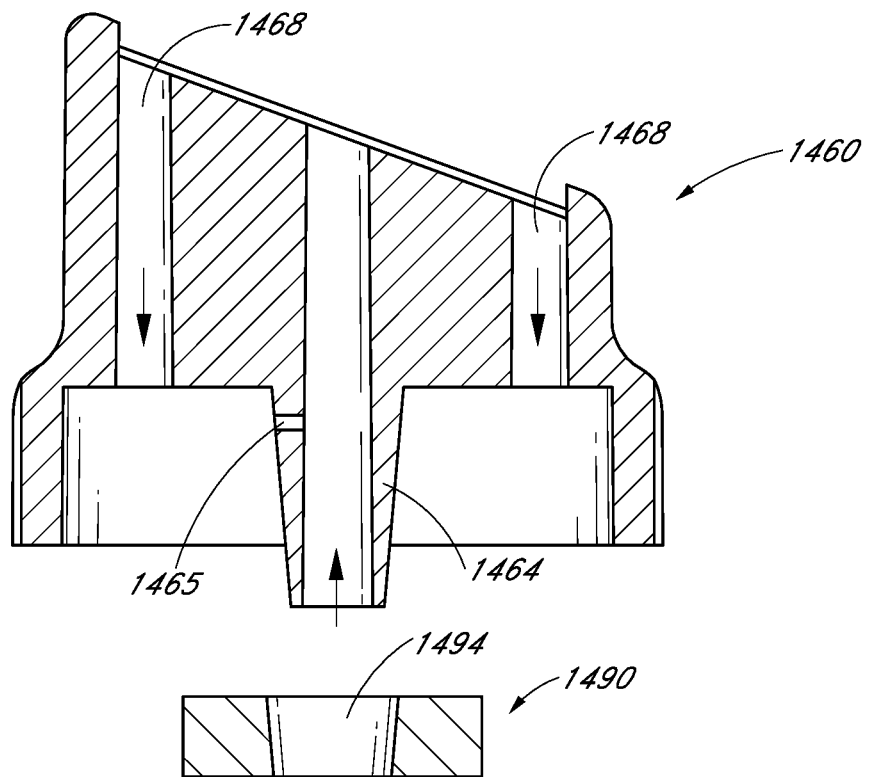
FIG. 15A illustrates an exploded cross-sectional view of another embodiment of a tip and a cartridge or other container comprising solids, gels and/or other materials.
Figure 15B:
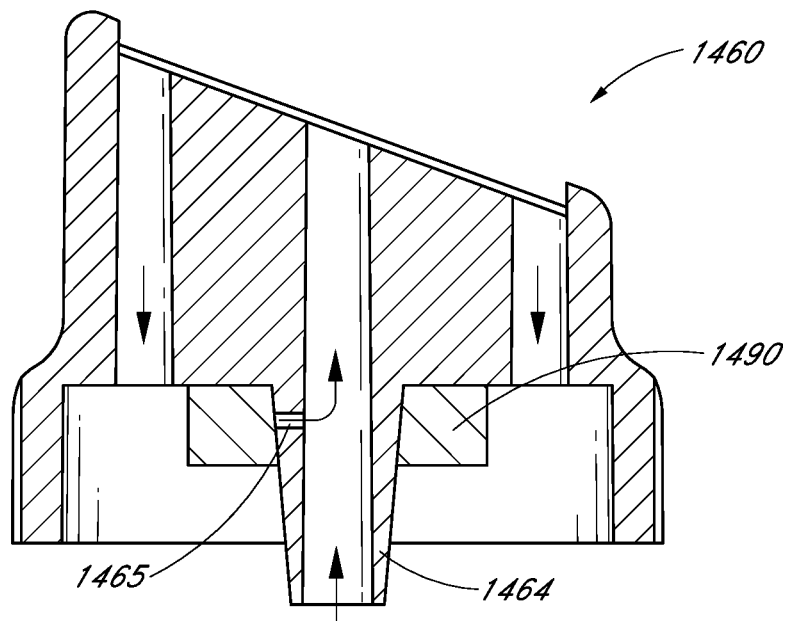
FIG. 15B illustrates a cross-sectional view of the cartridge and tip of FIG. 15A with the cartridge secured within an interior portion of the tip according to one embodiment.

Another embodiment of a disc 1490 that is configured to be secured to a tip 1460 of a handpiece assembly is illustrated in FIGS. 15A and 15B. As shown, the flow through the stem 1464 and the various conduits 1468 of the tip 1460 is generally reversed from the configuration of FIGS. 14A-14C. However, similar to the arrangement of FIGS. 14A-

14C, the depicted disc 1490, capsule or other item is configured to secure to an exterior portion of the stem 1464.

With continued reference to FIGS. 15A and 15B, the solids, gels, concentrated fluids and/or other materials contained within an interior of the disc 1490 can be configured to come into contact with water, saline, other dilutants or dissolvents and/or other fluids being conveyed through the internal passage of the stem 1464. Accordingly, such materials can be dissolved, diluted, softened, mixed and/or otherwise combined with such fluids before being carried to the distal end of the tip 1460.

The final products being delivered to the skin can include, without limitation, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance. Alternatively, such solids, gels and/or other materials can be impregnated or otherwise positioned along one or more exterior surfaces of the disc 1490 (e.g., along the inner diameter of the opening 1494). As discussed with reference to other embodiments disclosed herein, the disc 1490 can be partially or completely formed from such dissolvable or removable materials, so that it loses mass over time (e.g., as water or other liquids come in contact with it). In other embodiments, the disc 1490 comprises a porous container (e.g., cage) that is configured to house one or more solids, gels and/or other materials therein. In such arrangements, the disc 1490 can be removed, refilled, replaced and/or reused, as desired or required.

In FIGS. 15A and 15B, the stem 1464 of the tip comprises one or more side openings 1465 through which the materials and other substances contained on and/or within the disc 1490 may exit. Further, such openings 1465 can permit water, saline and/or other fluids being conveyed through the stem to enter an interior of the disc 1490 in order to advantageously dissolve, dilute and/or otherwise mix with the various materials contained therein. In some embodiments, the disc 1490 includes one or more openings that generally correspond to and align with the side openings 1465 of the stem 1460. Alternatively, the disc 1490, capsule or other item can comprise a cage or other porous structure to permit the various solids, gels, concentrated fluids and/or other materials contained therein to pass toward the opening 1465 of the stem 1464. Such materials and substances can be dissolved, diluted or otherwise mixed with water, saline and/or other fluids either within an interior cavity of the disc 1490, along an exterior portion of the disc, within the passage of the stem 1464 and/or at any other location or portion of the tip 1460.

Figure 16A:
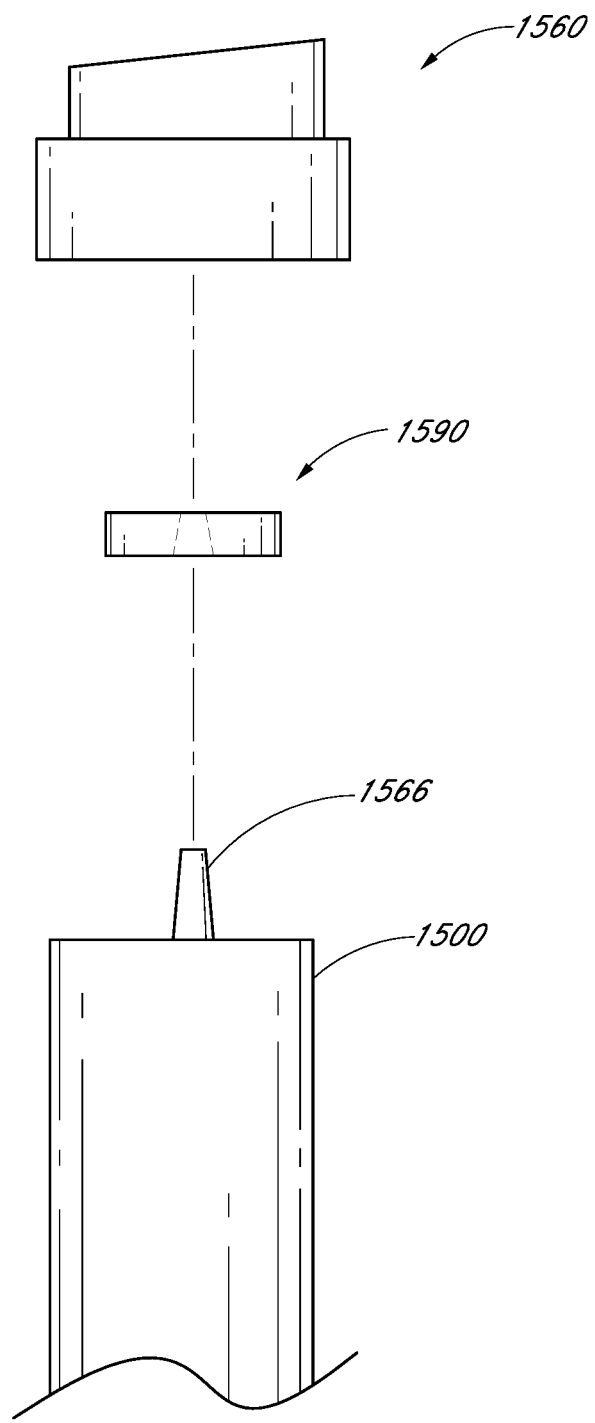
FIG. 16A schematically illustrates an exploded view of a handpiece assembly, a tip and a cartridge or other container according to another embodiment.
Figure 16B:
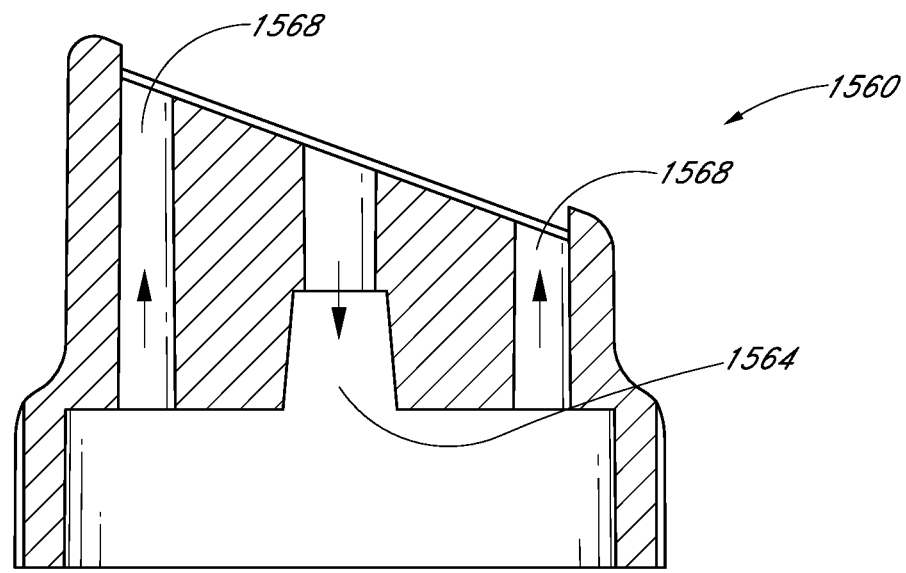
FIG. 16B illustrates an exploded cross-sectional view of another embodiment of a handpiece assembly, a tip and a cartridge or other container comprising solids, gels and/or other materials.
Figure 16B:
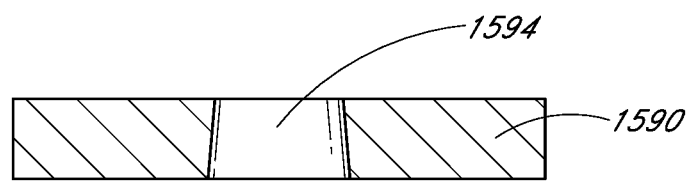
Figure 16B:
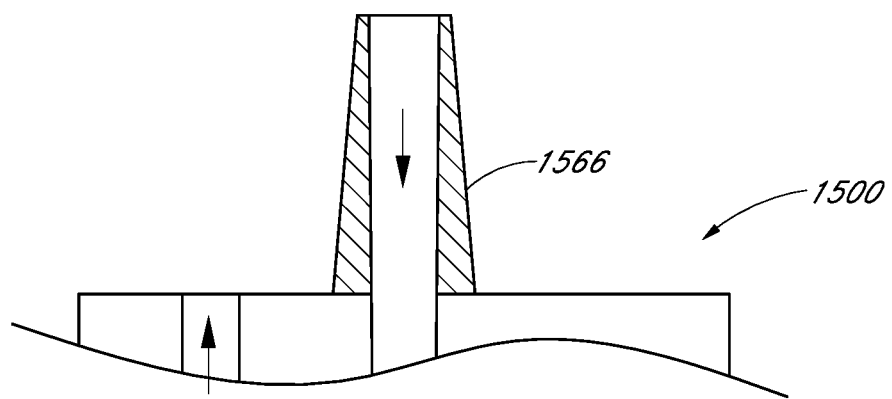

With reference to the schematic of FIG. 16A, a disc 1590, capsule or other item can be secured to a distal end of the main body portion 1500 of the handpiece assembly. For example, as illustrated in FIG. 16B, a central opening 1566 of the disc 1590 can be positioned over a nozzle 1566 or other protruding member of the handpiece assembly. As discussed with reference to other embodiments herein, including the discs of FIGS. 14A-14C, 15A and 15B, exterior and/or interior portions of the disc 1590 can include one or more solids, granulated materials, semi-solids, gels, concentrated fluids and/or other substances that are configured to be contacted by water, saline, other dilutants or dissolvents and/or other fluids. The resulting materials that are selectively delivered to the distal end of the tip 1560 (e.g., through one or more delivery passages or conduits 1568) can include, without limitation, growth factors, cytokines, soluble collagen, antioxidants, matrix proteins, serums, brightening or lightening agents, peptides, acid, water (e.g., distilled, tap water, filtered, etc.), saline, other dilutants or dissolvents, vitamins, chemical exfoliation agents, lotions, soothing agents, anesthetics, medicants, other non-active or active compounds, other fluids or materials, combination or mixtures thereof and/or any other substance.

Figure 17:
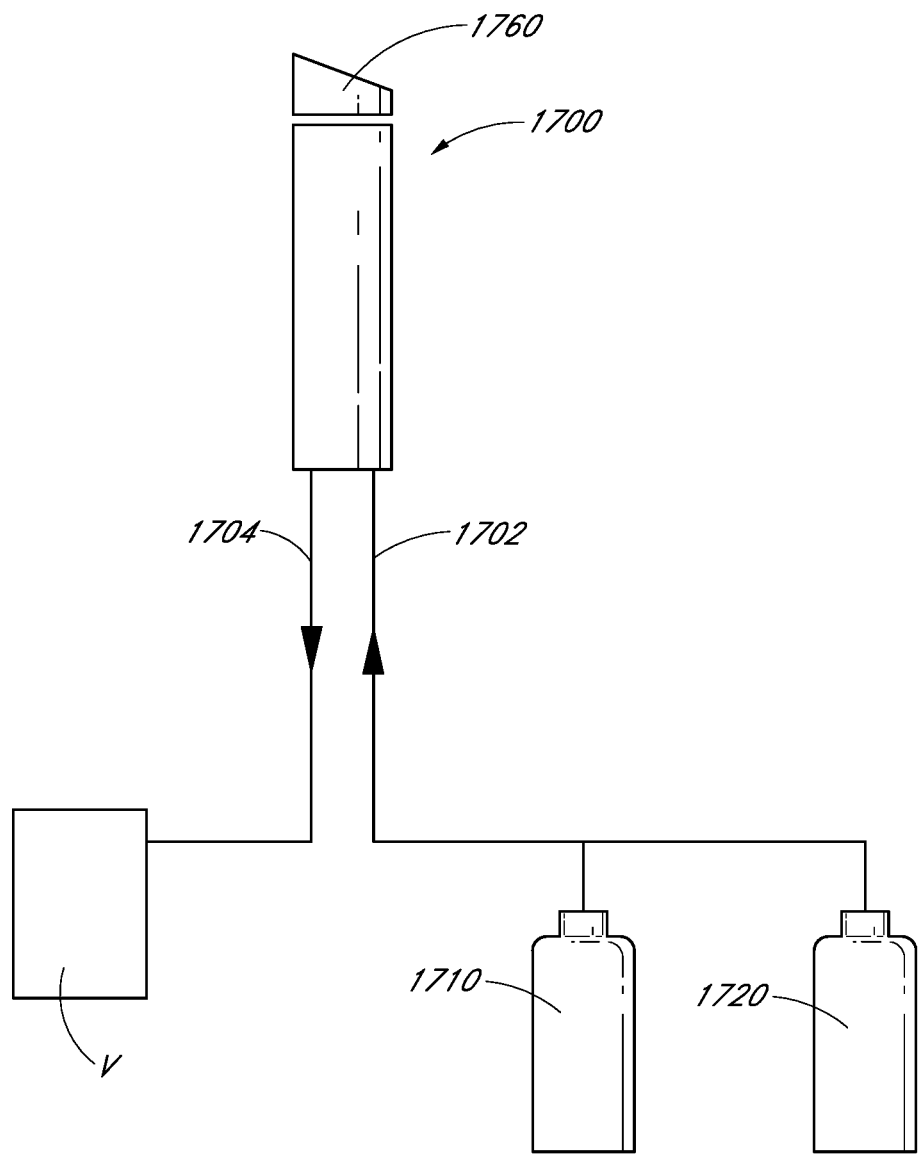
FIG. 17 schematically illustrates a handpiece assembly in fluid communication with a vacuum source and two supply containers according to one embodiment.

FIG. 17 schematically illustrates one embodiment of a handpiece assembly 1700 which is in fluid communication with a vacuum V or other suction force via a vacuum line 1704. In addition, the depicted assembly is in fluid communication with one or more containers 1710, 1720 via a delivery line 1702. As discussed herein, the delivery line 1702 can be placed in fluid communication with one or more different treatment materials, such as, for example, growth factors, cytokines, soluble collagen, antioxidants, matrix proteins, serums, water, saline, other dilutants or dissolvents, vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance. Such materials can be selectively transferred from their respective containers, through the delivery line and to the handpiece assembly 1700 in their usable, ready-to-use form (e.g., with the concentration and other manner in which they will be delivered to the skin surface being treated).

Alternatively, water (e.g., tap, filtered, sterile, distilled, etc.), saline, other dilutants or dissolvents and/or other fluids can be stored within one or more of the containers 1710, 1720 located upstream of the handpiece assembly 1700. As discussed, such liquids and other fluids can be selectively delivered to the handpiece assembly 1700 in order to dissolve, dilute and/or mix with solids, gels, concentrated fluids, other materials and/or the like that are impregnated, deposited, stored or otherwise situated on or near the tip 1760.

In other embodiments, one or more of the upstream containers (e.g., container 1710 in FIG. 17) can be configured to store a cleaning solution. Accordingly, such solutions or other cleaning agents can be selectively conveyed through the delivery conduits 1702 and other interior portions of the handpiece assembly 1700, the tip 1760 and/or any other component or portion of a skin treatment system as part of a cleaning protocol. For example, the cleaning solutions and other agents can be used between skin treatment procedures, during a skin treatment procedure, in accordance with some predetermined cleaning schedule (e.g., once a day, once every two or three days, once a week, etc.), in accordance with some other desired or required protocol (e.g., to satisfy regulatory requirements, quality control standards, etc.) and/or the like. In some embodiments, the cleaning agents include biocides, antimicrobial solutions, disinfectants, other sterilizing agents and/or the like. Such a configuration that includes a handpiece assembly in fluid communication with one or more cleaning solutions or agents can be incorporated into any of the embodiments disclosed herein, or variations thereof.

Figure 18A:
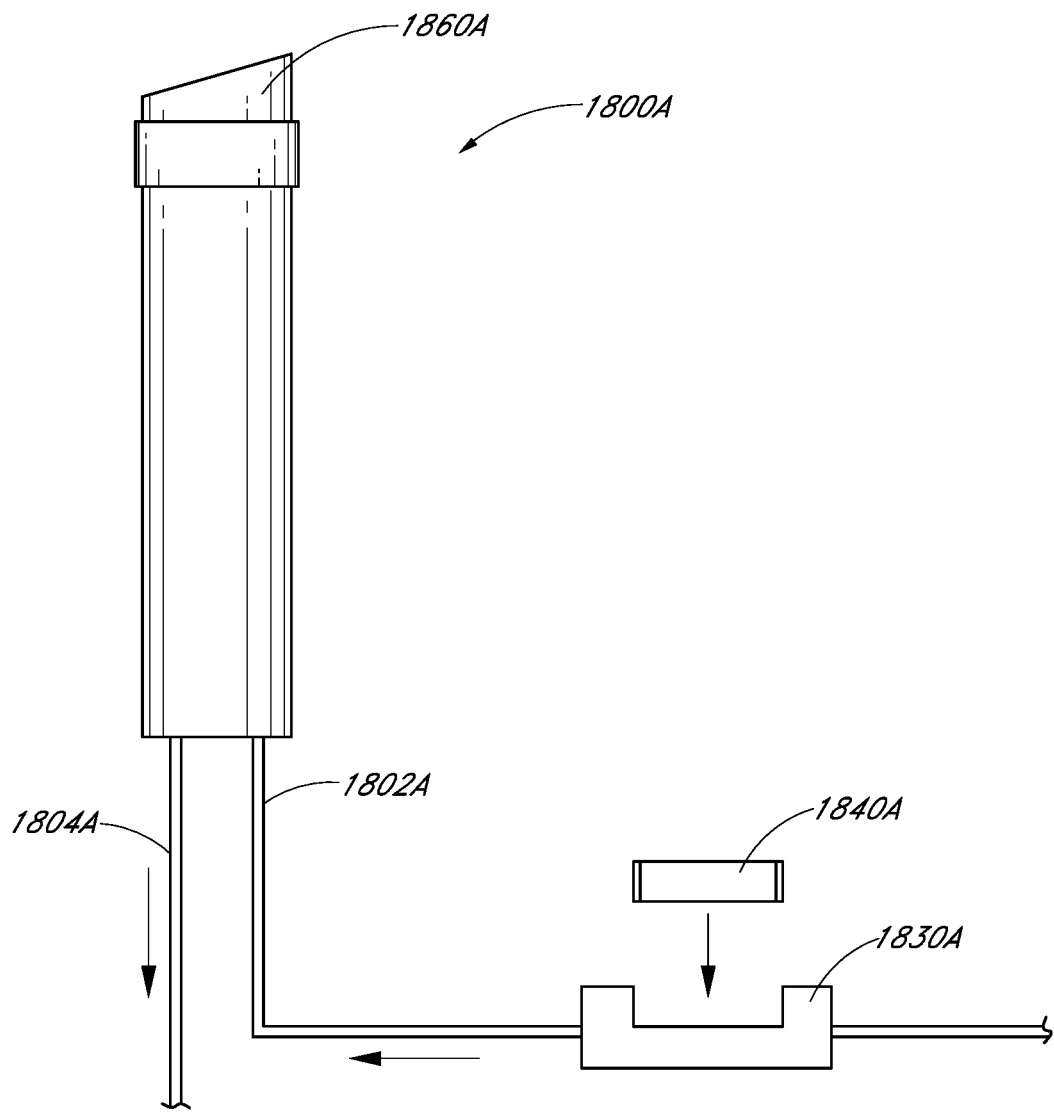
FIG. 18A schematically illustrates a handpiece assembly in fluid communication with a waste conduit and a supply conduit that comprises a cartridge holder adapted to receive a cartridge or other container according to one embodiment.

The schematic of FIG. 18A illustrates one embodiment of a skin treatment system that includes a handpiece assembly 1800A, a suction line 1804A in fluid communication with a vacuum or other suction source and a delivery line 1802A in fluid communication with one or more fluids, materials or other substances. As shown, the delivery line 1802A can include a cartridge holder 1830A or other device configured to accept a container 1840A. In some arrangements, the cartridge holder 1830A is sized, shaped and otherwise adapted to securely receive a standard or non-standard vial, ampoule and/or any other container 1840A. In certain configurations, such containers comprise one or more treatment fluids or other materials that can be selectively transferred to the tip 1860A during a procedure. As discussed, these substances can include, without limitation, growth factors, cytokines, soluble collagen, antioxidants, matrix proteins, brightening or lightening agents, peptides, peeling agents, acids, serums, water, saline, other dilutants or dissolvents, vitamins, chemical exfoliation agents, lotions, soothing agents, anesthetics, medicants, other non-active or active compounds, other fluids or materials, combination or mixtures thereof and/or the like.

According to certain embodiments, the fluids and/or other materials included in the cartridge 1840A are in their final, ready-to-use state. Thus, the contents of a cartridge 1840A can be directly delivered to the tip 1860A (e.g., as a result of a suction force imparted on the delivery line 1802A) without being diluted, dissolved or mixed with any other fluid or substance. Alternatively, a cartridge 1840A can comprise solids, granulated materials, gels, concentrated solutions and/or the like that are adapted to be combined with one or more fluids, other dissolvents or dilutants and/or other fluids (e.g., water, saline, etc.). For instance, such fluids can be conveyed from the upstream delivery line and combined with the internal contents of a cartridge 1840A or other container when such a cartridge 1840 is properly positioned within a holder 1830A.

The embodiment illustrated in FIG. 18A can provide a convenient way of selectively loading and unloading treatment fluids and/or other materials prior to, during or following a procedure. In some embodiments, fluids and/or other materials (e.g., water, other treatment fluids or substances, etc.) are configured to be conveyed through the cartridge holder 1830A from an upstream source even if a cartridge 1840A or other container is not positioned within the cartridge holder 1830A.

Figure 18B:
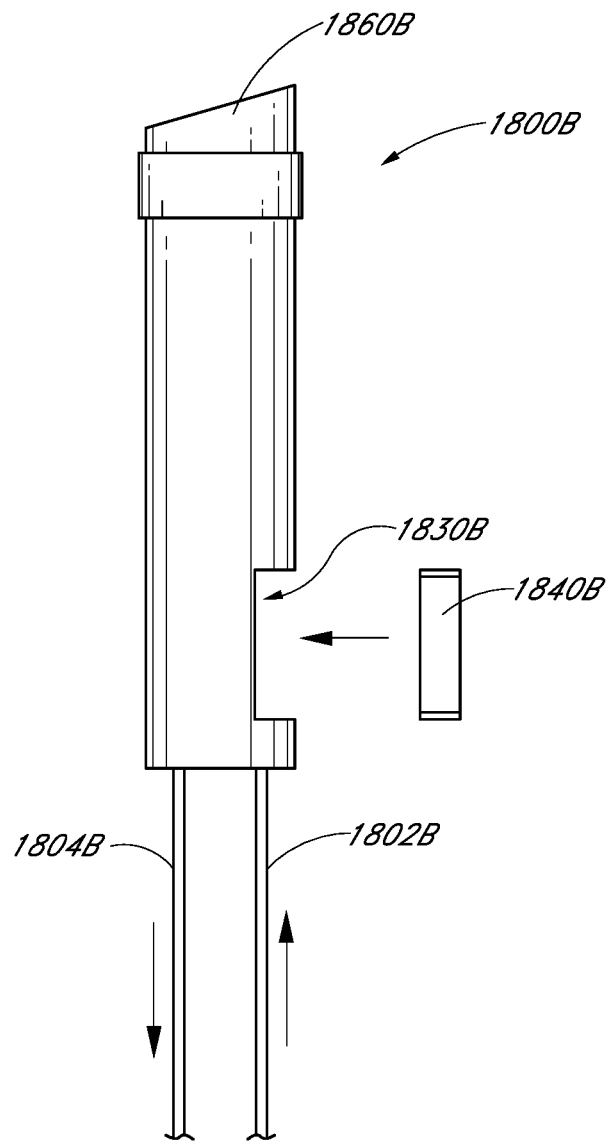
FIG. 18B schematically illustrates a handpiece assembly configured to receive a cartridge or other container according to one embodiment.

FIG. 18B illustrates a variation of the embodiment depicted in FIG. 18A. As shown, a standard or non-standard cartridge 1840B or other container can be configured to be selectively positioned within a corresponding slot or other receiving area 1830 of the handpiece assembly 1800B. As discussed with reference to FIG. 18A, the cartridge 1840A can comprise one or more treatment agents, fluids, materials and/or other substances. Such substances can be provided in their final, ready-to-use state. Alternatively, such materials can be provided as solids, granulated materials, gels, concentrated solutions and/or other forms that require contact and/or mixing with water, saline or the like before they are ready for use (e.g., prior to being delivered to the tip 1860 of the handpiece assembly, prior to contacting the skin, etc.). The embodiments illustrated in FIGS. 18A and 18B can be incorporated into any of the embodiments of a skin treatment system disclosed herein, or variations thereof.

Figure 19A:
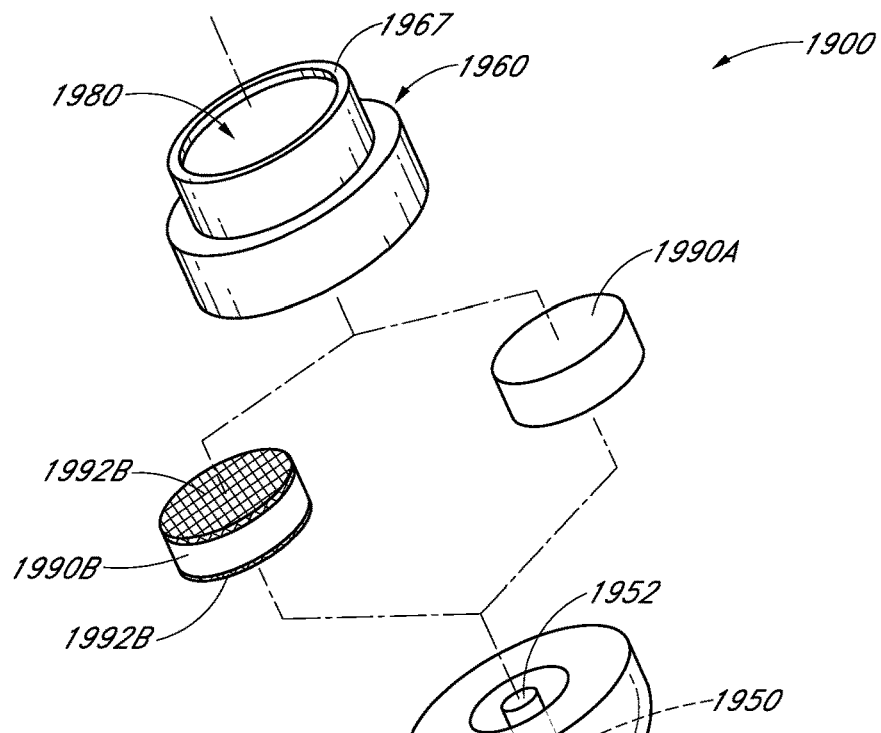
FIG. 19A illustrates an exploded perspective view of a handpiece assembly, a tip and pads configured to be secured therebetween according to one embodiment.

FIG. 19A illustrates another embodiment of a handpiece assembly 1900 adapted for use in a microdermabrasion or other skin treatment system. As shown, the handpiece assembly 1900 can include a main body portion 1910 and a tip 1960 configured to removably attach to the distal end of the main body portion 1910. The main body portion 1910 can include one or more conduits passing therethrough. In the depicted arrangement, the main body portion 1910 includes a single removal conduit 1950 which is positioned at or near the longitudinal centerline of the handpiece assembly and which daylights at an opening 1952 at the distal end of the main body portion 1910. The removal conduit 1950 can be placed in fluid communication with a vacuum or other suction source using a waste conduit 1954 to selectively transfer exfoliated skin, spent treatment fluids, debris and other waste materials away from the tip 1960.

Figure 19B:
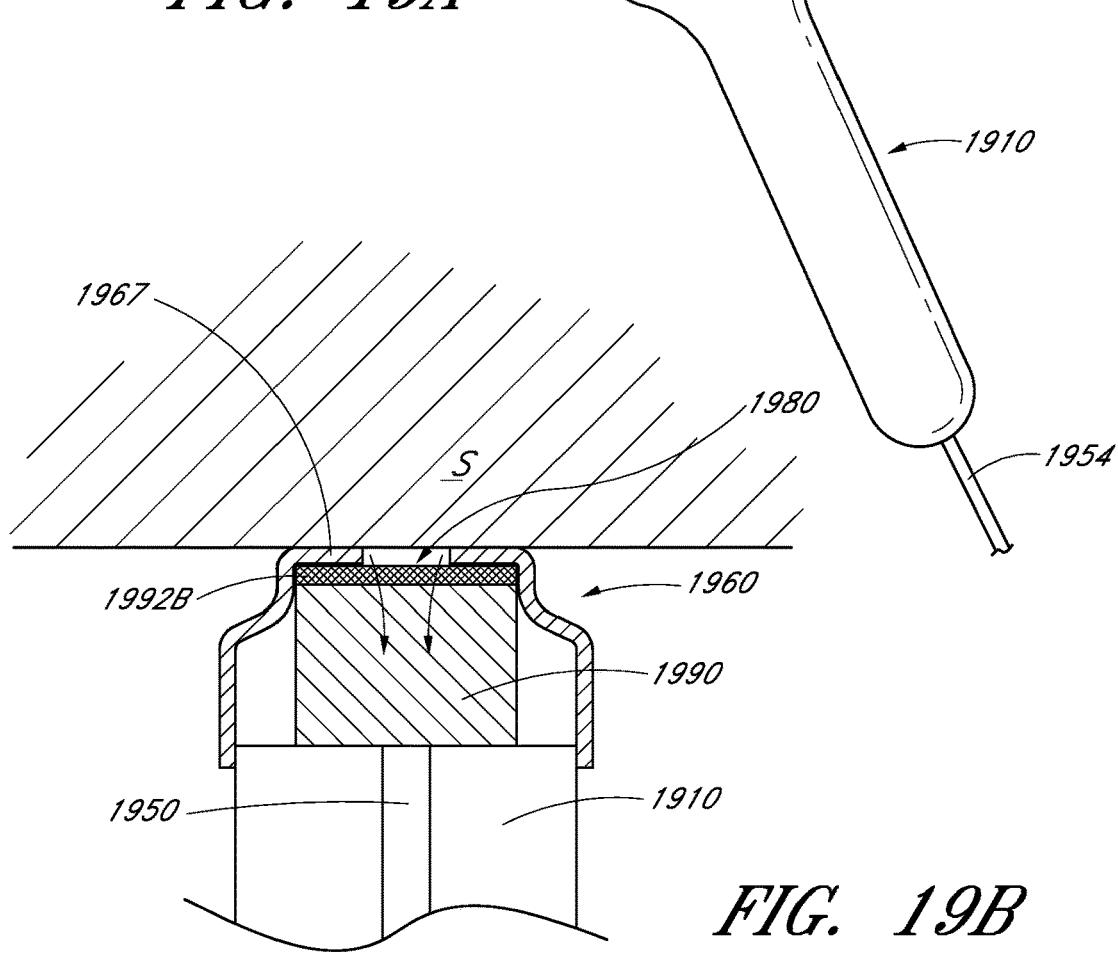
FIG. 19B illustrates a cross-sectional view of the tip, a pads and the handpiece assembly of FIG. 19A.
Figure 20A:
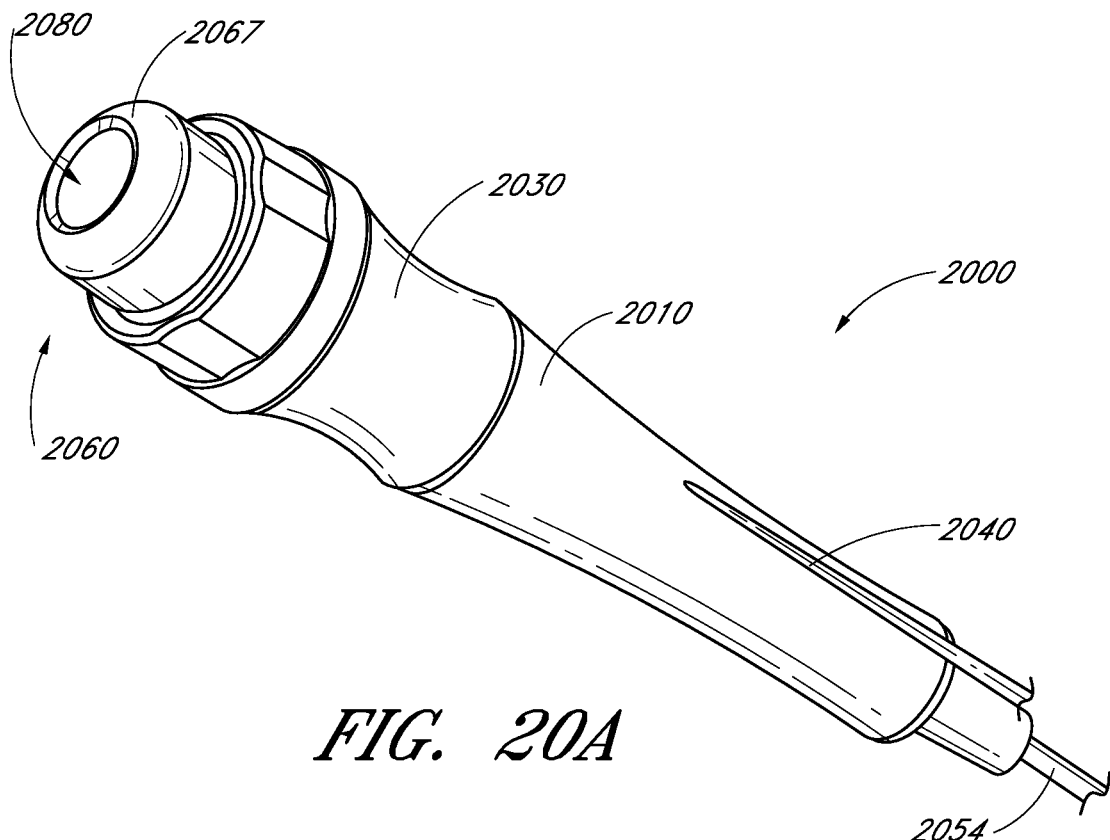
FIG. 20A illustrates an perspective view of a handpiece assembly configured to receive a pad according to another embodiment.
Figure 20D:
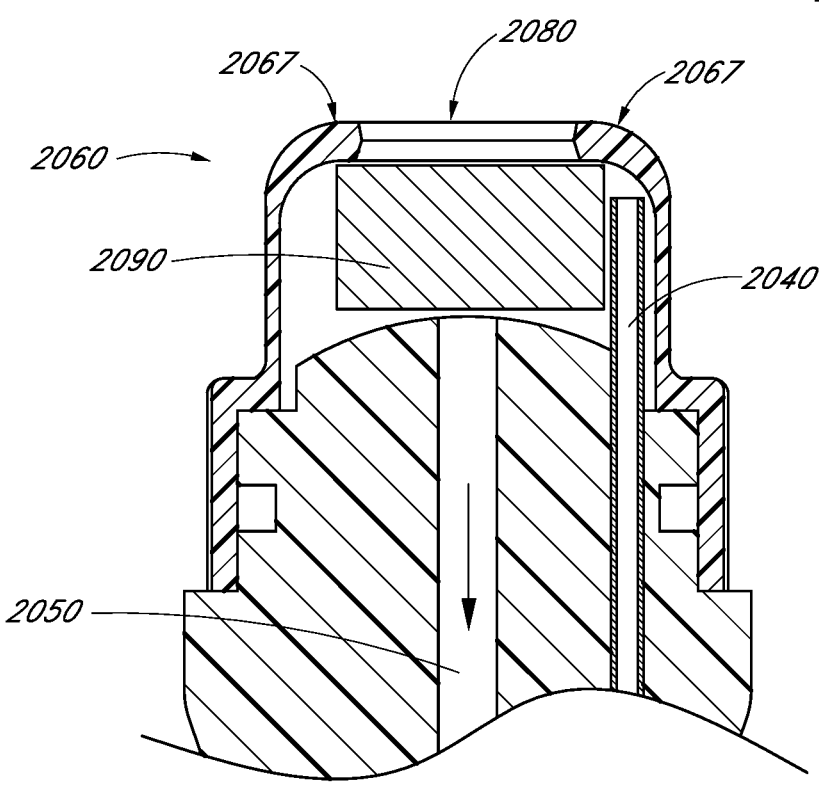
FIG. 20D illustrates a detailed cross-sectional view of the handpiece assembly of FIG. 20A comprising a pad secured within an interior portion of its tip according to one embodiment.

With continued reference to FIG. 19A, the distal end of the tip 1960 can include one or more openings 1980 defined within a peripheral lip 1967. According to certain arrangements, the handpiece assembly 1900 is sized, shaped and otherwise configured to receive a removable pad 1990A, 1990B or other member within an interior of the tip 1960. Thus, as illustrated in FIGS. 19A and 19B, such a pad 1990A, 1990B or other member can be generally positioned between the tip 1960 and the main body portion 1910 when the tip 1960 is properly secured to the handpiece assembly 1900. The pads can have a diameter (or other cross-sectional dimension) that is greater than the opening 1980 along the distal end of the tip 1960. Accordingly, the pad 1990A, 1990B or other member can be securely retained below the opening 1980 and within the tip 1960 during use.

As illustrated in the cross-sectional view of FIG. 19B, an upper surface of the pad 1990 can be configured to contact a skin surface S through the tip opening 1980 during use. Thus, in some embodiments, the upper surface of a pad is configured to exfoliate skin when it is translated or otherwise moved relative to a skin surface. The pad 1990 can comprise foam and/or any other materials. In one arrangement, the pad 1990 comprises one or more polymeric materials. However, the pads or other device can include one or more other natural or synthetic materials, either in lieu of or in addition to plastics and other polymers, as required to achieve a desired texture, coarseness, roughness and/or other exfoliation characteristics.

In some embodiments, as illustrated in FIG. 19A, the upper and/or lower surfaces 1992B of the pad 1990B include a texture that is coarser than other portions of the pad 1990B. For example, the pad 1990B can include grit, a sandpaper-like finish, an uneven finish, harder or more rigid materials and/or the like along its upper and/or lower surfaces 1992B. Such a configuration can further enhance the skin exfoliating properties of the pad. In arrangements where it includes both upper and lower textured surfaces 1992B, the pad 1990B can be flipped to selectively place the desired surface 1992B along the distal end of the tip 1960. For example, after the first surface 1992B has been used for a particular time period or after the effectiveness of the first surface 1992B has generally diminished or deteriorated, a user can remove the tip 1960 and turn the pad 1990B around to expose the second surface 1992B to the skin surface S being treated. This can effectively extend the useful life of a pad. In other embodiments, however, a pad 1990A can include one or no textured surfaces. For instance, a pad 1990A without any roughened surfaces can be used as a final, polishing skin surfacing step. According to certain embodiments, a user can be provided with an assortment of pads 1990 each of which having varying skin surfacing characteristics. Thus, a user can customize his or her treatment procedure, as desired or required.

According to some embodiments, as shown in FIG. 19A, the pads are cylindrical is shape with generally flat upper and lower surfaces. However, the shape, size and/or other characteristics of the pads 1990 can vary. The pad 1990 can serve an additional function by being configured to filter some or all of the debris and other waste item being transferred from the distal end of the tip 1960 to the waste opening 1952 and removal conduit 1950 of the main body portion 1910. For example, the pad 1990 can comprise foam or another porous structure that effectively functions as a filter to help trap exfoliated skin and other waste materials. Thus, by preventing or reducing the amount of debris passing to the removal conduit 1950, the pad 1990 can advantageously extend the life of the handpiece assembly 1900 and the downstream components of the skin treatment system (e.g., the waste container, the waste line 1954, downstream filters, the vacuum or other suction source, etc.).

In some embodiments, a procedure may be enhanced by providing one or more treatment fluids, serums and/or other materials to the skin surface being treated. For example, as discussed in greater detail herein, it may desirable to selectively provide human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, anesthetics, medicants, other non-active or active compounds, other fluids or materials, combination or mixtures thereof and/or any other substance to the tip 1960 of the handpiece assembly 1900. As discussed, such fluids and/or other materials can be delivered to the tip 1960 using one or more delivery conduits, passages and other hydraulic components of the handpiece assembly 1900.

However, in embodiments which do not include such passages, such as the one illustrated in FIGS. 19A and 19B, the desired fluids and/or other materials can be included within the pad 1990 or other device situated between the tip 1960 and the main body portion 1910 of the assembly 1900-. Therefore, solids, gels, fluids and/or other materials included within the pads 1990 can be advantageously excreted or discharged onto the skin surface S during a treatment procedure. Such materials can be positioned within the pad body (e.g., foam or other absorbent structure), on the surface of the pad and/or at any location or region of the pad, as desired or required.

In order to adequately maintain the desired treatment fluids and/or other materials within the pads 1990, the pads 1990 can be included in an enclosed pouch or other sealed container. This will help ensure that the desired materials remain within and/or on the pad 1990 until such pads 1990 are inserted into a handpiece assembly 1900. In other embodiments, the pads include one or more solids, granular materials, gels, concentrated fluids and/or other substances that are configured to be contacted with water, saline, other dilutants or dissolvents and/or other fluids in order to convert them into a usable treatment material or mixture. Thus, an external fluid source can be used with the handpiece assembly 1900 of FIG. 19A. Alternatively, as discussed herein with reference to the embodiment of FIGS. 20A-20D and FIGS. 21A-21B, a handpiece assembly can comprise one or more fluid delivery conduits of its own. Additional information regarding tips configured to receive a pad or other device is provided in U.S. patent application Ser. No. 09/699,220, filed on Oct. 27, 2000 and issued on Oct. 7, 2003 as U.S. Pat. No. 6,629,983, the entireties of which is hereby incorporated by reference herein.

The handpiece assembly 2000 illustrated in FIGS. 20A-20D is similar to the embodiment of FIGS. 19A and 19B. However, the depicted embodiment additionally comprises a fluid delivery conduit 2040 that is configured to deliver one or more fluids, treatment materials and/or the like toward the skin surface being treated. As discussed in greater detail herein with reference to other arrangements, human growth factors, cytokines, soluble collagen, antioxidants, matrix proteins, serums, water (e.g., distilled, tap water, filtered, etc.), saline, other dilutants or vitamins, chemical exfoliation agents, lotions, soothing agents, brightening or lightening agents, peptides, peeling agents, acids, anesthetics, medicants, other non-active or active compounds, other fluids or materials, combination or mixtures thereof and/or any other substance can be delivered through the delivery conduit 2040. In other embodiments, the delivery conduit 2040 is adapted to convey water, saline, other dilutants or dissolvents and/or other fluids to the tip 2060 where they can be selectively mixed, combined or contacted with solids, semi-solids, gels, granulated materials, concentrated fluids or materials and/or the like in order to produce the desired treatment materials. As discussed with reference to other embodiments herein, such solids and/or other materials can be embedded, impregnated and/or otherwise disposed on, within or along the tip 2060, the pad 2090 (e.g., foam), a cartridge and/or any other component or portion which is in fluid communication with the handpiece assembly 2000.

Figures 21A, 21B:
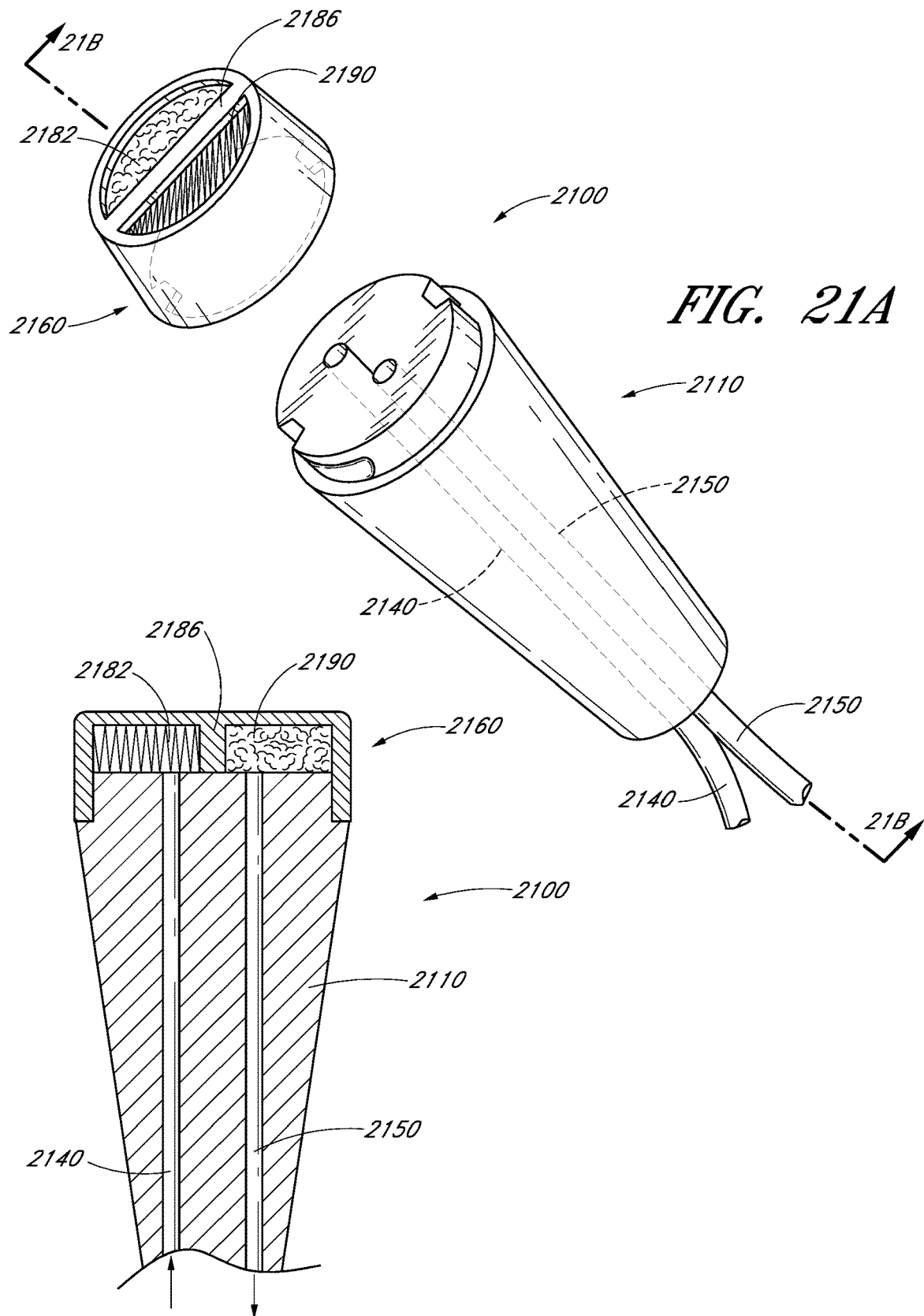
FIG. 21A illustrates an exploded perspective view of a handpiece assembly that is adapted to be in fluid communication with a vacuum source and a fluid delivery source according to one embodiment.
FIG. 21B illustrates a cross-sectional view of the handpiece assembly of FIG. 20A.

Another embodiment of a handpiece assembly 2100 is illustrated in FIGS. 21A and 21B. The main body portion 2110 of the assembly 2100 can include a delivery conduit 2140 and a waste conduit 2150. According to some embodiments, these conduits 2140, 2150 are routed along an interior of the main body portion 2110. However, one or both of these conduits can be positioned along the outside of the handpiece assembly 2100, as desired or required. Further, a removable tip 2160 can be configured to be secured along the distal end of the main body portion 2110.

With continued reference to FIGS. 21A and 21B, the tip 2160 can include a delivery zone 2182 or region and a waste zone 2190 or region. As shown, these zones 2182, 2190 can be separated by a septum 2186 or other member or feature. According to some embodiments, treatment fluids and/or other materials, such as, for example, human growth factors, cytokines, soluble collagen, antioxidants, matrix proteins, serums, water (e.g., distilled, tap water, filtered, etc.), saline, other dilutants or dissolvents, vitamins, chemical exfoliation agents, lotions, soothing agents, brightening or lightening agents (e.g., kojic acid), peptides, peeling agents, acids, anesthetics, medicants, other non-active or active compounds, other fluids or materials, combination or mixtures thereof and/or any other substances, are selectively transferred to the delivery zone 2182 via the delivery conduit 2140. Such fluids and/or other materials can originate from a cartridge (e.g., located within the handpiece assembly 2100, positioned upstream of the handpiece assembly 2100, etc.), a bottle or other container included as a part of a manifold system and/or any other source.

Alternatively, the delivery conduit 2140 can be configured to transfer only water, saline, other dilutants or dissolvents and/or other relatively clean fluids (e.g., fluids that have no solids or a low concentration of solids). In such configurations, as discussed in greater detail herein with reference to other arrangements, solids, semi-solids, granular materials, gels, concentrated solutions and/or other materials configured to be combined with the water, saline or other fluids being conveyed through the delivery conduits 2140 can be positioned within or near the delivery zone 2182. Thus, once water, saline and/or other fluids contact such materials, the desired or required treatment materials can be produced in the delivery zone 2182 and brought to the skin surface being exfoliated.

With further reference to FIGS. 21A and 21B, exfoliated skin, spent fluids and other treatment materials, debris and other waste materials can be removed from the tip 2160 to the waste conduit 22150 through the waste zone 2190. According to some embodiments, one or both of the zones 2182, 2190 include a pad or other member. For example, the delivery zone 2182 can include a pad or other member to help distribute the treatment fluids more evenly to the adjacent skin surface. In other arrangements, the pad or other member positioned within the delivery zone 2182 is saturated with or otherwise provided with solids, gels and/or other materials that can be selectively released to the skin once water or other fluids are conveyed to the delivery zone 2182. Likewise, the waste zone 2190 can include a pad or other member to help exfoliate skin and/or serve as a primary filter for the waste materials being carried away from the tip 2190.

In any of the embodiments of a handpiece assembly disclosed herein, or equivalent thereof, one or more of the various treatment materials and/or other substances being conveyed to the skin surface can be selectively heated. Heating of fluids and/or other material streams to a desired temperature can help enhance one or more aspects of a skin treatment procedure. For example, in some arrangements, heated fluids and/or other materials are generally better absorbed into a skin surface, as the skin pores may be caused to open because of the elevated temperature. In other embodiments, heated fluids and other materials advantageously stimulate improved blood circulation along the skin surface (e.g., dermis). Further, heating of water, saline and/or other dilutants or dissolvents can help improve the manner in which solids, granulated materials, gels, concentrated fluids and/or other materials impregnated or otherwise positioned on a handpiece assembly dissolve, dilute and/or otherwise transform into the desired final product.

According to some embodiments, one or more heating devices or mechanisms are positioned within or on a handpiece assembly (e.g., the main body portion, the adjustable distal portion, the tip, etc.). In other configurations, heaters are positioned upstream of the handpiece assembly, such as, for example, on or within a cartridge or other container, a cartridge holder, fluid delivery lines and/or the like.

Fluid and/or other material streams being conveyed through a handpiece assembly can be heated conductively or convectively, as desired or required. Adequate heating devices or systems can include resistive heaters, other electrical heaters and/or the like. In other embodiments, heated air or other fluids can be used to thermally transfer heat to fluids and/or other materials being delivered through a handpiece assembly. In addition, such heaters can include one or more sensors, feedback loops, controllers and/or other components to help maintain the treatment materials being delivered to the skin surface at or near a desired temperature or within a desired range.

In some embodiments, one or more serums, other fluids and/or substances can be selectively delivered to or near a treatment surface of a handpiece assembly to help remedy a particular skin condition. For example, the system can be used to treat acne, dry or oily skin, fine lines, sun-damaged skin, other skin diseases or disorders and/or like. Further, the serums, other fluids, other materials and/or mixtures thereof can be customized to target a particular disorder, ailment, other treatable or chronic condition, skin type and/or the like.

In another embodiment, serums, medicants, other fluids, other materials, combinations thereof and/or the like are used during a follow-up step or procedure (e.g., secondary, tertiary, polishing, etc.) or post-treatment phase. For example, such materials and/or mixtures can be used to hydrate the skin and/or lighten treat skin damage, either in lieu of or in addition to exfoliating skin. In any such embodiments, the serums or other fluids or materials can comprise human growth factors, cytokines, soluble collagen, matrix proteins, other proteins, anti-oxidants, hyaluronic acid, medicants and/or the like.

According to certain configurations, the serums, other fluids, other materials and/or mixtures thereof are used to target acne, oily skin, dry skin, other skin types and/or other skin conditions, diseases or ailments. Further, a particular treatment procedure can utilize one, two or more of such serums, medicants and/or other fluids, materials or substances during various treatment phases (e.g., exfoliation, finish or polishing treatment, post-treatment, etc.).

One or more kits developed to target a specific type of user, skin condition, disease or ailment, desired result and/or the like can be provided to a user. For example, such a kit can comprise serums, medicants, other fluids, other materials, mixtures thereof and/or the like that target teenage acne. As discussed, the serums and/or other materials contained in such kits can be in one or more different forms, such as, for example, liquids, gels, other fluids, powders, dissolvable tablets or other packs, solids and/or the like. In some embodiments, such serums and/or other materials are configured for immediate use (e.g., by not requiring any dilution, premixing or other preparatory steps by a user). Alternatively, a particular amount of water, saline or other liquids, other dilution or dissolving agents and/or the like may need to be added to achieve a usable product. Kits can include one or more cartridges or other containers that are configured to be placed onto and removed from a handpiece assembly as discussed herein.

In addition, depending on who the target user is (e.g., teenagers, adults, etc.) and/or how severe a particular condition is, the concentration or strength of the serums, medicants, other fluids or materials, mixtures thereof and/or the like can be selectively varied. For example, for younger users, a kit directed at acne treatment can comprise lower concentrations of serums and/or other materials. According to another example, kits comprising higher concentrations or strengths of serums, medicants and/or other substances can be used to treat oily skin or acne in adults. In other arrangements, a kit targets users whose skin is generally normal or typical (e.g., the users' skin is not abnormally dry or oily, the users do not have excessive amount of acne or scarring, etc.).

As discussed, the kits can comprise one, two or more different types of medicants, other active or non-active agents, serums, other fluids, other materials, mixtures thereof and/or the like, as desired or required. For example, a kit can comprise a first combination of serum(s) and/or other material(s) that is intended to be used during a basic skin exfoliation procedure. Further, a kit may include a second treatment combination that is used in a follow-up treatment to treat oily skin, dry skin, another skin type, a skin disease or ailment, another skin condition and/or the like. However, a kit may comprise more or fewer treatment combinations, as desired or required by a particular skin treatment procedure.

The systems, apparatuses, devices and/or other articles disclosed herein may be formed through any suitable means. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, it is not intended that the invention be limited, except as by the appended claims.

What is claimed is:

1. A method of treating skin of a subject, the method comprising:
    exfoliating skin tissue of the subject using a handpiece of a skin treatment system;
    wherein a distal end of the handpiece is configured to contact and abrade a skin surface with an at least one abrasive element;
    wherein the at least one abrasive element is fixedly positioned at or along the distal end of the handpiece; and
    wherein exfoliating skin tissue of the subject results from moving the distal end, including the at least one abrasive element, along the skin surface during use;
    delivering a treatment liquid from at least one treatment liquid source to the distal end of the handpiece and to the skin surface of the subject using the handpiece; and
    heating the treatment liquid being delivered to the skin surface of the subject.

2. The method of claim 1, wherein heating the treatment liquid comprises conductively heating the treatment liquid.

3. The method of claim 1, wherein heating the treatment liquid comprises convectively heating the treatment liquid.

4. The method of claim 1, wherein heating the treatment liquid is configured to occur using a heating member positioned at least partially within or on the handpiece.

5. The method of claim 1, wherein heating the treatment liquid is configured to occur using a heating member positioned upstream of the handpiece.

6. The method of claim 5, wherein the heating member is positioned on or in a fluid conduit placing the handpiece in fluid communication with the at least one treatment liquid source.

7. The method of claim 5, wherein the heating member is positioned on or in the at least one treatment liquid source.

8. The method of claim 7, wherein the at least one treatment liquid source is not physically secured to the handpiece.

9. The method of claim 1, wherein at least one aspect of the method of treating skin that is enhanced by heating treatment liquid comprises stimulating blood circulation along the skin tissue of the subject.

10. The method of claim 1, further comprising applying a vacuum along the skin tissue to remove at least a portion of exfoliated skin tissue and spent treatment liquid.

11. The method of claim 1, wherein the at least one treatment liquid source comprises a container configured to be secured to the handpiece.

12. The method of claim 1, wherein the at least one treatment liquid source comprises a manifold system, the manifold system configured to receive two or more bottles, the manifold system being in fluid communication with the handpiece using a fluid conduit.

13. The method of claim 1, wherein the handpiece comprises a tip, the tip positioned along the distal end of the handpiece.

14. A method of treating skin of a subject, the method comprising:
    exfoliating skin tissue of the subject using at least one abrasive element of a handpiece of a skin treatment system, wherein the handpiece is configured to contact a skin surface of the subject during use and abrade a skin surface with the at least one abrasive element, wherein the at least one abrasive element is fixedly positioned at or along the handpiece;
    delivering a treatment liquid from at least one treatment liquid source to the skin surface of the subject using the handpiece; and
    heating the treatment liquid being delivered to the skin surface of the subject.

15. The method of claim 14, wherein heating the treatment liquid comprises conductively heating the treatment liquid.

16. The method of claim 14, wherein heating the treatment liquid comprises convectively heating the treatment liquid.

17. The method of claim 14, wherein heating the treatment liquid is configured to occur using a heating member positioned at least partially within or on the handpiece.

18. The method of claim 14, wherein heating the treatment liquid is configured to occur using a heating member positioned upstream of the handpiece.

* * * * *